United States Patent
Wu et al.

(10) Patent No.: US 12,319,921 B2
(45) Date of Patent: Jun. 3, 2025

(54) TRANSGENIC PLANTS HAVING INCREASED BIOMASS

(71) Applicant: Ceres, Inc., Thousand Oaks, CA (US)

(72) Inventors: Chuan-Yin Wu, Newbury Park, CA (US); Han-Suk Kim, Camarillo, CA (US); Gerard Magpantay, Canoga Park, CA (US); Fasong Zhou, Fremont, CA (US); Julissa Sosa, Northridge, CA (US); Gregory Nadzan, Woodland Hills, CA (US); Roger I. Pennell, Malibu, CA (US); Mircea Achiriloaie, Thousand Oaks, CA (US); Wuyi Wang, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 154 days.

(21) Appl. No.: 17/459,304

(22) Filed: Aug. 27, 2021

(65) Prior Publication Data
US 2022/0056466 A1    Feb. 24, 2022

Related U.S. Application Data

(60) Division of application No. 15/676,845, filed on Aug. 14, 2017, now Pat. No. 11,162,108, which is a continuation of application No. 13/385,000, filed as application No. PCT/US2010/042602 on Jul. 20, 2010, now abandoned.

(60) Provisional application No. 61/226,969, filed on Jul. 20, 2009.

(51) Int. Cl.
C12N 15/82    (2006.01)

(52) U.S. Cl.
CPC ........ *C12N 15/8261* (2013.01); *Y02A 40/146* (2018.01)

(58) Field of Classification Search
None
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 5,766,847 A | 6/1998 | Jackie et al. |
| 6,013,863 A | 1/2000 | Lundquist et al. |
| 6,326,527 B1 | 12/2001 | Kirihara et al. |
| 6,329,571 B1 | 12/2001 | Hie |
| 6,423,885 B1 | 7/2002 | Waterhouse et al. |
| PP13,008 P2 | 9/2002 | Walsh |
| 6,452,067 B1 | 9/2002 | Bedbrook et al. |
| 6,573,099 B2 | 6/2003 | Graham |
| PP14,743 P2 | 5/2004 | Speichert et al. |
| 6,753,139 B1 | 6/2004 | Baulcombe et al. |
| 6,777,588 B2 | 8/2004 | Waterhouse et al. |
| PP15,193 P2 | 9/2004 | Smith et al. |
| 6,906,244 B2 | 6/2005 | Fischer et al. |
| PP16,176 P3 | 1/2006 | Cosner et al. |
| 7,214,789 B2 | 5/2007 | Pennell |
| PP18,161 P2 | 10/2007 | Probst |
| 7,312,376 B2 | 12/2007 | Apuya et al. |
| 7,378,571 B2 | 5/2008 | Apuya |
| 7,402,667 B2 | 7/2008 | Cook et al. |
| 7,429,692 B2 | 9/2008 | Chan |
| 7,445,654 B2 | 11/2008 | Wong |
| 7,598,367 B2 | 10/2009 | Cook et al. |
| 11,162,108 B2 | 11/2021 | Wu et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0123343 A1 | 6/2004 | La Rosa et al. |
| 2004/0172684 A1 | 9/2004 | Kovalic et al. |
| 2004/0214330 A1 | 10/2004 | Waterhouse et al. |
| 2005/0032221 A1 | 2/2005 | Chang et al. |
| 2005/0097638 A1 | 5/2005 | Jiang et al. |
| 2006/0015970 A1 | 1/2006 | Pannell et al. |
| 2006/0021083 A1 | 1/2006 | Cook |
| 2006/0041952 A1 | 2/2006 | Cook |
| 2006/0150283 A1 | 7/2006 | Alexander |
| 2006/0162006 A9 | 7/2006 | Sherman et al. |
| 2006/0260004 A1 | 11/2006 | Fang et al. |
| 2006/0265788 A1 | 11/2006 | Rommens |
| 2007/0006335 A1 | 1/2007 | Cook |
| 2007/0006346 A1 | 1/2007 | Nickolai et al. |

(Continued)

FOREIGN PATENT DOCUMENTS

| | | |
|---|---|---|
| WO | WO 1997/001952 | 1/1997 |
| WO | WO 1998/036083 | 8/1998 |

(Continued)

OTHER PUBLICATIONS

Zhang (2003) Curr Opin Plant Biol 6:430-40.*
Olsen et al. (2005) Trends Plant Sci 10(2):79-87.*
Guo et al. (2004) Proc Natl Acad Sci USA 101:9205-10, 9209.*
Tost et al. (2021) Genes 12:218.*
Amano et al. (2007) Proc Natl Acad Sci 104(46):18333-38.*
Samonte et al. (1998) Crop Sci 38:1130-46.*
Bing "Increase of 100%" (Jan. 24, 2025).*
U.S. Appl. No. 60/505,689, filed Sep. 23, 2003, Cook et al.
U.S. Appl. No. 60/518,075, filed Nov. 6, 2003, Pennell et al.
U.S. Appl. No. 60/544,771, filed Feb. 13, 2004, Cook et al.
U.S. Appl. No. 60/558,869, filed Apr. 1, 2004, Cook et al.
U.S. Appl. No. 60/583,609, filed Jun. 30, 2004, Alexandrov.

(Continued)

*Primary Examiner* — Russell T Boggs
(74) *Attorney, Agent, or Firm* — Dentons US LLP

(57) ABSTRACT

Methods and materials for modulating biomass levels in plants are disclosed. For example, nucleic acids encoding biomass-modulating polypeptides are disclosed as well as methods for using such nucleic acids to transform plant cells. Also disclosed are plants having increased biomass levels and plant products produced from plants having increased biomass levels.

13 Claims, 31 Drawing Sheets

Specification includes a Sequence Listing.

(56) References Cited

U.S. PATENT DOCUMENTS

| | | | |
|---|---|---|---|
| 2007/0020621 A1 | 1/2007 | Boukharov et al. | |
| 2007/0039067 A1* | 2/2007 | Feldmann et al. ... | C07K 14/415 536/23.6 |
| 2007/0056058 A1 | 3/2007 | Olivier et al. | |
| 2007/0079400 A1 | 4/2007 | Allen et al. | |
| 2007/0192900 A1 | 8/2007 | Sticklen | |
| 2007/0214517 A1 | 9/2007 | Alexandrov et al. | |
| 2008/0148432 A1 | 6/2008 | Abad | |
| 2009/0144847 A1 | 6/2009 | Shaikh et al. | |
| 2009/0158452 A1 | 6/2009 | Johnson et al. | |
| 2009/0183270 A1 | 7/2009 | Adams et al. | |
| 2011/0078818 A1 | 3/2011 | Kondo et al. | |
| 2011/0167514 A1 | 7/2011 | Brover et al. | |
| 2012/0297505 A1 | 11/2012 | Wu et al. | |
| 2014/0259225 A1 | 9/2014 | Frank et al. | |
| 2022/0056465 A1 | 2/2022 | Wu et al. | |

FOREIGN PATENT DOCUMENTS

| | | |
|---|---|---|
| WO | WO 1998/053083 | 11/1998 |
| WO | WO 1999/032619 | 7/1999 |
| WO | WO 2002/046449 | 6/2002 |
| WO | WO 2003/013227 | 2/2003 |
| WO | 2004035798 | 4/2004 |
| WO | WO 2005/098007 | 10/2005 |
| WO | WO 2006/005023 | 1/2006 |
| WO | WO 2006/034479 | 3/2006 |
| WO | WO 2006/036864 | 4/2006 |
| WO | 2007023190 | 3/2007 |
| WO | WO 2007/031581 | 3/2007 |
| WO | WO 2007/044988 | 4/2007 |
| WO | WO 2007/055826 | 5/2007 |
| WO | WO 2007/120989 | 10/2007 |
| WO | WO 2008/006033 | 1/2008 |
| WO | WO 2008/049183 | 5/2008 |
| WO | WO 2009/056566 | 5/2009 |
| WO | WO 2009/073069 | 6/2009 |
| WO | WO 2009/092009 | 7/2009 |

OTHER PUBLICATIONS

U.S. Appl. No. 60/583,691, filed Jun. 30, 2004, Alexandrov et al.
U.S. Appl. No. 60/612,891, filed Sep. 23, 2004, Kwok.
U.S. Appl. No. 60/637,140, filed Dec. 16, 2004, Feldmann.
U.S. Appl. No. 60/757,544, filed Jan. 9, 2006, Dang.
U.S. Appl. No. 60/776,307, filed Feb. 24, 2006, Kwok.
Office Action regarding European Application No. 13176038, dated Dec. 16, 2016.
Olsen et al., *Trends Plant Sci.*, 10(2):79-87, 2005.
Guo et al., *Proc. Natl. Acad. Sci. USA*, 101:9205-10, 2004.
Zhang, *Curr. Opin. Plant Biol.*, 6:430-40, 2003.
Whisstock & Lesk, *Q Rev Biophys.*, 36(3):307-40, 2003.
Yanagisawa, *Trends Plant Sci.*, 7(12)555-60, 2002.
Kovalchuk_EMBO J_19_17_4431_2000.
Hmm_SEQ ID No. 319 Is 08082014.
4B755_08082014.
SEQ ID No. 319 v K4B755_08082014.
SEQ ID No. 319 v SEQ ID No. 263_08052014.
Guo Proc Natl Acad Sci 101 9205 2004.
Chawade_BMC Gnmcs_8_304_2007.
WhisstockQ Rev Biophys_36_307_2003.
Extended European Search Report in EP Application No. 10802777.2, dated Feb. 14, 2013, 9 pages.
Extended European Search Report in EP Application No. 13176038.1, dated Oct. 4, 2013, 6 pages.
Authroized Officer S. Baharlou, International Preliminary Report on Patentabilityin International Application No. PCT/US2010/042602, dated Feb. 2, 2012, 7 pages.
Authorized Officer K. Kim, International Search Report and Written Opinion in International Application No. PCT/US2010/042602, dated Feb. 28, 2011, 13 pages.

Abler et al., "Isolation and characterization of a genomic sequence encoding the maize Cat3 catalase gene," *Plant Mol. Biol.*, 22:10131-1038, 1993.
Akashi et al., "Gene Discovery by Ribozyme and siRNA Libraries," *Nature Rev Mol. Cell Biol.*, 6:413-422, 2005.
Alonso-Blanco et al., "The Use of Recombinant Inbred Lines (RILs) for Genetic Mapping," *Arabidopsis Protocols*, 82:137-146, 1998.
Baerson et al., "Developmental regulation of an acyl carrier protein promoter in vegetative and reproductive tissues," *Plant Mol. Biol.*, 22(2):255-267, 1993.
Bateman et al., "Pfam 3.1: 1313 multiple alignments and profiled HMMs match the majority of proteins," *Nucl. Acids Res.*, 27:260-262, 1999.
Braga et al., "Expression of the CrylAb Protein in Genetically Modified Sugarcane for the Control of *Diatraea saccharalis* (Lepidoptera: Crambidae)," *Journal of New Seeds*, 5:209-221, 2003.
Burr et al., "Mapping Genes Inbreds," *The Maize Handbook* (New York, NY, 249-254, 1994.
Burr et al., "Gene Mapping with Recombinant Inbreds in Maize," *Genetics*, 118:519-526, 1998.
Bustos et al., "Regulation of β-Glucuronidase Expression in Transgenic Tobacco Plants by an A/T-Rich, cis-Acting Sequence Found Upstream of a French Bean β-Phaseolin Gene," *Plant Cell*, 1(9):839-853, 1989.
Cerdan et al., "A 146 bp fragment of the tobacco Lhcbl*2 promoter confers very-low-fluence, low-fluence and high-irradiance responses of phytochrome to a minimal CaMV 35S promoter," *Plant Mol. Biol.*, 33:245-255, 1997.
Chen et al., "Functional analysis of regulatory elements in a plant embryo-specific gene," *Proc. Natl. Acad. Sci. USA*, 83:8560-8564, 1986.
Chenna et al., "Multiple sequence alignment with the Clustal series of programs," *Nucleic Acids Res.*, 31(13):3497-3500, 2003.
Conceicao et al., "A cotyledon regulatory region is responsible for the different spatial expression patterns of *Arabidopsis* 2S albumin genes," *Plant*, 5:493-505, 1994.
Conkling et al., "Isolation of Transcriptionally Regulated Root-Specific Genes from Tobacco," *Plant Physiol.*, 93:1203-1211, 1990.
Dai et al., "RF2b, a rice bZIP transcription activator, interacts with RF2a and is involved in symptom development of rice tungro disease," *Proc. Natl. Acad. Sci. USA*, 101(2):687-692, 2004.
De Feyter et al., Expressing Ribozymes in Plants, *Methods in Molecular Biology*, 4(43):403-415, 1997.
Do et al., "ProbCons: Probabilistic consistency-based multiple sequence alignment," *Genome Res.*, 15(2):330-40, 2005.
Durbin et al., Biological Sequence Analysis: Probabilistic Models of Proteins and Nucleic Acids, *Cambridge University Press, Cambridge, UK*, 366 pages, 1998.
Fejes et al., "A 268 bp upstream sequence mediates the circadian clock-regulated transcription of the wheat Cab-1 gene in transgenic plants," *Plant Mol. Biol.*, 15:921-932, 1990.
Fromm et al., "An Octopine Synthase Enhancer Element Directs Tissue-Specific Expression and Binds ASF-1, a Factor from Tobacco Nuclear Extracts," *Plant Cell*, 1:977-984, 1989.
Gardiner et al., "Development of a Core RFLP Map in Maize Using an Immortalized $F_2$ Population," *Genetics*, 134:917-930, 1993.
GenBank No. AF096096, 1999, 2 pages.
GenBank No. AFI29516, 1999, 2 pages.
GenBank No. L05934, 1993, 3 pages.
GenBank No. U93215, 2002, 42 pages.
Green et al., "Binding site requirements for pea nuclear protein factor GT-1 correlate with sequences required for light-dependent transcriptional activation of the rbcS-3A gene," *EMBO J.*, 7:4035-4044, 1988.
Hong et al., "Promoter sequences for two different Brassica napus tapetal oleosin-like genes direct tapetal expression of β-glucuronidase in transgenic *Brassica* plants," *Plant Mol. Biol.*, 34(3):549-555, 1997.
Horton et al., "Protein Subcellular Localization Prediction with Wolf Psort," *Proceedings of the 4th Annual Asia Pacific Bioinformatics Conference*, 39-48, 2006.

(56) References Cited

OTHER PUBLICATIONS

Horton et al., "WoLF PSORT: Protein Localization Predictor," *Nucl. Acids Res.*, W585-W587, 2007.
Hwang et al., "Aleurone- and embryo-specific expression of the β-glucuronidase gene controlled by the barley Chi26 and Ltp1 promoters in transgenic rice," *Plant Cell Rep.*, 20:647-654, 2001.
Hyrup et al., "Peptide Nucleic Acids (PNA): Synthesis, Properties and Potential Applications," *Bioorgan. Med. Chem.*, 4:5-23, 1996.
Jordano et al., "A Sunflower Helianthinin Gene Upstream Sequence Ensemble Contains an Enhancer and Sites of Nuclear Protein Interaction," *Plant Cell*, 1:855-866, 1989.
Kasuga et al., "Improving plant drought, salt and freezing tolerance by gene transfer of a single stress-inducible transcription factor," *Nature Biotech*, 17:287-291, 1999.
Keller et al., "Vascular-Specific Expression of the Bean GRP 1.8 Gene is Negatively Regulated," *Plant Cell*, 3(10):1051-1061, 1991.
Lam et al., "Site-specific mutations alter in vitro factor binding and change promoter expression pattern in transgenic plants," *Proc. Natl. Acad. Sci. USA*, 86:7890-7894, 1989.
Li et al., "Small dsRNAs induce transcriptional activation in human cells," *Proc. Natl. Acad. Sci. USA*, 103(46):17337-17342, 2006.
Lloyd et al., "Targeted mutagenesis using zinc-finger nucleases in *Arabidopsis,*" *Proc. Natl. Acad. Sci. USA*, 102:2232-2237, 2005.
Luan et al., "A Rice cab Gene Promoter Contains Separate cis-Acting Elements that regulate expression in Dicot and Monocot Plants," *Plant Cell*, 4:971-981, 1992.
Lubberstedt et al., "Promoters from Genes for Plastid Proteins Possess Regions with Different Sensitivities toward Red and Blue Light," *Plant Physiol.*, 104:997-1006, 1994.
Matsuoka et al., "Tissue-specific light-regulated expression directed by the promoter of a $C_4$ gene, maize pyruvate, orthophosphate dikinase, in a $C_3$ plant, rice," *Proc. Natl. Acad. Sci. USA*, 90:9586-9590, 1993.
Matzke et al., "RNAi-Mediated Pathways in the Nucleus," *Nature Reviews Genetics*, 6:24-35, 2005.
McCallum et al., "Targeted screening for induced mutations," *Nat Biotech.*, 18: 455-457, 2000.
Medberry et al., "The Commelina Yellow Mottle Virus Promoter is a Strong Promoter in Vascular and Reproductive Tissues," *Plant Cell*, 4(2):185-192, 1992.
Meier et al., "Elicitor-Inducible and Constitutive in Vivo DNA Footprints Indicate Novel cis-Acting Elements in the Promoter of a Parsley Gene encoding Pathogenesis-Related Protein 1," *Plant Cell*, 3:309-316, 1991.
Mittal, "Improving the efficiency of RNA interference in mammals," *Nature Reviews Genetics*, 5:355-365, 2004.
Perriman et al., "Effective ribozyme delivery in plant cells," *Proc. Natl. Acad. Sci. USA*, 92(13):6175-6179, 1995.
Refseth et al., "Hybridization capture of microsatellites directly from genomic DNA," *Electrophoresis*, 18:1519-1523, 1997.
Riggs et al., "Cotyledone Nuclear Proteins Bind to DNA Fragments Harboring Regulatory Elements of Phytohemagglutinin Genes," *Plant Cell*, 1(6):609-621, 1989.
Rivera et al., "Genomic evidence for two functionally distinct gene classes," *Proc. Natl. Acad. Sci. USA*, 95:6239-6244, 1998.
Seo et al., "Jasmonic acid carboxyl methyltransferase: A key enzyme for jasmonate-regulated plant responses," *PNAS*, 98(8):4788-4793, 2001.
Sheridan et al., "The mac1 Gene: Controlling the Commitment to the Meiotic Pathway in Maize," *Genetics*, 142:1009-1020, 1996.
Shinshi, "Ethylene-regulated transcription and crosstalk with jasmonic acid," *Plant Science*, 175:18-23, 2008.
Shizuya et al., "Cloning and stable maintenance of 300-kilobase-pair fragments of human DNA in *Escherichia coli* using an F-factor-based vector," *Proc. Natl. Acad. Sci. USA*, 106(5):1660-1665, 2009.
Slocombe et al., "Temporal and Tissue-Specific Regulation of a *Brassica napus* Stearoyl-Acyl Carrier Protein Desaturase Gene," *Plant Physiol.*, 104(4):167-176, 1994.
Sonnhammer et al., "Pfam: A Comprehensive Database of Protein Domain Families Based on Seed Alignments," *Proteins*, 28:405-420, 1997.
Sonnhammer et al., "Pfam: multiple sequence alignments and HMM-profiles of protein domains," *Nucl. Acids Res.*, 26:320-322, 1998.
Stemple, "Tilling—a high-throughput harvest for functional genomics," *Nat. Rev. Genet.*, 5(2):145-50, 2004.
Summerton et al., "Morpholino Antisense Oligomers: Design, Preparation, and Properties," *Antisense Nucleic Acid Drug Dev.*, 7:187-195, 1997.
Sun et al., "Crosstalk between jasmonic acid, ethylene and Nod factor signaling allows integration of diverse inputs for regulations of nodulation," *Plant J*, 46:961-970, 2006.
Tovkach et al., "A Toolbox and procedural notes for characterizing novel zinc finger nucleases for genome editing in plant cells," *Plant J*, 57:747-757, 2009.
Townsend et al., "High-frequency modification of plant genes using engineered zinc-finger nucleases," *Nature*, 459:442-445, 2009.
Truernit et al., "The promoter of the *Arabidopsis thaliana* SUC2 sucrose-$H^+$ symporter gene directs expression of β-glucuronidase to the phloem: Evidence for phloem: loading and unloading by SUC2," *Planta*, 196:564-570, 1995.
Urao et al., "Molecular cloning and characterization of a gene that encodes a MYC-related protein in *Arabidopsis,*" *Plant Mol. Biol.*, 32:571-57, 1996.
Watanabe et al., "Mechanism of Substrate Recognition and PLP-induced Conformational Changes in LL-Diaminopimelate aminotransferase from *Arabidopsis thaliana,*" *J Mol. Biol.*, 384:1314-1329, 2008.
Weigel et al., "Activation Tagging in *Arabidopsis,*" *Plant Physiology*, 122:1003-1013, 2000.
Yamamoto et al., "The Promoter of a Pine Photosynthetic Gene Allows Expression of a β-Glucuronidase Reporter Gene in Transgenic Rice Plants in a Light-Independent but Tissue-Specific Manner," *Plant Cell Physiol.*, 1994, 35:773-778, 1994.
Yan et al., "New Construct Approaches for Efficient Gene Silencing in Plants," *Plant Physiol.*, 141:1508-1518, 2006.
Zhang et al., "DNA Sequences that Activate Isocitrate Lyase Gene Expression during Late Embryogenesis and during Postgerminative Growth," *Plant Physiology*, 110:1069-1079, 1996.
Zhang et al., "From Laboratory to Field. Using Information From *Arabidopsis* to Engineer Salt, Cold, and Drought Tolerance in Crops," *Plant Physiol.*, 135:615-621, 2004.
Zheng et al., "SPK1 is an Essential S-Phase-Specific Gene of *Saccharomyces cerevisiae* that Encodes a Nuclear Serin/Threonine/Tyrosine Kinase," *Mol. Cell Biol.*, 13:5829-5842, 1993.
GenBank Accession No. AAV98701, dated Oct. 16, 2006.
GenBank Accession No. BT014677, dated May 21, 2004.
UniProtKB/Swiss-Prot Accession No. Q9SN52, dated Nov. 7, 2018.
European Extended Search Report regarding European Application No. 18192860, dated Nov. 15, 2018.
GenBank Accession No. BT064583.1, dated Feb. 21, 2009.
Zhao et al. (2004) "Overexpression of LSH1, a member of an uncharacterized gene family, causes enhanced light regulation of seedling development," Plant J 37:694-706.
Londo et al. (2006) Proc Natl Acad Sci USA 103(25):9578-83.
Hong et al. (2010) J Genet Genom 37:101-15.
Press & Queitsch (2017) Genet 205:455-64.
Mendonca Vilela et al. (2017) Genome Biol Evol 9(2):266-78.
Batemann et al., Acta Cryst. (2010) F66:1148-52.
Tittonell et al. (2005) Agric Ecosys & Environ 105:213-20.
Committee Nat'l Acad Sci, Genetically Engineered Crops through 2015 (2016).
Zeigler & Barclay (2008) Rice 1:3-10.
Gravois & McNew (1993) Cros Sci 33:249-52.
U.S. Appl. No. 17/459,290, filed Aug. 27, 2021, Wu et al.
Niu et al., Ectopic expression of GhCOBL9A, a cotton glycosyl-phosphatidyl inositol-anchored protein encoding gene, promotes cell elongation, thickening and increased plant biomass in transgenic *Arabidopsis*, Molecule Genetics and Genomics 293:1191-1204, 2018.

(56) References Cited

OTHER PUBLICATIONS

Sato et al., The carbohydrate-binding module (CBM)-like sequence is crucial for rice CWA1/BC1 function in proper assembly of secondary cell wall materials, Plant Signaling & Behavior 5(11):1433-1436, 2010.
Brown et al., Identification of Novel Genes in *Arabidopsis* Involved in Secondary Cell Wall Formation using Expression Profiling and Reverse Genetics, the Plant Cell 17:2281-2295, 2005.
NCBI Blast Search Results for N-terminal Met Arg Leu Leu Phe Ser, Jul. 13, 2024.
U.S. Appl. No. 19/017,387, filed Jan. 10, 2025, Wu, et al.
U.S. Appl. No. 19/017,388, filed Jan. 10, 2025, Wu, et al.
U.S. Appl. No. 19/018,701, filed Jan. 13, 2025, Wu, et al.
U.S. Appl. No. 19/018,733, filed Jan. 13, 2025, Wu, et al.
U.S. Appl. No. 19/018,793, filed Jan. 13, 2025, Wu, et al.
Hedden. "The genes of the Green Revolution." Trends in Genetics, vol. 19 (1), pp. 5-9, (2003).
Fernandez, et al. "From dwarves to giants? Plant height manipulation for biomass yield." Trends in Plant Science, vol. 14 (8), pp. 454-461, (2009).

\* cited by examiner

| | | | |
|---|---|---|---|
| SEQ_ID_NO_660 | SAFGHRENIL | EAGRRLKEMF | GSKK | 465 |
| SEQ_ID_NO_653 | SAFGHRENIL | EAARRLKQLY | K--- | 464 |
| SEQ_ID_NO_655 | SAFGHRENIL | EAARRLKQLY | K--- | 469 |
| SEQ_ID_NO_657 | SAFGHRDNIL | EAARRLKQLY | K--- | 462 |
| SEQ_ID_NO_659 | SAFGHRENIL | EAARRXKQLY | K--- | 462 |
| SEQ_ID_NO_652 | GAFSHRGNVL | EACKRFKRLY | K--- | 459 |
| SEQ_ID_NO_651 | SAFGHRENIL | EACRRFKQLY | K--- | 461 |
| SEQ_ID_NO_649 | SAFGHRENVL | EACRRFKQLY | K--- | 461 |
| SEQ_ID_NO_645 | SAFGHRENVL | EACRRFKQLY | N--- | 458 |
| SEQ_ID_NO_647 | SAFGHRENVL | EACRRFKQLY | N--- | 462 |

Figure 5 Continued

```
SEQ_ID_NO_257  MAF GVRL C CLLLVFAVTS S ARNI SES DNE M A KG RSLK T NDY      48
SEQ_ID_NO_253  MTF VVRLLV CLLLTLTITS S ARNPVSVS GGFENSG QR SLL MVNVEDY    49
SEQ_ID_NO_255  MSF VLRL AV FLLLTLTVTY S - - SPSSVS VPVVK GI ER RSLI VNVKDY 47

SEQ_ID_NO_257  GDPL A NRGHD PSQRNKNW G SGGGRK G    75
SEQ_ID_NO_253  GDPSANPKHD PGV PPSATGQ RVVGR  G    75
SEQ_ID_NO_255  DGPSANPKHN PGT PPMT SQ RSPGR  G    73
```

| SEQ_ID_NO_210 | LCPTLPLPML | 226 |
| SEQ_ID_NO_209 | ANSSTPNQSFT | 191 |
| SEQ_ID_NO_230 | PTTTEQFQSA | 205 |
| SEQ_ID_NO_214 | . . EAKPPMQSX | 177 |
| SEQ_ID_NO_239 | . . EAKSSKQSS | 175 |
| SEQ_ID_NO_212 | GDESSSTHFQ | 175 |
| SEQ_ID_NO_226 | GDTSSSNLPM | 194 |
| SEQ_ID_NO_220 | VAEAVPP . . | 198 |
| SEQ_ID_NO_236 | GKEKEAEQSA | 284 |
| SEQ_ID_NO_238 | SKEKEGSAPSS | 305 |
| SEQ_ID_NO_232 | GSGTAPSAS . | 212 |
| SEQ_ID_NO_242 | GSGTAPSAS . | 212 |
| SEQ_ID_NO_241 | GSSAAPSN . | 208 |
| SEQ_ID_NO_234 | GSSAAPSH . | 215 |

TRANSGENIC PLANTS HAVING INCREASED BIOMASS

CROSS-REFERENCE TO RELATED APPLICATIONS

This application is a divisional of U.S. application Ser. No. 15/676,845, filed Aug. 14, 2017 (pending), which application is a continuation of U.S. application Ser. No. 13/385,000, filed Jun. 11, 2012 (abandoned), which application is a National Stage Application under 35 U.S.C. § 371 of International Application No. PCT/US2010/042602, filed Jul. 20, 2010, which application claims the benefit of U.S. Provisional Application Ser. No. 61/226,969, filed on Jul. 20, 2009. The disclosures of the prior applications are incorporated by reference in their entirety.

TECHNICAL FIELD

This document relates to methods and materials involved in modulating biomass levels in plants. For example, this document provides plants having increased biomass levels as well as materials and methods for making plants and plant products having increased biomass levels.

BACKGROUND

The present invention relates to methods of increasing biomass in plants and plants generated thereby. Plants having increased and/or improved biomass are useful for agriculture, horticulture, biomass to energy conversion, paper production, plant product production, and other industries. In particular, there is a need for increases in biomass for dedicated energy crops such as *Panicum virgatum* L. (switchgrass), *Miscanthus* x *gigantus* (*Miscanthus*), *Sorghum* sp., and *Saccharum* sp. (sugar cane). Throughout human history, access to plant biomass for both food and fuel has been essential to maintaining and increasing population levels. Scientists are continually striving to improve biomass in agricultural crops. The large amount of research related to increasing plant biomass, particularly for dedicated energy crops, indicates the level of importance placed on providing sustainable sources of energy for the population. The urgency of developing sustainable and stable sources of plant biomass for energy is underscored by current events, such as rising oil prices. The amount of biomass produced by plants is a quantitative trait affected by a number of biochemical pathways. There is a need for molecular genetic approaches to more rapidly produce plants having increased biomass. There is also a need to produce plant species that grow more efficiently and produce more biomass in various geographic and/or climatic environments. It would be desirable for such approaches to be applicable to multiple plant species (Zhang et al., *Plant Physiol.* 135: 615-621 (2004)). Despite some progress in molecular genetic approaches, there is also a need to identify specific genes and/or sequences that can be used to effectively increase biomass in plants.

SUMMARY

This document provides methods and materials related to plants having modulated levels of biomass. For example, this document provides transgenic plants and plant cells having increased levels of biomass, nucleic acids used to generate transgenic plants and plant cells having increased levels of biomass, methods for making plants having increased levels of biomass, and methods for making plant cells that can be used to generate plants having increased levels of biomass. Such plants and plant cells can be grown to produce, for example, plants having increased height, increased tiller number, or increased dry weight. Plants having increased biomass levels may be useful to produce biomass for food and feed, which may benefit both humans and animals. Plants having increased biomass levels may be useful in converting such biomass to a liquid fuel (e.g., ethanol), or other chemicals, or may be useful as a thermochemical fuel.

Methods of producing a plant having increased biomass are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 130, 340, 530, 120, 635, 65, 100, 480, 145, 280, or 1000 using an HMM generated from the amino acid sequences depicted in one of FIG. 1, 2, 3, 4, 5, 6, 7, 8, 9, 10, or 11, respectively. The plant has a difference in the level of biomass as compared to the corresponding level of biomass of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697. A plant produced from the plant cell can be used to generate a plant that has a difference in the level of biomass as compared to the corresponding level of biomass of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624,626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696. A plant produced from the plant cell has a difference in the level of biomass as compared to the corresponding level of biomass of a control plant that does not comprise the exogenous nucleic acid.

Methods of modulating the level of biomass in a plant are provided herein. In one aspect, a method comprises introducing into a plant cell an exogenous nucleic acid that comprises a regulatory region operably linked to a nucleotide sequence encoding a polypeptide. The HMM bit score of the amino acid sequence of the polypeptide is greater than about 130, 340, 530, 120, 635, 65, 100, 480, 145, 280, or 1000, using an HMM generated from the amino acid sequences depicted in one of FIG. 1, 2, 3, 4, 5, 6, 7, 8, 9, 10, or 11, respectively. A plant produced from the plant cell has a difference in the level of biomass as compared to the corresponding level of biomass of a control plant that does not comprise the exogenous nucleic acid.

In certain embodiments, the HMM score of the amino acid sequence of the polypeptide is greater than about 340, using an HMM generated from the amino acid sequences depicted in FIG. 2, wherein the polypeptide comprises a Dof domain zinc finger, having at least 60 percent or greater (e.g., 65, 70, 75, 80, 85, 90, 95, 99, or 100%) sequence identity to residues 130 to 192 of SEQ ID NO: 263, or Dof domain zinc fingers identified in the sequence listing.

In certain embodiments, the HMM score of the amino acid sequence of the polypeptide is greater than about 530, using an HMM generated from the amino acid sequences depicted in FIG. 3, wherein the polypeptide comprises a pytochelatin synthetase-like domain having at least 60 percent or greater (e.g., 65, 70, 75, 80, 85, 90, 95, 99, or 100%) sequence identity to residues 44 to 208 of SEQ ID NO: 117, or pytochelatin synthetase-like domains identified in the sequence listing.

In certain embodiments, the HMM score of the amino acid sequence of the polypeptide is greater than about 120, using an HMM generated from the amino acid sequences depicted in FIG. 4, wherein the polypeptide comprises a AP2 domain having at least 60 percent or greater (e.g., 65, 70, 75, 80, 85, 90, 95, 99, or 100%) sequence identity to residues 32 to 83 of SEQ ID NO: 1, or AP2 domains identified in the sequence listing.

In certain embodiments, the HMM score of the amino acid sequence of the polypeptide is greater than about 635, using an HMM generated from the amino acid sequences depicted in FIG. 5, wherein the polypeptide comprises a Aminotransferase class I and II domain having at least 60 percent or greater (e.g., 65, 70, 75, 80, 85, 90, 95, 99, or 100%) sequence identity to residues 88 to 453 of SEQ ID NO: 645, or Aminotransferase class I and II domains identified in the sequence listing.

In certain embodiments, the HMM score of the amino acid sequence of the polypeptide is greater than about 100, using an HMM generated from the amino acid sequences depicted in FIG. 7, wherein the polypeptide comprises a Myb-like DNA-binding domain having at least 60 percent or greater (e.g., 65, 70, 75, 80, 85, 90, 95, 99, or 100%) sequence identity to residues 13 to 62 of SEQ ID NO: 323, or Myb-like DNA-binding domains identified in the sequence listing.

In certain embodiments, the HMM score of the amino acid sequence of the polypeptide is greater than about 480, using an HMM generated from the amino acid sequences depicted in FIG. 8, wherein the polypeptide comprises an alpha/beta hydrolase fold domain having at least 60 percent or greater (e.g., 65, 70, 75, 80, 85, 90, 95, 99, or 100%) sequence identity to residues 35 to 257 of SEQ ID NO: 595.

In certain embodiments, the HMM score of the amino acid sequence of the polypeptide is greater than about 145, using an HMM generated from the amino acid sequences depicted in FIG. 9, wherein the polypeptide comprises a Rapid Alkalinization Factor (RALF) domain having at least 60 percent or greater (e.g., 65, 70, 75, 80, 85, 90, 95, 99, or 100%) sequence identity to residues 57 to 129 of SEQ ID NO: 77, or RALF domains identified in the sequence listing.

In certain embodiments, the HMM score of the amino acid sequence of the polypeptide is greater than about 280, using an HMM generated from the amino acid sequences depicted in FIG. 10, wherein the polypeptide comprises a protein of unknown function (DUF640) domain having at least 60 percent or greater (e.g., 65, 70, 75, 80, 85, 90, 95, 99, or 100%) sequence identity to residues 19 to 152 of SEQ ID NO: 209, or DUF640 domains identified in the sequence listing.

In certain embodiments, the HMM score of the amino acid sequence of the polypeptide is greater than about 1000, using an HMM generated from the amino acid sequences depicted in FIG. 11, wherein the polypeptide comprises a POT family domain having at least 60 percent or greater (e.g., 65, 70, 75, 80, 85, 90, 95, 99, or 100%) sequence identity to residues 100 to 509 of SEQ ID NO: 426, or POT family domains identified in the sequence listing.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697. A plant produced from the plant cell has a difference in the level of biomass as compared to the corresponding level of biomass of a control plant that does not comprise the exogenous nucleic acid. The polypeptide in any of the above methods can have the amino acid sequence set forth in SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696, or a fragment thereof. A plant produced from the plant cell has a difference in the level of biomass as compared to the corresponding level of biomass of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 130, 340, 530, 120, 635, 65, 100, 480, 145, 280, or 1000, using an HMM based on the amino acid sequences depicted in one of FIG. 1, 2, 3, 4, 5, 6, 7, 8, 9, 10, or 11. The plant has a difference in the level of biomass as compared to the corresponding level of biomass of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463,464, 466, 467, 468, 470, 472, 474, 476, 478, 479,480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697. A plant produced from the plant cell has a difference in the level of biomass as compared to the corresponding level of biomass of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183,187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441,443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696, or a fragment thereof. A plant produced from the plant cell has a difference in the level of biomass as compared to the corresponding level of biomass of a control plant that does not comprise the exogenous nucleic acid. A transgenic plant comprising such a plant cell is also provided. Also provided is a plant biomass or seed product. The product comprises vegetative or embryonic tissue from a transgenic plant described herein.

Isolated nucleic acids are also provided. In one aspect, an isolated nucleic acid comprises a nucleotide sequence having 80% or greater sequence identity to the nucleotide sequence set forth in SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696. In another aspect, an isolated nucleic acid comprises a nucleotide sequence encoding a polypeptide having 80% or greater sequence identity to the amino acid sequence set forth in SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435,436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697.

In another aspect, methods of identifying a genetic polymorphism associated with variation in the level of biomass are provided. The methods include providing a population of plants, and determining whether one or more genetic polymorphisms in the population are genetically linked to the locus for a polypeptide selected from the group consisting of the polypeptides depicted in FIGS. 1-11 and functional homologs thereof. The correlation between variation in the level of biomass in a tissue in plants of the population and the presence of the one or more genetic polymorphisms in plants of the population is measured, thereby permitting identification of whether or not the one or more genetic polymorphisms are associated with such variation.

In another aspect, methods of making a plant line are provided. The methods include determining whether one or more genetic polymorphisms in a population of plants is associated with the locus for one or more of the polypeptides depicted in FIGS. 1-11 and functional homologs of such polypeptides. One or more plants in the population is identified in which the presence of at least one of the genetic polymorphism(s) is associated with variation in a biomass trait. The above-described steps can be performed in either order. One or more of the identified plants is then crossed with itself or a different plant to produce seed, and at least one progeny plant grown from such seed is crossed with itself or a different plant. The steps of selfing and outcrossing are repeated for an additional 0-5 generations to make a plant line in which the at least one polymorphism is present. The biomass trait can be yield of dry matter, and the plant population can be switchgrass plants.

This document also features a method of altering the level of biomass in a plant. The method includes modifying an endogenous biomass-modulating nucleic acid, the nucleic acid including a nucleotide sequence with an open reading frame having 80 percent or greater sequence identity to the nucleotide sequence selected from the group consisting of SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, and 696. The plant has a difference in the level of biomass as compared to the corresponding level of a control plant where the nucleic acid has not been modified. The modification can be effected by introducing a genetic modification in the locus comprising the nucleic acid. The method further can include selecting for plants having altered biomass.

In some embodiments, the endogenous nucleic acid encodes a polypeptide having 80 percent or greater sequence identity to an amino acid sequence selected from the group consisting of SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446,447, 448, 449, 450, 452, 453, 454, 455, 456, 457, 459, 461, 463, 464, 466, 467, 468, 470, 472, 474, 476, 478, 479, 480, 482, 483, 484,486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, and 697.

In some embodiments, the endogenous nucleic acid comprises a nucleotide sequence with an open reading frame having 90 percent or greater sequence identity to the nucleotide sequence selected from the group consisting of SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, and 696.

In some embodiments, the endogenous nucleic acid comprises a nucleotide sequence with an open reading frame having 95 percent or greater sequence identity to the nucleotide sequence selected from the group consisting of SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175,177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, and 696.

This document also features a method of producing a plant. The method includes growing a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-11, and wherein the plant has a difference in the level of biomass as compared to the corresponding level of a control plant where the nucleic acid has not been modified.

In another aspect, this document features a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-11, and wherein a plant produced from the plant cell has a difference in the level of biomass as compared to the corresponding level of a control plant where the nucleic acid has not been modified.

This document also features a plant cell containing a modified biomass-modulating endogenous nucleic acid. The nucleic acid comprising a nucleotide sequence with an open reading frame having 80 percent or greater sequence identity to the nucleotide sequence selected from the group consisting of SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, and 696. A plant produced from the plant cell has a difference in the level of biomass as compared to the corresponding level of a control plant where the nucleic acid has not been modified.

In a plant cell described herein, the endogenous nucleic acid can encode a polypeptide having 80 percent or greater sequence identity to an amino acid sequence selected from the group consisting of SEQ ID NO: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, and 697, and wherein a plant produced from the plant cell has a difference in the level of biomass as compared to the corresponding level of a control plant where the nucleic acid has not been modified.

In another aspect, this document features a method of modulating the level of biomass in a plant. The method includes introducing into a plant cell an exogenous nucleic acid, the exogenous nucleic acid encoding a polypeptide having E.C. 2.6.1.83 activity.

A plant cell also is featured that includes an exogenous nucleic acid, where the exogenous nucleic acid encodes a polypeptide having E.C. 2.6.1.83 activity, and wherein a plant produced from the plant cell has a difference in the level of biomass as compared to the corresponding level of a control plant that does not comprise the nucleic acid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF THE DRAWINGS

FIG. 1 is an alignment of the amino acid sequence of CW00733 corresponding to Ceres Clone: 1384304 (SEQ ID NO: 554) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of the amino acid sequence of CW00319 corresponding to Ceres Annot: 544549 (SEQ ID NO: 263) with homologous and/or orthologous amino acid sequences.

FIG. 3 is an alignment of the amino acid sequence of CW00710 corresponding to Ceres Annot: 1355066 (SEQ ID NO: 117) with homologous and/or orthologous amino acid sequences.

FIG. 4 is an alignment of the amino acid sequence of CW00628 corresponding to an antisense sequence of Os01g58420, (SEQ ID NO: 1) with homologous and/or orthologous amino acid sequences.

FIG. 5 is an alignment of the amino acid sequence of CW00297 corresponding to Ceres Clone: 625057 (SEQ ID NO: 645) with homologous and/or orthologous amino acid sequences.

FIG. 6 is an alignment of the amino acid sequence of CW00604 corresponding to Ceres Clone:1356785 (SEQ ID NO: 253) with homologous and/or orthologous amino acid sequences.

FIG. 7 is an alignment of the amino acid sequence of CW00564 corresponding to Ceres Clone:638126 (SEQ ID NO: 323) with homologous and/or orthologous amino acid sequences.

FIG. 8 is an alignment of the amino acid sequence of CW00010 corresponding to Ceres Clone: 26006 (SEQ ID NO: 595) with homologous and/or orthologous amino acid sequences.

FIG. 9 is an alignment of the amino acid sequence of CW00469 corresponding to Ceres Clone: 4831 (SEQ ID NO: 77) with homologous and/or orthologous amino acid sequences.

FIG. 10 is an alignment of the amino acid sequence of CW00536 corresponding to Ceres Annot: 847799 (SEQ ID NO:209) with homologous and/or orthologous amino acid sequences.

FIG. 11 is an alignment of the amino acid sequence of CW00191 corresponding to Ceres Annot: 878355 (SEQ ID NO: 426) with homologous and/or orthologous amino acid sequences.

DETAILED DESCRIPTION

The invention features methods and materials related to modulating biomass levels in plants. In some embodiments, the plants may also have modulated levels of, for example, lignin, modified root architecture, modified herbicide resistance, modified carotenoid biosynthesis, or modulated cell wall content. The methods can include transforming a plant cell with a nucleic acid encoding a biomass-modulating polypeptide, wherein expression of the polypeptide results in a modulated level of biomass. Plant cells produced using such methods can be grown to produce plants having an increased or decreased biomass. Such plants, and the seeds of such plants, may be used to produce, for example, biomass having an increased value as a biofuel feedstock.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds or millions of other nucleic acids within, for example, cDNA libraries, genomic libraries, or gel slices containing a genomic DNA restriction digest, is not to be considered an isolated nucleic acid.

"Modulation" of the level of biomass refers to the change in the level of the biomass that is observed as a result of expression of, or transcription from, an exogenous nucleic acid in a plant cell and/or plant. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include biomass-modulating polypeptides. Biomass-modulating polypeptides can be effective to modulate biomass levels when expressed in a plant or plant cell. Such polypeptides typically contain at least one domain indicative of biomass-modulating polypeptides, as described in more detail herein. biomass-modulating polypeptides typically have an HMM bit score that is greater than 65 as described in more detail herein. In some embodiments, biomass-modulating polypeptides have greater than 80% identity to SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114,115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476,478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697, as described in more detail herein.

A. Domains Indicative of Biomass-Modulating Polypeptides

A biomass-modulating polypeptide can contain a Dof domain-zinc finger (zf-Dof), which is predicted to be characteristic of a biomass-modulating polypeptide. SEQ ID NO: 263 sets forth the amino acid sequence of an *Arabidopsis* clone, identified herein as Ceres Annot: 544549 (SEQ ID NO: 262), that is predicted to encode a polypeptide containing a Dof domain-zinc finger. For example, a biomass-modulating polypeptide can comprise a Dof domain-zinc finger having 60 percent or greater sequence identity to residues 130 to 192 of SEQ ID NO: 263. In some embodiments, a biomass-modulating polypeptide can comprise a Dof domain-zinc finger having 60 percent or greater sequence identity to the Dof domain-zinc finger of one or more of the polypeptides set forth in SEQ ID NOs: 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, or 321. The Dof domain-zinc fingers of such sequences are set forth in the Sequence Listing. Zinc finger (Znf) domains are relatively small protein motifs that bind one or more zinc atoms, and which usually contain multiple finger-like protrusions that make tandem contacts with their target molecule. They were first identified as a DNA-binding motif in transcription factor TFIIIA from *Xenopus laevis*, however they are now recognized to bind DNA, RNA, protein and/or lipid substrates. Their binding properties depend on the amino acid sequence of the finger domains and of the linker between fingers, as well as on the higher-order structures and the number of fingers. Znf domains are often found in clusters, where fingers can have different binding specificities. There are many superfamilies of Znf motifs, varying in both sequence and structure. They display considerable versatility in binding modes, (e.g. some bind DNA, others protein), suggesting that Znf motifs are stable scaffolds that have evolved specialized functions. For example, Znf-containing proteins function in gene transcription, translation, mRNA trafficking, cytoskeleton organization, epithelial development, cell adhesion, protein folding, chromatin remodeling and zinc sensing, to name but a few. Zinc-binding motifs are stable structures, and they rarely undergo conformational changes upon binding their target. DOF 1.3 orthologs may contain Dof domain-zinc fingers.

A biomass-modulating polypeptide can contain a phytochelatin synthetase-like domain, which is predicted to be characteristic of a biomass-modulating polypeptide. SEQ ID NO: 117 sets forth the amino acid sequence of an *Arabidopsis* clone, identified herein as Ceres Annot: 1355066 (SEQ ID NO: 116) that is predicted to encode a polypeptide containing a phytochelatin synthetase-like domain domain. For example, a biomass-modulating polypeptide can comprise a phytochelatin synthetase-like domain domain having 60 percent or greater sequence identity to residues 44 to 208 of SEQ ID NO: 117. In some embodiments, a biomass-modulating polypeptide can comprise a phytochelatin synthetase-like domain domain having 60 percent or greater sequence identity to the phytochelatin synthetase-like domain domain of one or more of the polypeptides set forth in SEQ ID NOs: 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, or 207. The phytochelatin synthetase-like domain domains of such sequences are set forth in the Sequence Listing. Phytochelatin synthase-like protein may be an enzyme responsible for the synthesis of heavy-metal-binding peptides (phytochelatins) from glutathione and related thiols. The enzyme typically catalyses the deglycination of a GSH donor molecule. The enzyme typically contains a catalytic triad of cysteine, histidine and aspartate residues.

A biomass-modulating polypeptide can contain an AP2 domain, which is predicted to be characteristic of a biomass-modulating polypeptide. SEQ ID NO: 1 sets forth the amino acid sequence of an *Oryza sativa* clone, identified herein as Os01g58420 that is predicted to encode a polypeptide containing a AP2 domain. For example, a biomass-modulating polypeptide can comprise a AP2 domain having 60 percent or greater sequence identity to residues 32 to 83 of SEQ ID NO: 1. In some embodiments, a biomass-modulating polypeptide can comprise a AP2 domain having 60 percent or greater sequence identity to the AP2 domain of one or more of the polypeptides set forth in SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, or 75. The AP2 domains of such sequences are set forth in the Sequence Listing. In some embodiments, an antisense sequence is expressed in a plant to modulate biomass as described herein. For example, an antisense nucleic acid sequence of Os01g58420 such as SEQ ID NO: 678, can be expressed in a plant to modulate biomass. AP2 domain amino acid residues can bind to DNA and are typically found in transcription factor proteins.

A biomass-modulating polypeptide can contain an Aminotransferase class I and II domain, which is predicted to be characteristic of a biomass-modulating polypeptide. SEQ ID NO: 645 sets forth the amino acid sequence of an *Glycine max* clone, identified herein as Ceres Clone:625057 (SEQ ID NO: 644), that is predicted to encode a polypeptide containing a Aminotransferase class I and II domain. For example, a biomass-modulating polypeptide can comprise an Aminotransferase class I and II domain having 60 percent or greater sequence identity to residues 88 to 453 of SEQ ID NO: 645. In some embodiments, a biomass-modulating polypeptide can comprise a Aminotransferase class I and II domain having 60 percent or greater sequence identity to the Aminotransferase class I and II domain of one or more of the polypeptides set forth in SEQ ID NOs: 645, 647, 649, 651, 652, 653, 655, 657, 659, 660, 662, 664, 666, 667, 669, 670, 671, 672, 673, 674, 675, 676, 677, or 689. The Aminotransferase class I and II domains of such sequences are set forth in the Sequence Listing. Aminotransferases share certain mechanistic features with other pyridoxal-phosphate dependent enzymes, such as the covalent binding of the pyridoxal-phosphate group to a lysine residue. On the basis of sequence similarity, these various enzymes can be grouped into class I and class II. Examples of polypeptides comprising Aminotransferases class I and II domains include LL-DAP polypeptides (EC 2.6.1.83) (Watanabe et al., Mechanism of Substrate Recognition and PLP-induced Conformational Changes in LL-Diaminopimelate aminotransferase from *Arabidopsis thaliana*. *J. Mol. Biol*. 384, 1314-1329 (2008)). LL-DAP catalyzes the interconversion of LL-2,6-diaminoheptanedioate and 2-oxoglutarate to (S)-2,3,4,5-tetrahydropyridine-2,6-dicarboxylate, L-glutamate, and water.

A biomass-modulating polypeptide can contain a My-like DNA-binding domain, which is predicted to be characteristic of a biomass-modulating polypeptide. SEQ ID NO: 323 sets forth the amino acid sequence of an *Glycine max* clone, identified herein as Ceres Clone: 638126 (SEQ ID NO: 321), that is predicted to encode a polypeptide containing a Myb-like DNA-binding domain. For example, a biomass-modulating polypeptide can comprise a Myb-like DNA-binding domain having 60 percent or greater sequence identity to residues 13 to 62 of SEQ ID NO: 323. In some embodiments, a biomass-modulating polypeptide can comprise a Myb-like DNA-binding domain having 60 percent or greater sequence identity to the Myb-like DNA-binding domain of one or more of the polypeptides set forth in SEQ ID NOs: 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, or 424. The Myb-like DNA-binding domains of such sequences are set forth in the Sequence Listing. The Myb-like DNA-binding domain family contains the DNA binding domains from Myb proteins, as well as the SANT domain family.

A biomass-modulating polypeptide can contain an alpha/beta hydrolase fold domain, which is predicted to be characteristic of a biomass-modulating polypeptide. SEQ ID NO: 595 sets forth the amino acid sequence of an *Arabidopsis* clone, identified herein as Ceres Clone: 26006 (SEQ ID NO: 594), that is predicted to encode a polypeptide containing an alpha/beta hydrolase fold domain. For example, a biomass-modulating polypeptide can comprise an alpha/beta hydrolase fold domain having 60 percent or greater sequence identity to residues 35 to 257 of SEQ ID NO: 595. In some embodiments, a biomass-modulating polypeptide can comprise an alpha/beta hydrolase fold domain having 60 percent or greater sequence identity to the alpha/beta hydrolase fold domain of one or more of the polypeptides set forth in SEQ ID NOs: 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, or 691. The alpha/beta hydrolase fold domains of such sequences are set forth in the Sequence Listing. The alpha/beta hydrolase fold is common to a number of hydrolytic enzymes of widely differing phylogenetic origin and catalytic function. The core of each enzyme is an alpha/beta-sheet (rather than a barrel), containing 8 strands connected by helices. The enzymes are believed to have diverged from a common ancestor, preserving the arrangement of the catalytic residues. All have a catalytic triad, the elements of which are borne on loops, which are the best conserved structural features of the fold.

A biomass-modulating polypeptide can contain a Rapid Alkalinization Factor (RALF) domain, which is predicted to be characteristic of a biomass-modulating polypeptide. SEQ ID NO: 77 sets forth the amino acid sequence of an *Arabidopsis* clone, identified herein as Ceres Clone: 4831 (SEQ ID NO: 76), that is predicted to encode a polypeptide containing a RALF domain. For example, a biomass-modulating polypeptide can comprise a RALF domain having 60 percent or greater sequence identity to residues 57 to 129 of SEQ ID NO: 77. In some embodiments, a biomass-modulating polypeptide can comprise a RALF domain having 60 percent or greater sequence identity to the RALF domain of one or more of the polypeptides set forth in SEQ ID NOs: 77, 79, 81, 82, 84, 86, 87, 88, 90, 92, 94, 96, 98, 100, 102, 104, 106, 108, 110, 112, 114, or 115. The RALF domains of such sequences are set forth in the Sequence Listing. RALF domains are typically found in 5-kDa ubiquitous polypeptides in plants, which have been reported to play a role in the arrest of root growth and development in some plants.

A biomass-modulating polypeptide can contain a DUF640 domain, which is predicted to be characteristic of a biomass-modulating polypeptide. SEQ ID NO: 209 sets forth the amino acid sequence of an *Arabidopsis* clone, identified herein as Ceres Annot: 847799 (SEQ ID NO: 208), that is predicted to encode a polypeptide containing a DUF640 domain. For example, a biomass-modulating polypeptide can comprise a DUF640 domain having 60 percent or greater sequence identity to residues 19 to 152 of SEQ ID NO: 209. In some embodiments, a biomass-modulating polypeptide can comprise a DUF640 domain having 60 percent or greater sequence identity to the DUF640 domain of one or more of the polypeptides set forth in SEQ ID NOs: 209, 210, 212, 214, 216, 218, 220, 222, 224, 226, 228, 230, 232, 234, 236, 238, 239, 241, 242, 243, 244, 245, 246, 247, 248, 249, 250, or 251. The DUF640 domains of such sequences are set forth in the Sequence Listing.

A biomass-modulating polypeptide can contain a PTR2 POT family domain, which is predicted to be characteristic of a biomass-modulating polypeptide. SEQ ID NO: 426 sets forth the amino acid sequence of an *Arabidopsis* clone, identified herein as Ceres Annot: 878355 (SEQ ID NO: 425), that is predicted to encode a polypeptide containing a PTR2 POT family domain. For example, a biomass-modulating polypeptide can comprise a PTR2 POT family domain having 60 percent or greater sequence identity to residues 100 to 509 of SEQ ID NO: 426. In some embodiments, a biomass-modulating polypeptide can comprise a PTR2 POT family domain having 60 percent or greater sequence identity to the PTR2 POT family domain of one or more of the polypeptides set forth in SEQ ID NOs: 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 693, 695, or 697. The PTR2 POT family domains of such sequences are set forth in the Sequence Listing. The transport of peptides into cells is a well-documented biological phenomenon which is accomplished by specific, energy-dependent transporters found in a number of organisms as diverse as bacteria and humans. The PTR family of proteins is distinct from the ABC-type peptide transporters and was uncovered by sequence analyses of a number of recently discovered peptide transport proteins. These proteins seem to be mainly involved in the intake of small peptides with the concomitant uptake of a proton. In some embodiments, a POT protein as described herein can comprise an N-terminus signal peptide. In some embodiments, the signal peptide may be specific for a plasma membrane. In some embodiments, the signal peptide may be specific for a endoplasmic reticulum membrane or a chloroplast membrane. Examples of signal peptides are shown in the Sequence Listing of the application. Bioinformatics techniques can be employed to predict the presence and type of transit peptides. These approaches do not rely exclusively on sequence similarity. Because orthologous proteins more often have the same localization, the degree of sequence similarity needed to infer co-localization is higher than for similar three-dimensional structure, and isoforms of the same protein may have different localization. WoLF PSORT can be used to predict signal peptides (Horton et al., 2007 "WoLF PSORT: Protein Localization Predictor", Nucleic Acids Research, doi: 10.1093/nar/gkm259, 2007; Horton et al., 2006 "Protein Subcellular Localization Prediction with WoLF PSORT", Proceedings of the 4th Annual Asia Pacific Bioinformatics Conference APBC06, Taipei, Taiwan. pp. 39-48, 2006). Examples of signal peptides from sequences in the public domain can be obtained from a WoLF PSORT analysis of a sequence which provides numerous orthologous signal peptides.

In eukaryotic organisms, there are several types of signal peptides and related sorting signals all of which involve membrane translocation and/or insertion. Typically, signal peptides specific for the endoplasmic reticulum (ER) are co-translational, whereas signal peptides specific for the mitochondria or chloroplast are post-translational, but unfolded by chaperones. For example, an N-terminal signal with variable length hydrophobic section, causes proteins to be co-translationally transported through or into the endoplasmic reticulum membrane. N-terminal signals are mostly independent of carrier proteins. Such signal peptides are typically interchangeable between different proteins, are typically cleaved, and are typically limited to about the first 90 amino acid residues. Cleavage, presence on N-terminal, and co-translational recognition make signal peptides typically orthogonal to protein function, but this is a general relationship. In some embodiments, a POT protein as described herein can comprise a C-terminal sorting signal. Examples of C-terminal sorting signals include, but are not limited to, KDEL (soluble) or KKXX (membrane protein) signal for ER retention, SKL for peroxisomal targeting (soluble), NPIR for vacuole, and LPXTG for bacterial cell wall. In some embodiments, a POT protein as described herein can comprise an internal sorting signal. Such signals include nuclear localization signals that occur on the surface of a folded protein but can be anywhere on the 1-dimensional sequence. In some embodiments, a POT protein as described herein can comprise an N-terminus signal peptide that is about 95, 90, 85, 80, 75, 70, 65, 60, 55, 50, 45, 40, 35, 30, 25, 20, 15, 10, or 5 amino acids in length beginning from the N-terminus of said POT protein. In some embodiments, a POT protein as described herein is lacking all or part of an N-terminus signal peptide. In some embodiments, a POT protein as described herein can have an N-terminus signal peptide removed and replaced with a different an N-terminus signal peptide. For example, one skilled in the art can remove or synthesize a sequence without the 45 N-terminus amino acids of SEQ ID NO: (426) and add, through fusion techniques or through synthesis, another signal peptide with specificity for the same or a different target membrane.

In some embodiments, a biomass-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the biomass-modulating activity of a truncated polypeptide. In some embodiments, a truncated polypeptide is a dominant negative polypeptide. Expression in a plant of such a truncated polypeptide confers a difference in the level of biomass of a plant as compared to the corresponding level of a control plant that does not comprise the truncation.

B. Functional Homologs Identified by Reciprocal BLAST

In some embodiments, one or more functional homologs of a reference biomass-modulating polypeptide defined by one or more of the Pfam descriptions indicated above are suitable for use as biomass-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a biomass-modulating polypeptide, or by combining domains from the coding sequences for different naturally-occurring biomass-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass-modulating polypeptides. Sequence analysis can involve BLAST, Reciprocal BLAST, or PSI-BLAST analysis of nonredundant databases using a biomass-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a biomass-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in biomass-modulating polypeptides, e.g., conserved functional domains.

Conserved regions can be identified by locating a region within the primary amino acid sequence of a biomass-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
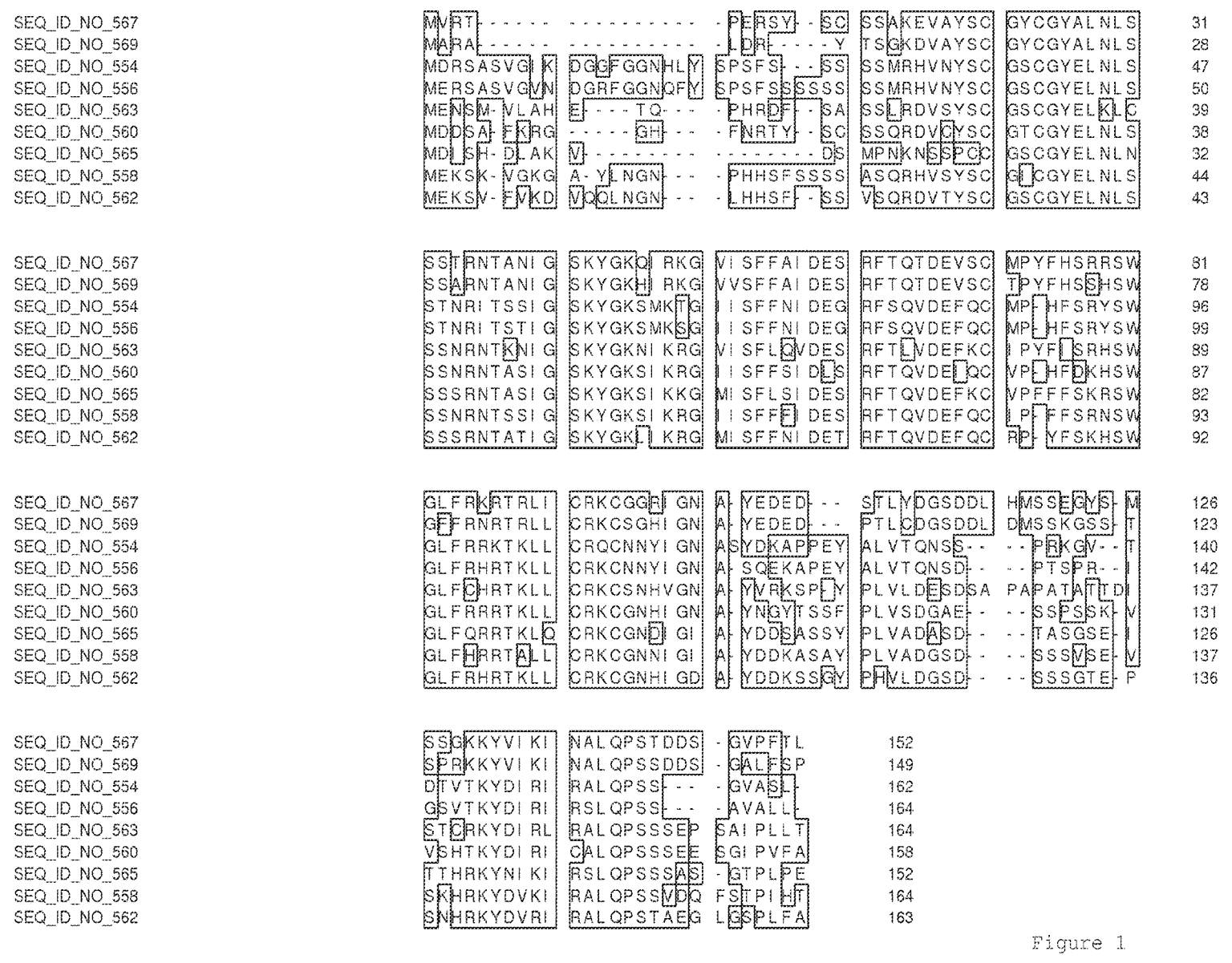

Examples of amino acid sequences of functional homologs of the polypeptide set forth in SEQ ID NO: 554 are provided in FIG. 1 and in the Sequence Listing. Such functional homologs include, for example, CeresAnnot:564098 (SEQ ID NO: 556), CeresAnnot:1443290 (SEQ ID NO: 558), CeresClone:1042157 (SEQ ID NO: 560), CeresClone:1919714 (SEQ ID NO: 562), GI:157336039 (SEQ ID NO: 563), CeresAnnot:8454153 (SEQ ID NO: 565), CeresAnnot:1722302 (SEQ ID NO: 567), CeresAnnot:8733140 (SEQ ID NO: 569), CeresAnnot:1452096 (SEQ ID NO:

571), CeresClone:1645639 (SEQ ID NO: 573), GI:157344920 (SEQ ID NO: 574), GI:115440865 (SEQ ID NO: 575), CeresClone:340925 (SEQ ID NO: 577), CeresAnnot:8669404 (SEQ ID NO: 579), CeresClone:100028078 (SEQ ID NO: 581), CeresAnnot:1503869 (SEQ ID NO: 583), CeresAnnot:1525651 (SEQ ID NO: 585), CeresClone:2031281 (SEQ ID NO: 587), CeresClone:483742 (SEQ ID NO: 589), CeresClone:100802111 (SEQ ID NO: 591), or CeresClone:1460255 (SEQ ID NO: 593). In some cases, a functional homolog of SEQ ID NO: 554 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 554.

Figure 2:
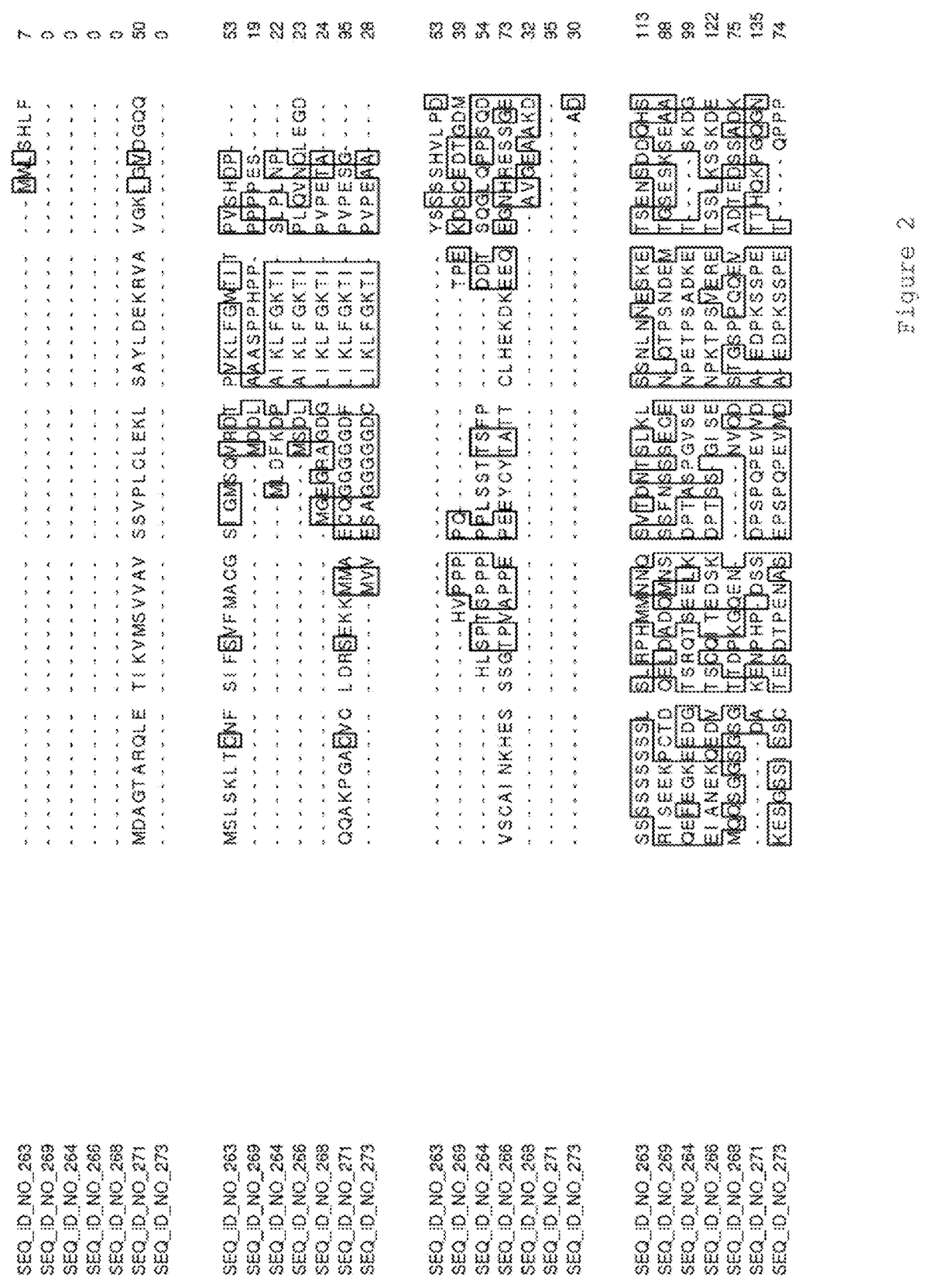
Figure 2:
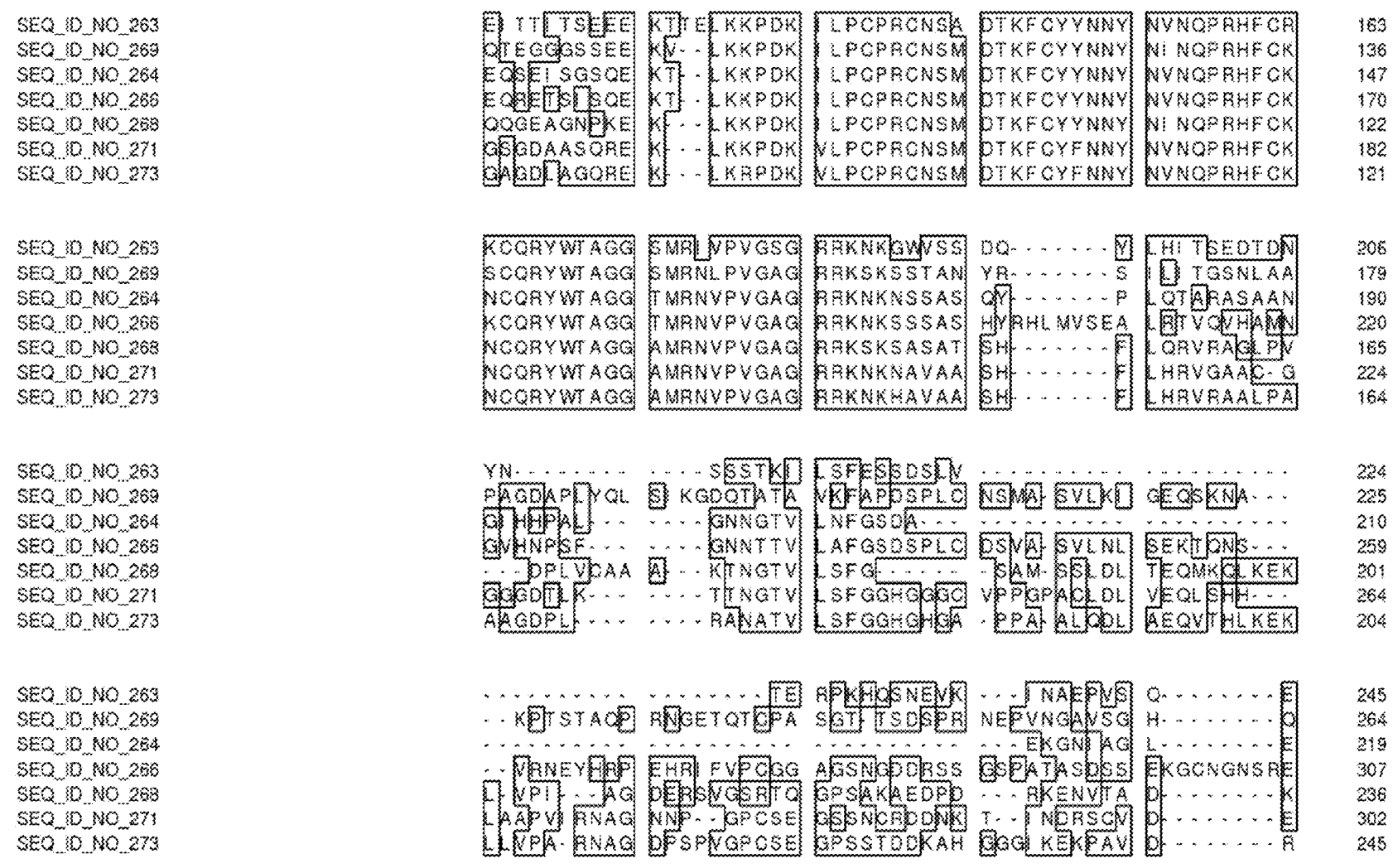
Figure 2:
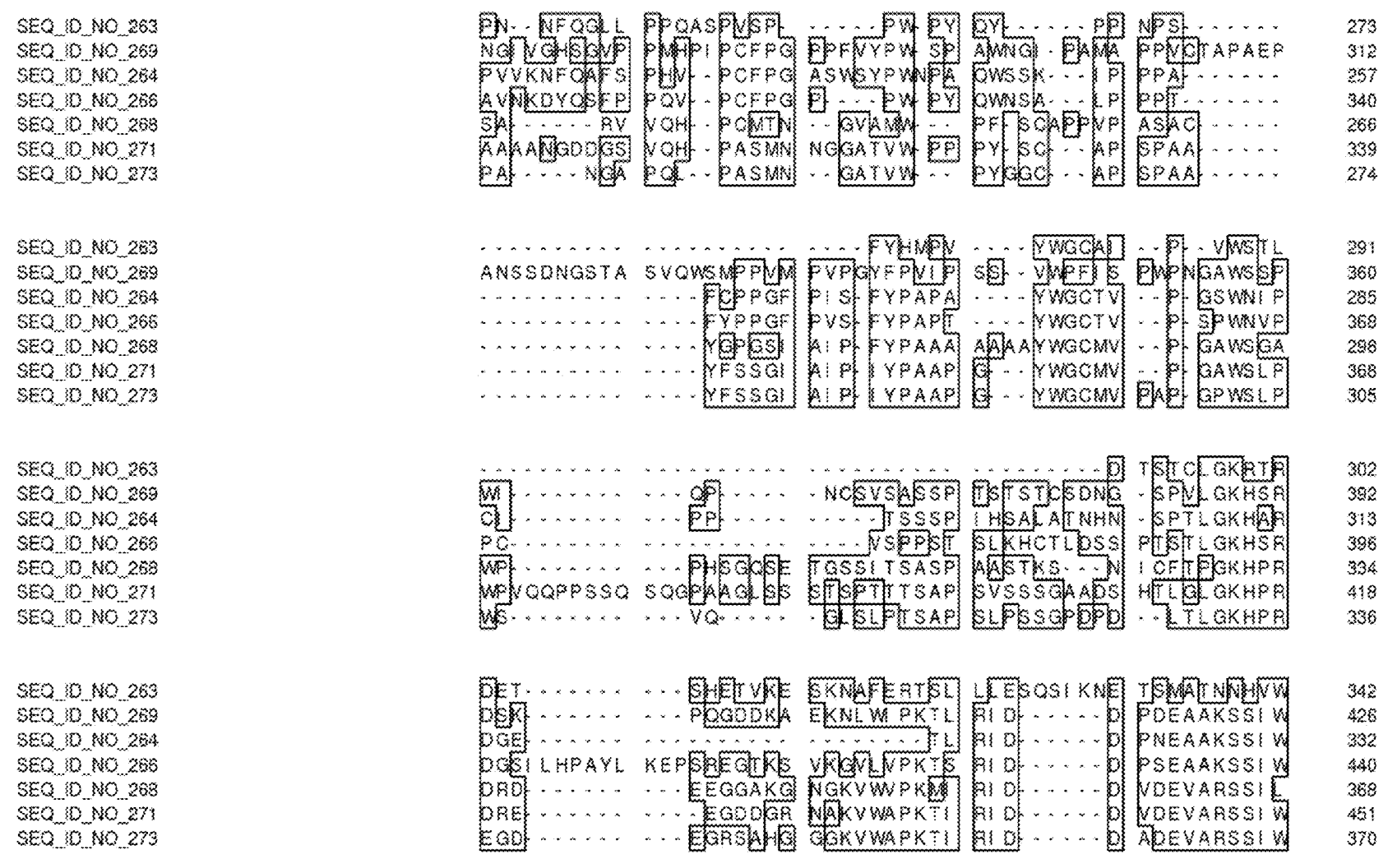
Figure 2:
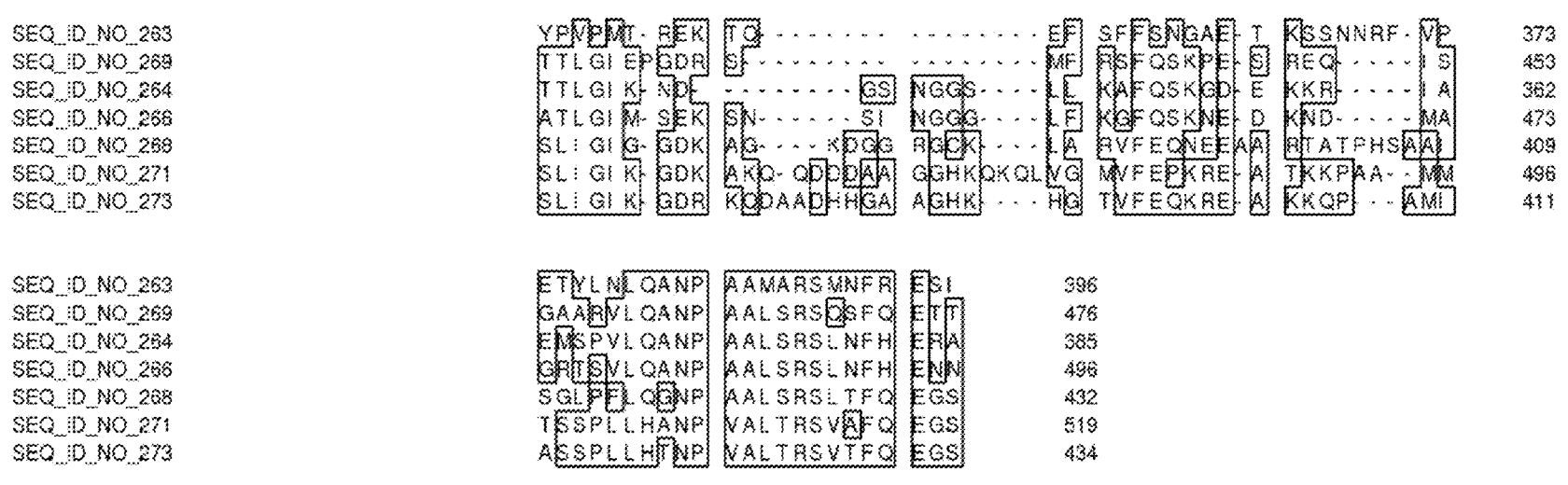

Examples of amino acid sequences of functional homologs of the polypeptide set forth in SEQ ID NO: 263 are provided in FIG. 2 and in the Sequence Listing. Such functional homologs include, for example, GI:157355009 (SEQ ID NO: 264), CeresAnnot:1464457 (SEQ ID NO: 266), CeresClone:1584660 (SEQ ID NO: 268), GI:115474149 (SEQ ID NO: 269), CeresAnnot:8636233 (SEQ ID NO:271), CeresClone:1777035 (SEQ ID NO: 273), CeresClone:1990929 (SEQ ID NO: 275), GI:194692166 (SEQ ID NO: 276), CeresAnnot:1458507 (SEQ ID NO: 278), GI:147780712 (SEQ ID NO:279), CeresAnnot:8642924 (SEQ ID NO: 281), GI:115451001 (SEQ ID NO: 282), AAF87041 (SEQ ID NO: 283), CeresClone:1573856 (SEQ ID NO: 285), CeresAnnot:1476818 (SEQ ID NO:287), CeresAnnot:1450024 (SEQ ID NO: 289), CeresAnnot:1503065 (SEQ ID NO: 291), GI:147866358 (SEQ ID NO: 292), CeresClone:230073 (SEQ ID NO: 294), (SEQ ID NO:295), (SEQ ID NO: 296), GI:78708599 (SEQ ID NO: 297), GI:15451553 (SEQ ID NO: 298), GI: 125542572 (SEQ ID NO: 299), GI:157342426 (SEQ ID NO:300), CeresAnnot:538622 (SEQ ID NO: 302), CeresAnnot:8460661 (SEQ ID NO: 304), GI:15983797 (SEQ ID NO: 305), GI: 115435804 (SEQ ID NO: 306), CeresClone:1599579 (SEQ ID NO:308), CeresAnnot:1469831 (SEQ ID NO: 310), GI:9758342 (SEQ ID NO: 311), GI:21536859 (SEQ ID NO: 312), CeresClone:113639 (SEQ ID NO: 314), GI:15232818 (SEQ ID NO: 315), CeresClone:1571328 (SEQ ID NO: 317), CeresClone:1868988 (SEQ ID NO: 319), GI:1669341 (SEQ ID NO: 320), or GI:157359317 (SEQ ID NO: 321). In some cases, a functional homolog of SEQ ID NO: 263 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 263.

Figure 3:
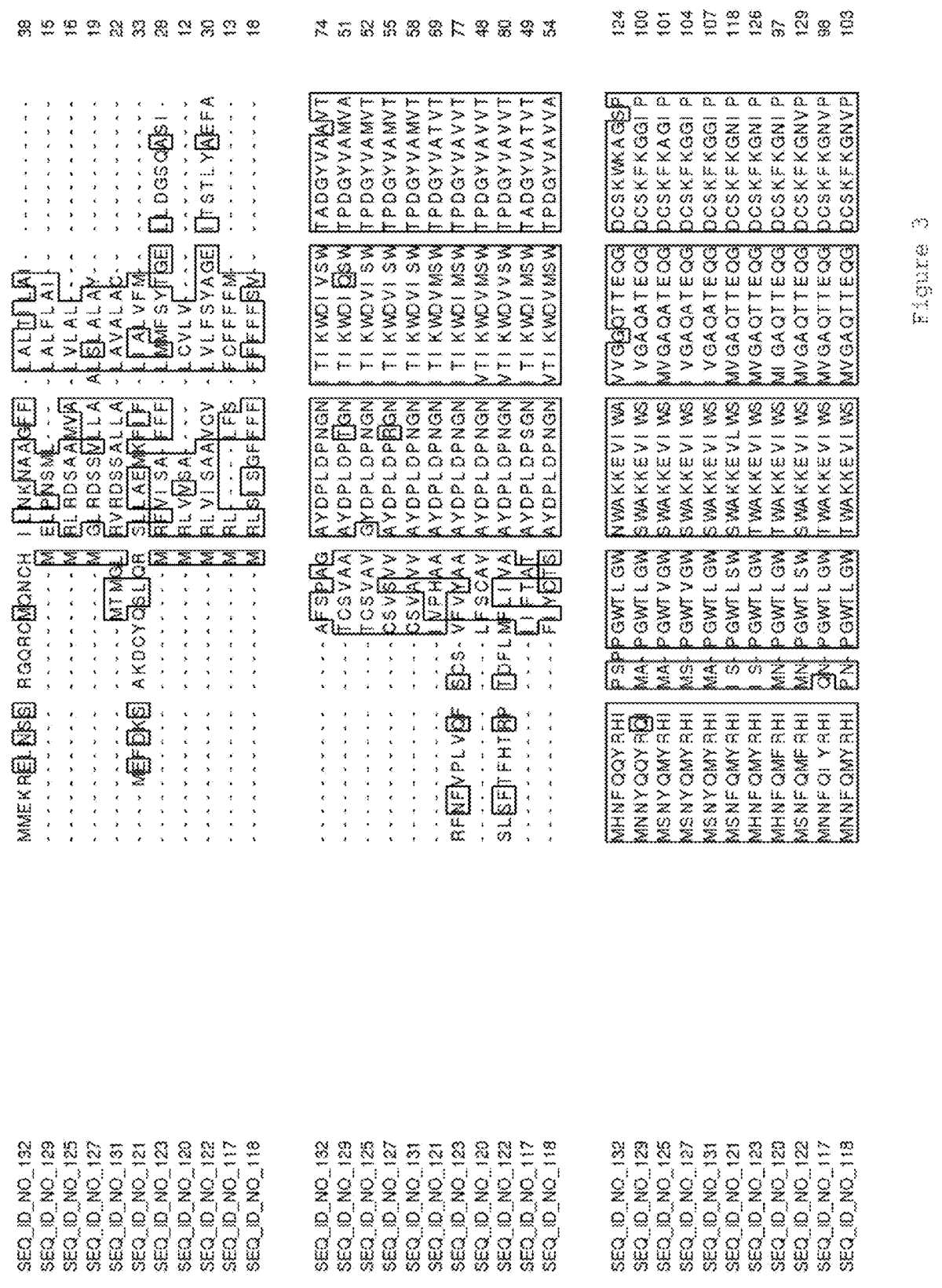
Figure 3:
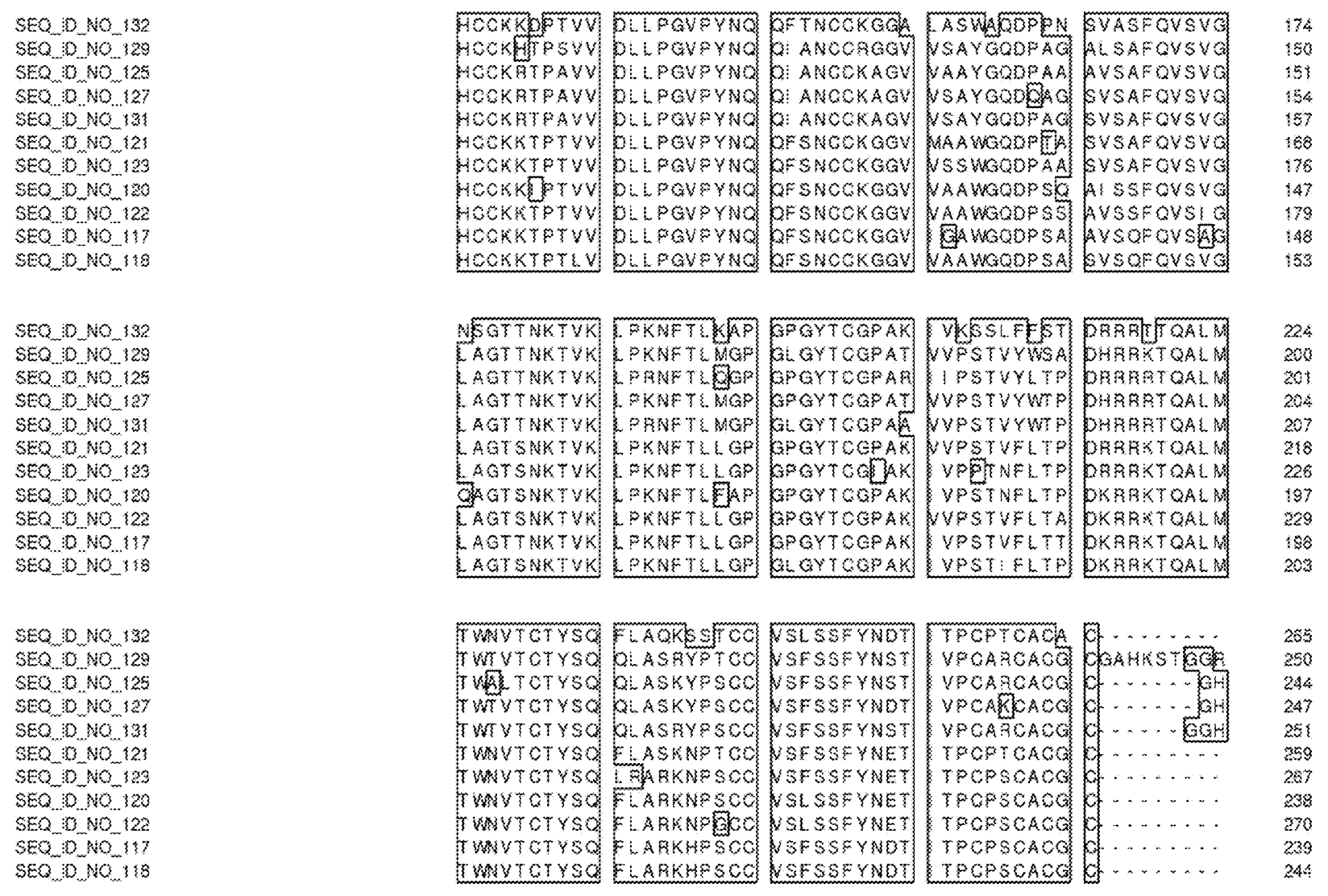
Figure 3:
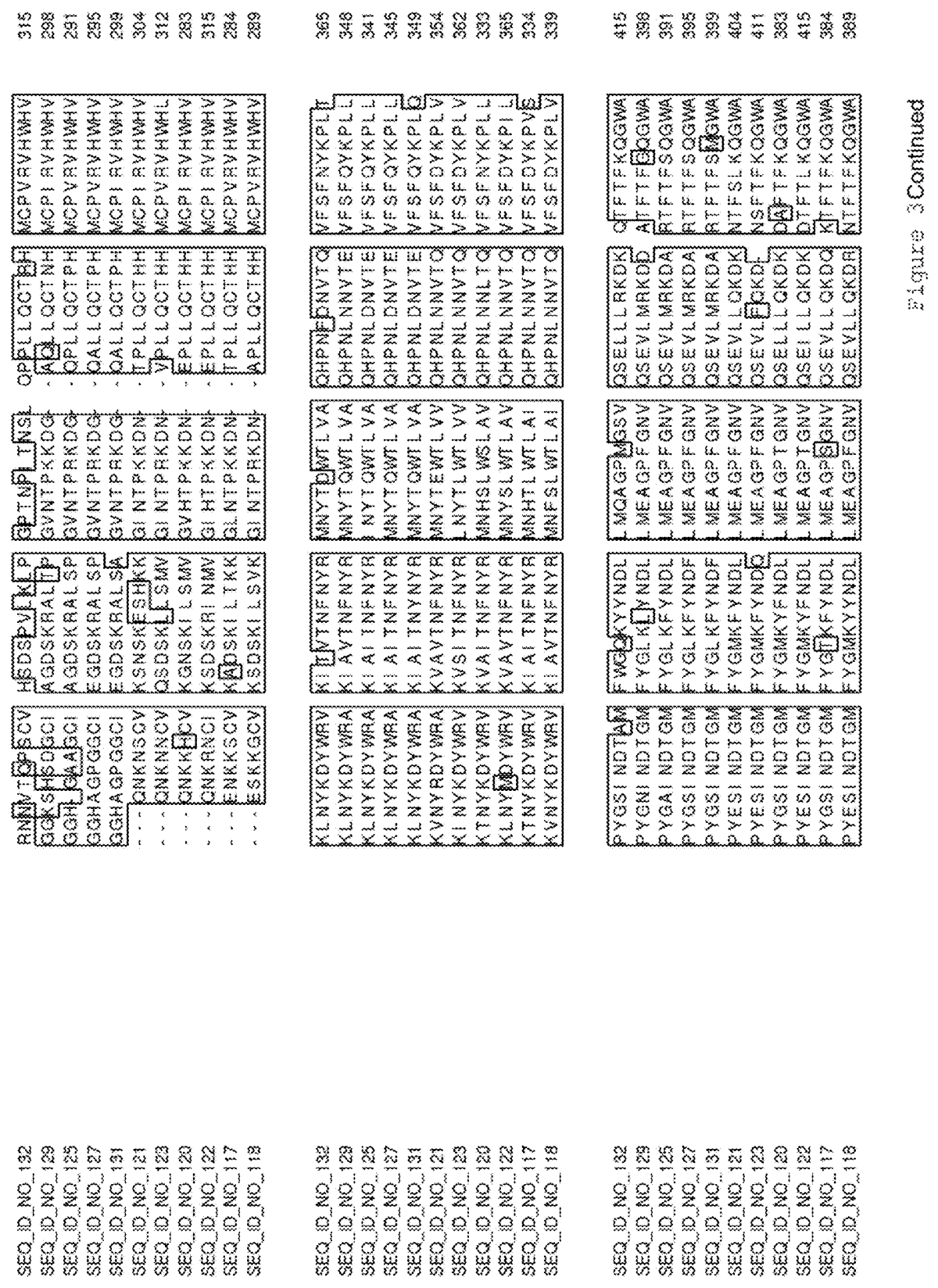

Examples of amino acid sequences of functional homologs of the polypeptide set forth in SEQ ID NO: 117 are provided in FIG. 3 and in the Sequence Listing. Such functional homologs include, for example, GI:90657534 (SEQ ID NO: 118), CeresClone:1237946 (SEQ ID NO: 120), GI:118488472 (SEQ ID NO: 121), GI:38194917 (SEQ ID NO: 122), GI:157341292 (SEQ ID NO: 123), CeresClone:1957107 (SEQ ID NO: 125), CeresAnnot:8640603 (SEQ ID NO: 127), CeresClone:829440 (SEQ ID NO: 129), CeresClone:285169 (SEQ ID NO: 131), GI:116790012 (SEQ ID NO: 132), GI:157356290 (SEQ ID NO: 133), CeresAnnot:1450186 (SEQ ID NO: 135), CeresClone:1804732 (SEQ ID NO: 137), CeresClone:1781794 (SEQ ID NO: 139), CeresAnnot:8656625 (SEQ ID NO: 141), GI:162462515 (SEQ ID NO: 142), CeresClone:570485 (SEQ ID NO: 144), GI:125586664 (SEQ ID NO: 145), GI:116788824 (SEQ ID NO: 146), GI:115453531 (SEQ ID NO: 147), CeresClone:17250 (SEQ ID NO: 149), CeresAnnot:1363625 (SEQ ID NO: 151), GI:75133694 (SEQ ID NO: 152), GI:147780878 (SEQ ID NO: 153), GI:157341291 (SEQ ID NO: 154), GI:38194916 (SEQ ID NO: 155), GI:157356291 (SEQ ID NO: 156), CeresClone:1883580 (SEQ ID NO: 158), CeresClone:1848658 (SEQ ID NO: 160), CeresAnnot:1450185 (SEQ ID NO: 162), GI:13477083 (SEQ ID NO: 163), GI:115463639 (SEQ ID NO: 164), CeresClone:98007 (SEQ ID NO: 166), CeresAnnot:1326475 (SEQ ID NO: 168), GI:115473243 (SEQ ID NO: 169), CeresAnnot:870466 (SEQ ID NO: 171), CeresClone:1806851 (SEQ ID NO: 173), GI:75133695 (SEQ ID NO: 174), CeresClone:1788775 (SEQ ID NO: 176), CeresClone:1546455 (SEQ ID NO: 178), CeresClone:1902642 (SEQ ID NO: 180), CeresAnnot:8632643 (SEQ ID NO: 182), CeresClone:236876 (SEQ ID NO: 184), GI:90657629 (SEQ ID NO: 185), GI:30090032 (SEQ ID NO: 186), CeresAnnot:8640602 (SEQ ID NO: 188), GI:115453533 (SEQ ID NO: 189), GI:162462330 (SEQ ID NO: 190), GI:38230578 (SEQ ID NO: 191), CeresAnnot:8632641 (SEQ ID NO: 193), GI:168016456 (SEQ ID NO: 194), GI:125532513 (SEQ ID NO: 195), GI:157354382 (SEQ ID NO: 196), CeresAnnot:1481980 (SEQ ID NO: 198), CeresAnnot:1535466 (SEQ ID NO: 200), CeresAnnot:1297618 (SEQ ID NO: 202), GI:119040466 (SEQ ID NO: 203), GI:116310381 (SEQ ID NO: 204), CeresAnnot:8702104 (SEQ ID NO: 206), or GI:157340500 (SEQ ID NO: 207). In some cases, a functional homolog of SEQ ID NO: 117 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 117.

Figure 4:
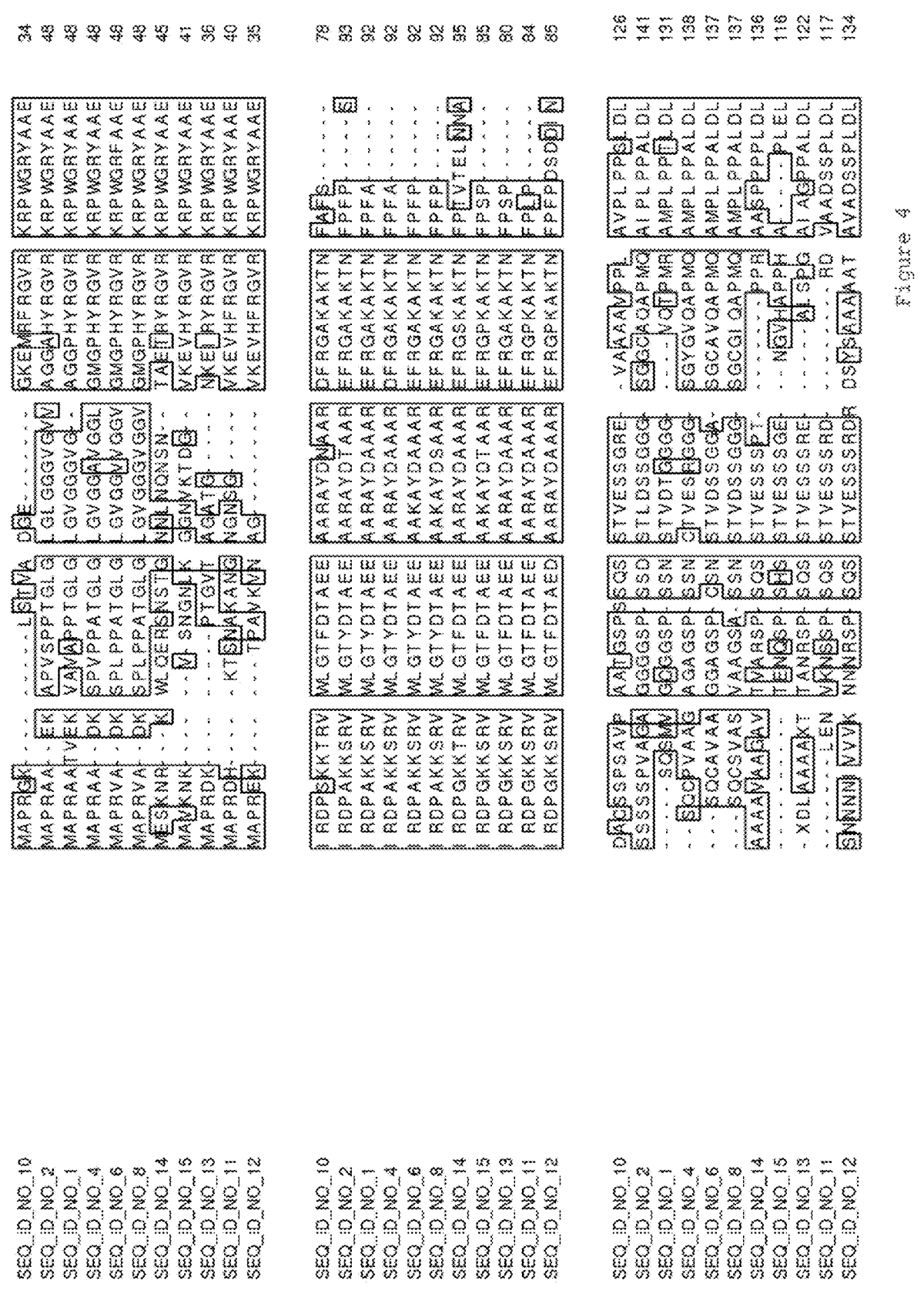
Figure 4:
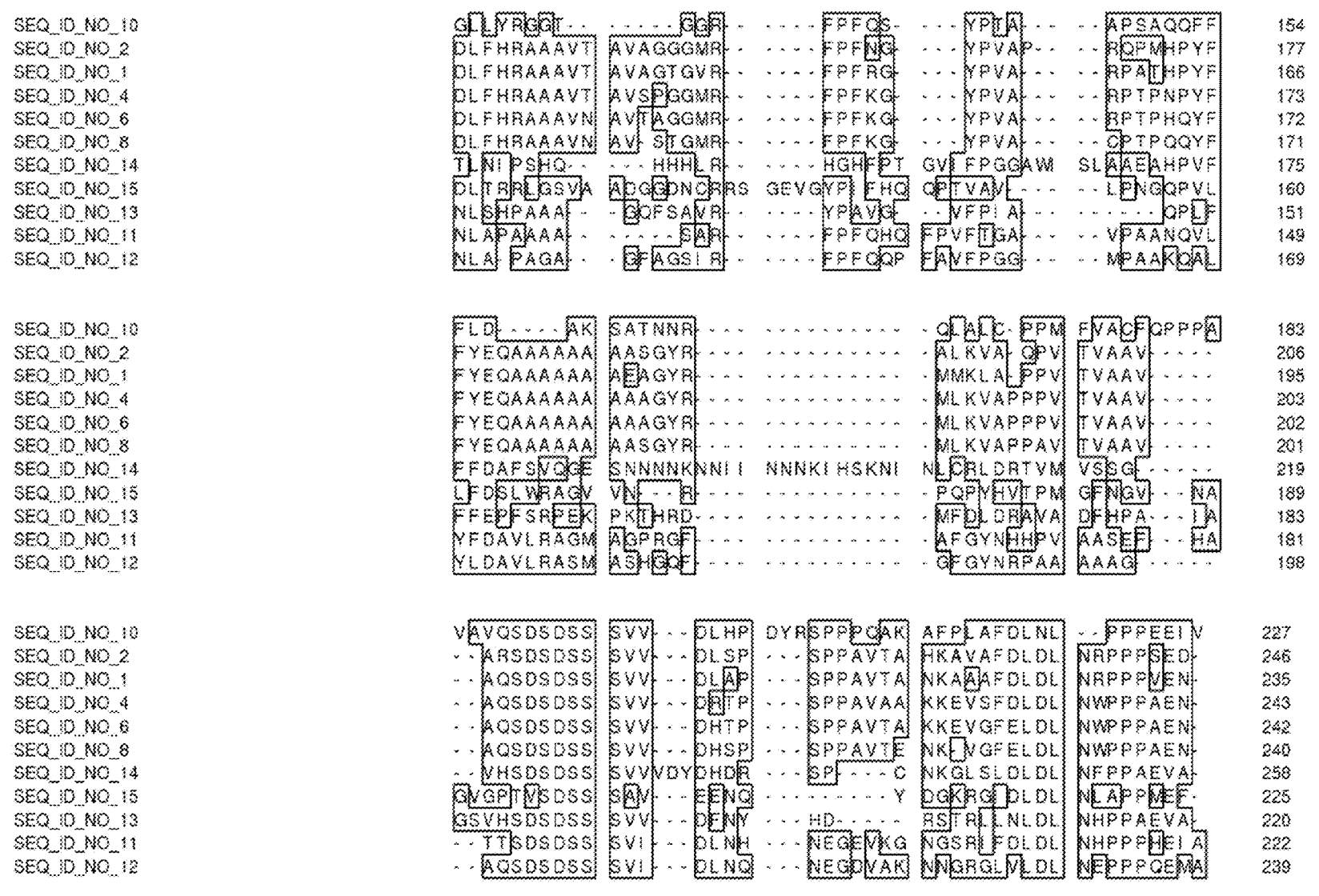

Examples of amino acid sequences of functional homologs of the polypeptide set forth in SEQ ID NO: 1 are provided in FIG. 4 and in the Sequence Listing. Such functional homologs include, for example, GI:84795244 (SEQ ID NO:2), CeresClone:1725396 (SEQ ID NO:4), CeresAnnot:8669118 (SEQ ID NO:6), CeresClone:280241 (SEQ ID NO:8), CeresClone:1712594 (SEQ ID NO:10), GI:190361125 (SEQ ID NO: 11), GI:4099921 (SEQ ID NO:12), GI:147844573 (SEQ ID NO:13), GI:67906426 (SEQ ID NO:14), GI:57012757 (SEQ ID NO:15), GI:56567583 (SEQ ID NO:16), GI:84795246 (SEQ ID NO:17), GI:84795248 (SEQ ID NO:18), CeresClone:1805203 (SEQ ID NO:20), CeresClone:101497672 (SEQ ID NO:22), CeresClone:224845 (SEQ ID NO:24), GI:115464685 (SEQ ID NO:25), CeresClone:1287030 (SEQ ID NO:27), CeresAnnot:8733383 (SEQ ID NO:29), GI:84795240 (SEQ ID NO:30), CeresClone:1806017 (SEQ ID NO:32), GI:84795242 (SEQ ID NO:33), GI:84795238 (SEQ ID NO:34), CeresClone:1733772 (SEQ ID NO:36), GI:37625037 (SEQ ID NO:37), GI:37625035 (SEQ ID NO:38), GI:147805535 (SEQ ID NO:39), GI:157358724 (SEQ ID NO:40), GI:4099914 (SEQ ID NO:41), CeresAnnot:1520029 (SEQ ID NO:43), CeresClone:1065091 (SEQ ID NO:45), CeresClone:1793792 (SEQ ID NO:47), CeresClone:1619220 (SEQ ID NO:49), GI:57012875 (SEQ ID NO:50), GI:147811787 (SEQ ID NO:51), CeresClone:1842925 (SEQ ID NO:53), GI:20340233 (SEQ ID NO:54). CeresClone:1657843 (SEQ ID NO:56), CeresAnnot:1455887 (SEQ ID NO:58), GI:118490009 (SEQ ID NO:59), CeresClone:1381515 (SEQ ID NO:61), CeresClone:22775 (SEQ ID NO:63), GI:60459377 (SEQ ID NO:64), CeresAnnot:1488231 (SEQ ID NO:66), CeresClone:1884969 (SEQ ID NO:68), CeresClone:1802100 (SEQ ID NO:70), GI:156145802 (SEQ ID NO:71). GI:28274832 (SEQ ID NO:72), CeresClone:568399 (SEQ ID NO:74), or GI:115460458 (SEQ ID NO:75). In some cases, a functional homolog of SEQ ID NO: 1 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1.

Figure 5:
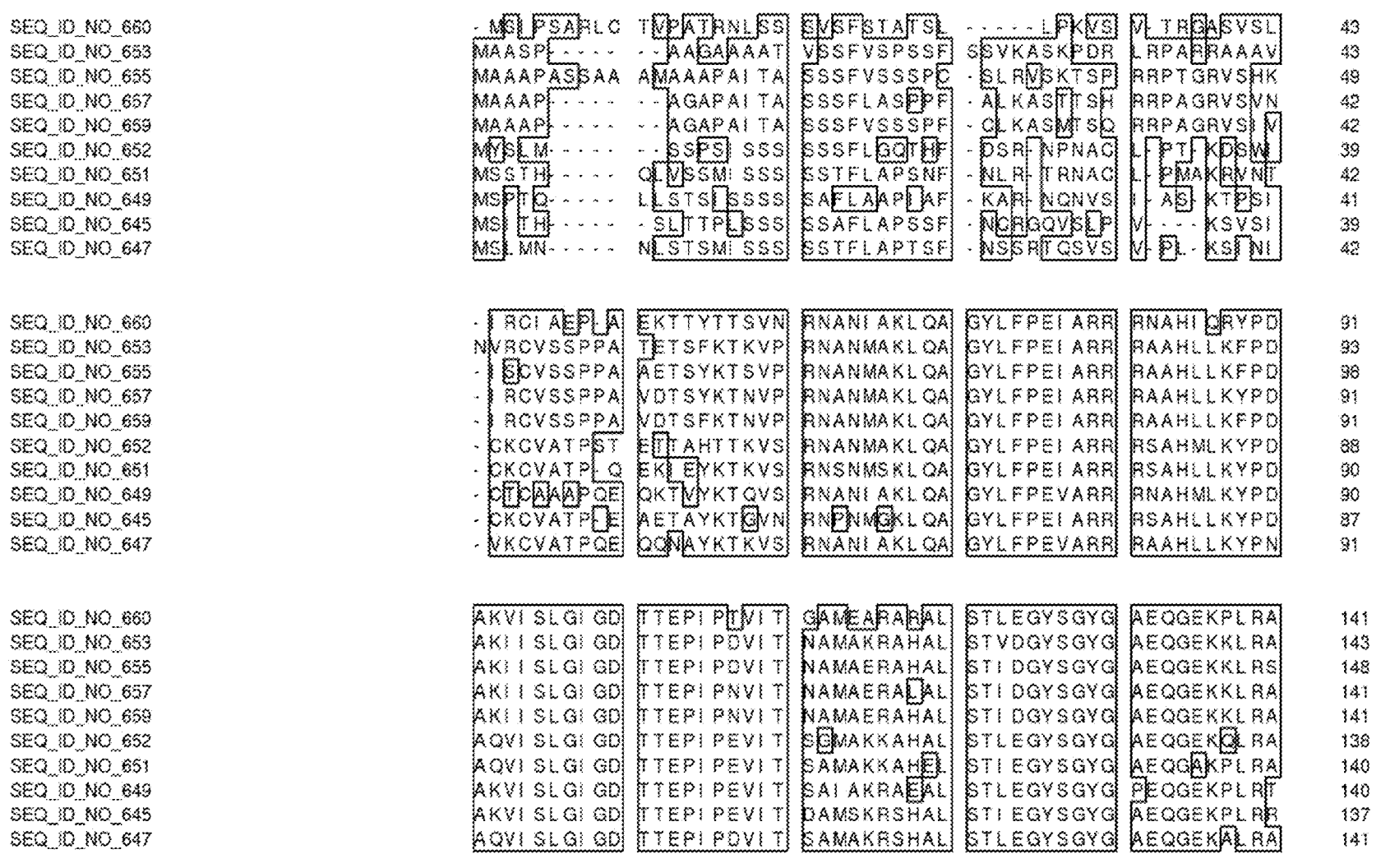
Figure 5:
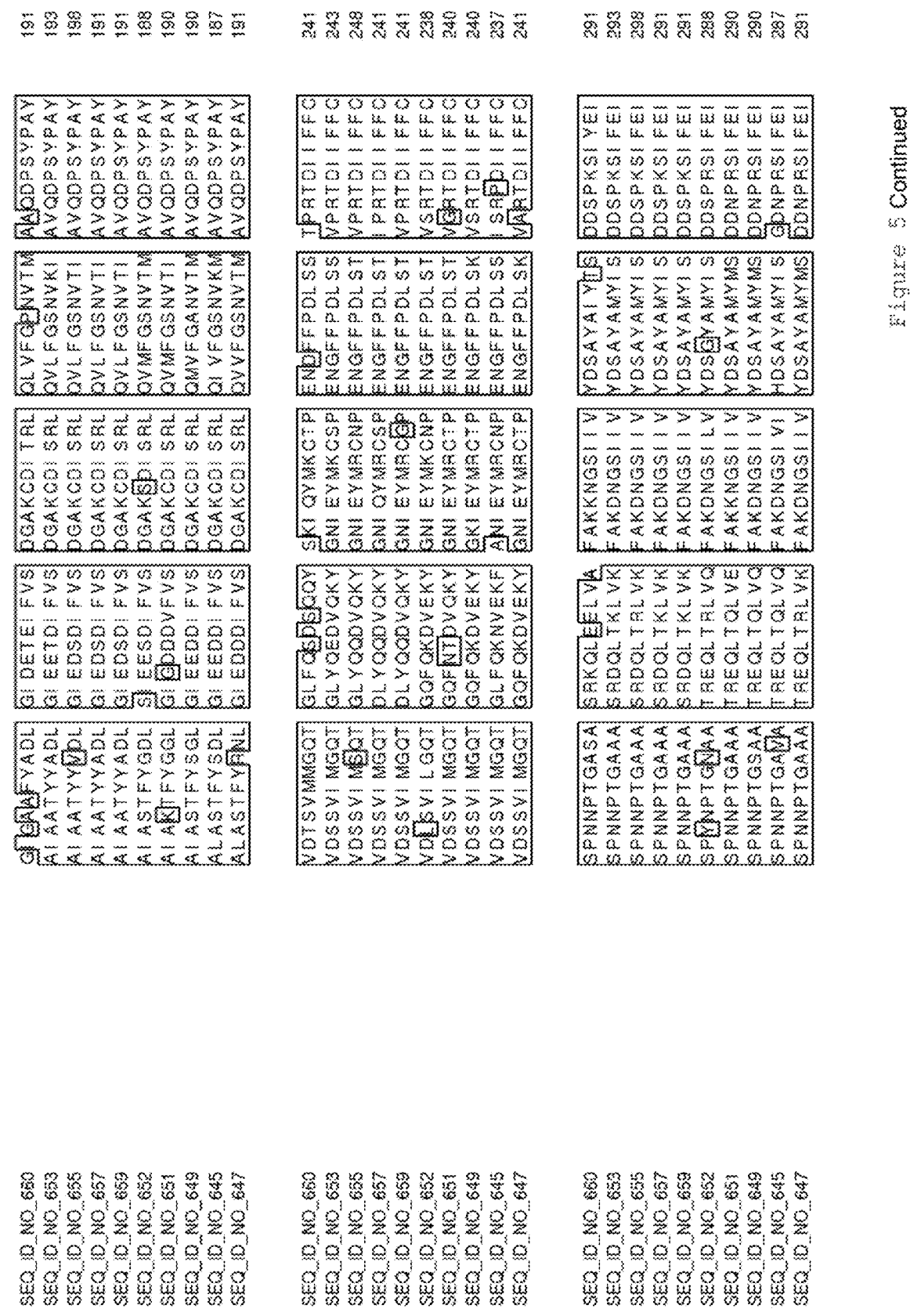
Figure 5:
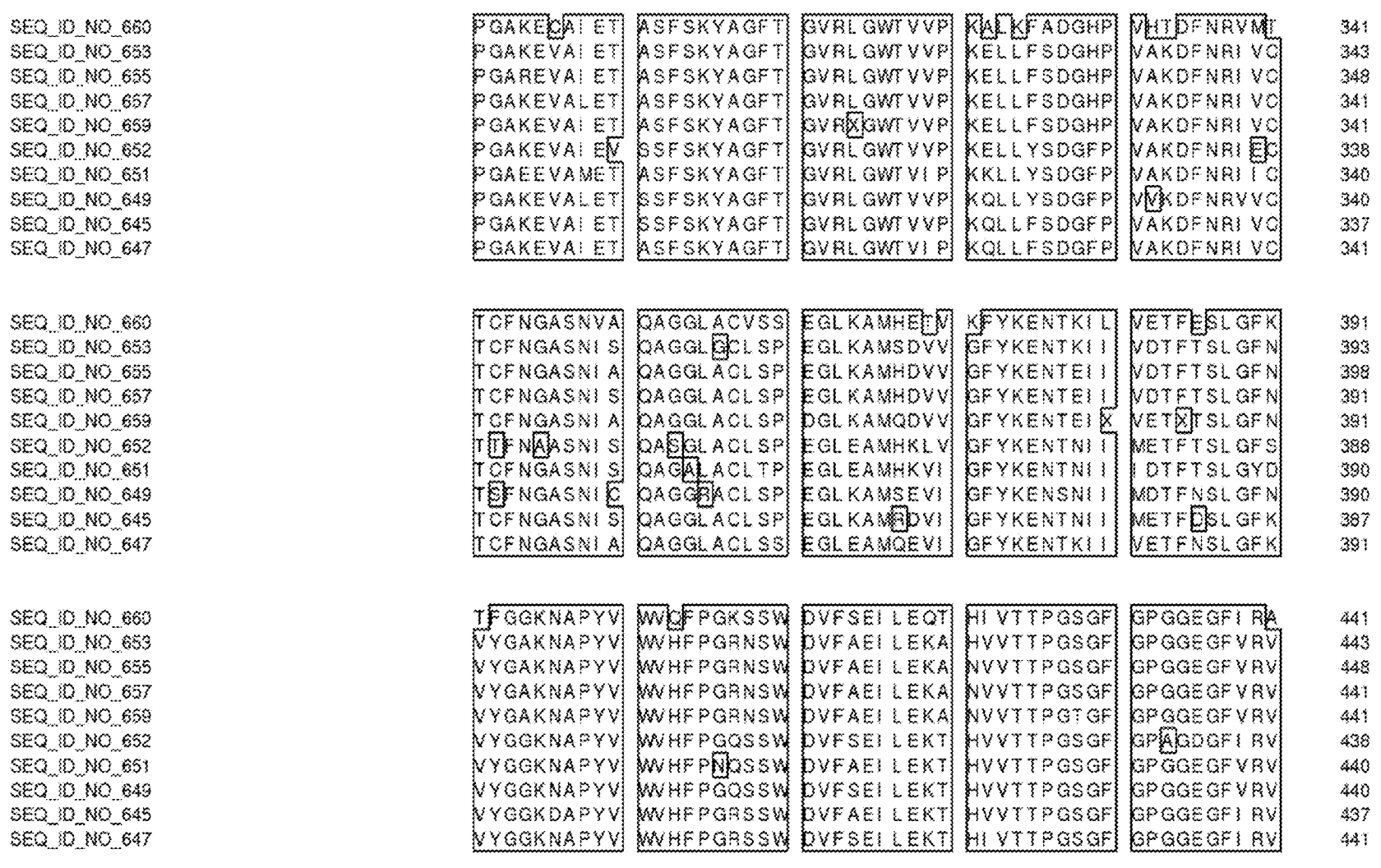

Examples of amino acid sequences of functional homologs of the polypeptide set forth in SEQ ID NO: 645 are provided in FIG. 5 and in the Sequence Listing. Such functional homologs include, for example CeresClone: 1925947 (SEQ ID NO: 647). CeresAnnot:1514501 (SEQ ID NO:649). CeresAnnot:849672 (SEQ ID NO:651), GI:157355942 (SEQ ID NO:652), GI:115452503 (SEQ ID NO: 653), CeresClone:1790933 (SEQ ID NO:655), CeresAnnot:8641620 (SEQ ID NO:657), CeresClone:281497 (SEQ ID NO:659), GI:168013851 (SEQ ID NO: 660), CeresClone:143214 (SEQ ID NO:662), CeresClone: 1781022 (SEQ ID NO:664), CeresClone:618639 (SEQ ID NO:666), GI:118483001 (SEQ ID NO: 667), CeresClone: 38404 (SEQ ID NO:669), GI:3549670 (SEQ ID NO:670), GI:37703720 (SEQ ID NO:671), GI:152149571 (SEQ ID NO: 672), GI:125603687 (SEQ ID NO:673), GI:108707679 (SEQ ID NO:674), GI:157352390 (SEQ ID NO:675), GI:159469820 (SEQ ID NO: 676), GI: 145344081 (SEQ ID NO:677), or Ceres Annot ID no. 1461228 (SEQ ID NO:689). In some cases, a functional homolog of SEQ ID NO: 645 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 645.

Examples of amino acid sequences of functional homologs of the polypeptide set forth in SEQ ID NO: 253 are provided in FIG. 6 and in the Sequence Listing. Such functional homologs include, for example, CeresClone: 951785 (SEQ ID NO: 255), CeresAnnot:1440346 (SEQ ID NO: 257), CeresClone:1085177 (SEQ ID NO: 259), or CeresClone:157151 (SEQ ID NO: 261). In some cases, a functional homolog of SEQ ID NO: 253 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 253.

Figure 7:
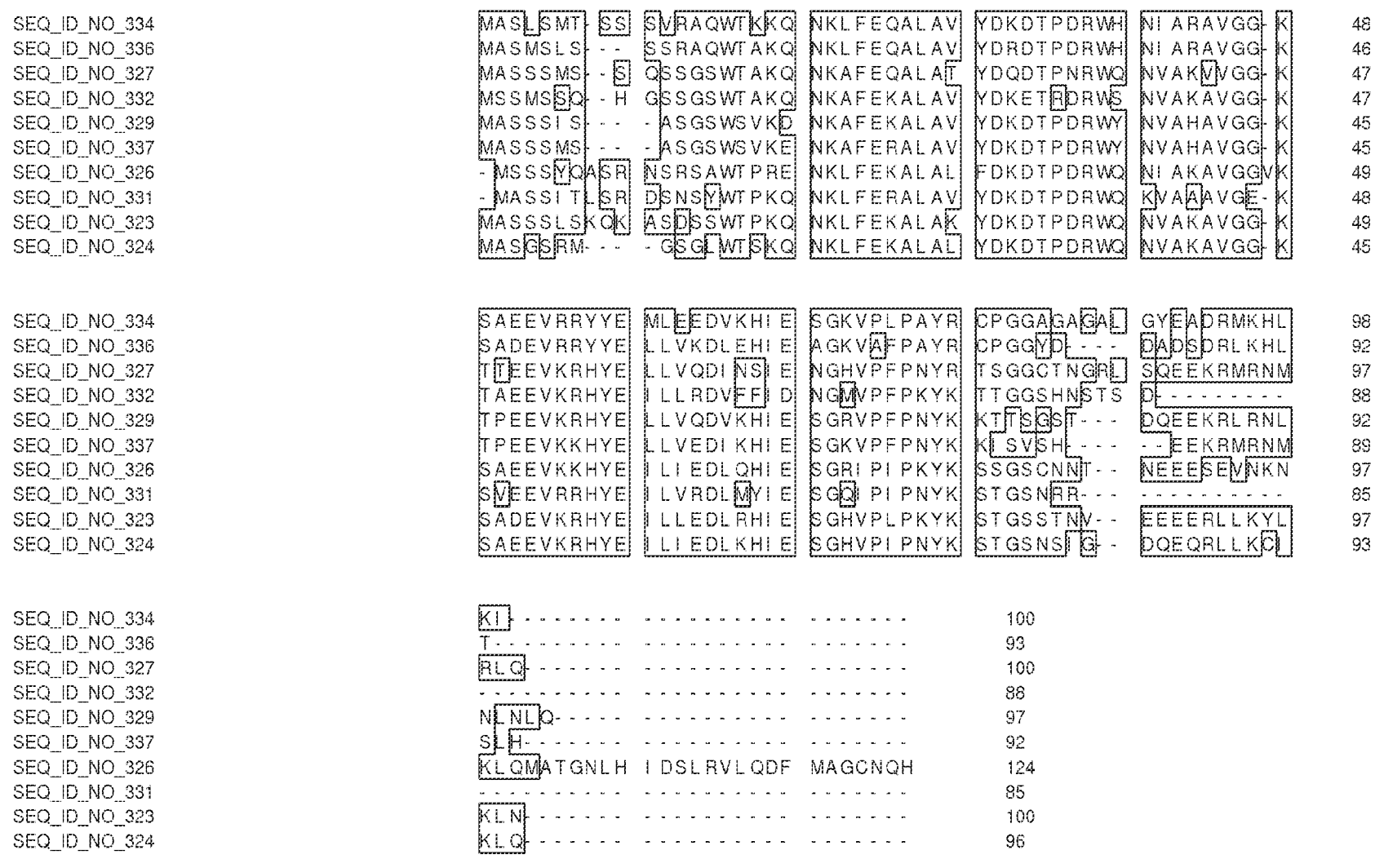

Examples of amino acid sequences of functional homologs of the polypeptide set forth in SEQ ID NO: 323 are provided in FIG. 7 and in the Sequence Listing. Such functional homologs include, for example, GI:157340812 (SEQ ID NO:324), CeresAnnot:1460824 (SEQ ID NO:326), GI:145356202 (SEQ ID NO:327), CeresClone:477814 (SEQ ID NO:329), CeresClone:1914387 (SEQ ID NO:331), GI:7981380 (SEQ ID NO:332), CeresClone:1910072 (SEQ ID NO:334), CeresClone:331755 (SEQ ID NO:336), GI:124360540 (SEQ ID NO:337), GI:157335318 (SEQ ID NO:338), CeresAnnot:1503394 (SEQ ID NO:340), CeresAnnot:1442707 (SEQ ID NO:342), GI:147784500 (SEQ ID NO:343), CeresAnnot:1514100 (SEQ ID NO:345), CeresAnnot:850366 (SEQ ID NO:347), CeresAnnot:543794 (SEQ ID NO:349), CeresAnnot:1495620 (SEQ ID NO:351), CeresClone:1653552 (SEQ ID NO:353), GI:147767321 (SEQ ID NO:354), CeresAnnot:1510450 (SEQ ID NO:356), GI: 110931736 (SEQ ID NO:357), CeresClone:1916884 (SEQ ID NO:359), CeresClone:1847251 (SEQ ID NO:361), CeresAnnot:1457249 (SEQ ID NO:363), CeresClone: 1113584 (SEQ ID NO:365), CeresClone:1927753 (SEQ ID NO:367), CeresAnnot:857342 (SEQ ID NO:369), CeresClone:100068619 (SEQ ID NO:371), GI:145327247 (SEQ ID NO:372), CeresAnnot:8461532 (SEQ ID NO:374), CeresClone:1722230 (SEQ ID NO:376), CeresClone: 1897493 (SEQ ID NO:378), CeresAnnot:838426 (SEQ ID NO:380), CeresAnnot:827713 (SEQ ID NO:382), CeresClone:1763593 (SEQ ID NO:384), CeresClone:143475 (SEQ ID NO:386), CeresAnnot:8456508 (SEQ ID NO:388), CeresClone:100002959 (SEQ ID NO:390), GI:118137433 (SEQ ID NO:391), CeresClone:1523182 (SEQ ID NO:393), CeresClone:1761808 (SEQ ID NO:395), CeresClone: 1069222 (SEQ ID NO:397), CeresAnnot:8734209 (SEQ ID NO:399), CeresAnnot:8461540 (SEQ ID NO:401), CeresClone:1086604 (SEQ ID NO:403), CeresClone:41695 (SEQ ID NO:405), GI:112292440 (SEQ ID NO:406), GI:116830269 (SEQ ID NO:407), CeresClone:1775942 (SEQ ID NO:409), CeresClone:1723374 (SEQ ID NO:411), CeresAnnot:1457230 (SEQ ID NO:413), CeresAnnot: 8667653 (SEQ ID NO:415), GI: 115465643 (SEQ ID NO:416), GI:5091605 (SEQ ID NO:417), GI:125553458 (SEQ ID NO:418), CeresAnnot:1510435 (SEQ ID NO:420), GI:115438765 (SEQ ID NO:421). GI:112292438 (SEQ ID NO:422), or CeresAnnot:1770841 (SEQ ID NO:424). In some cases, a functional homolog of SEQ ID NO: 323 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 323.

Figure 8:
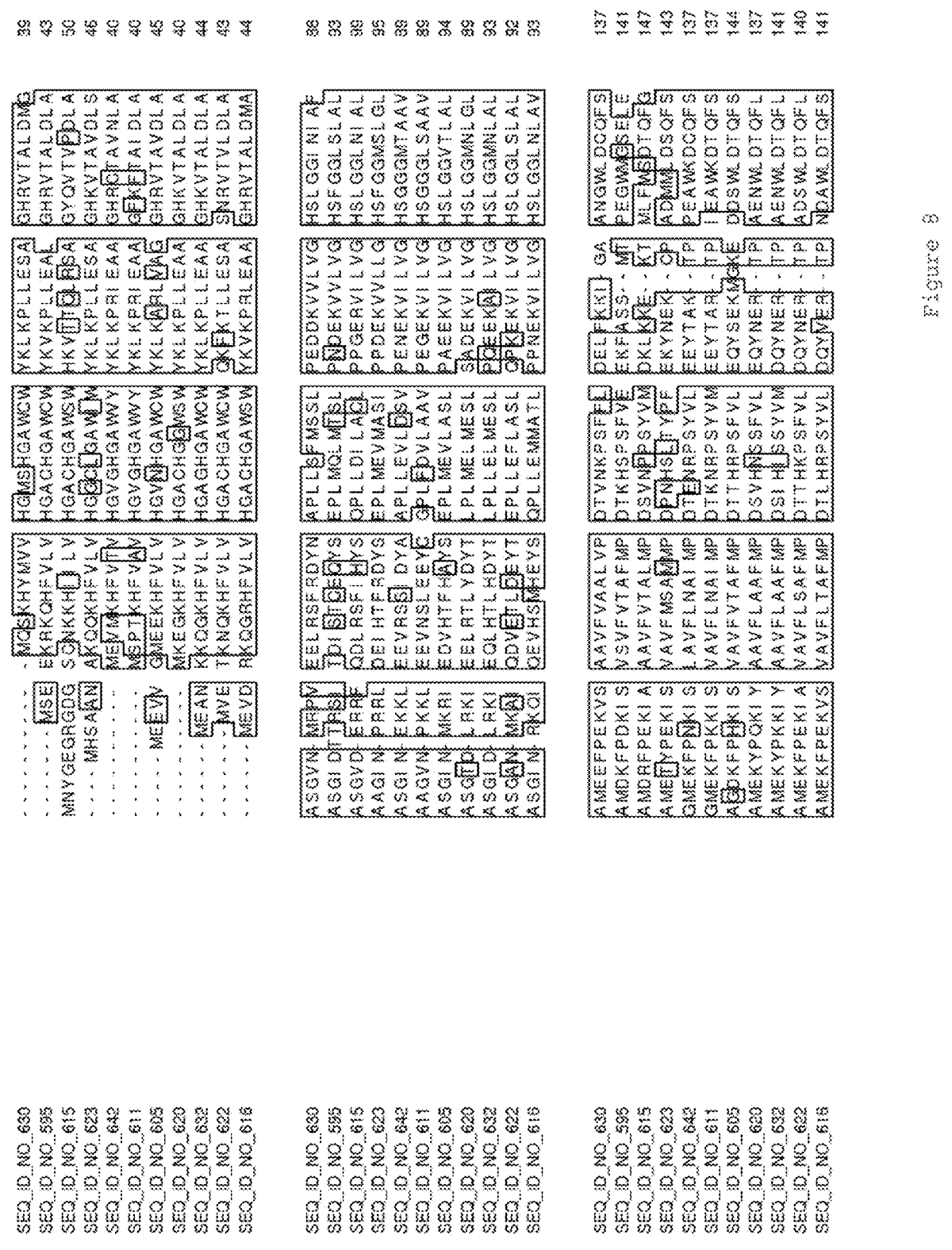
Figure 8:
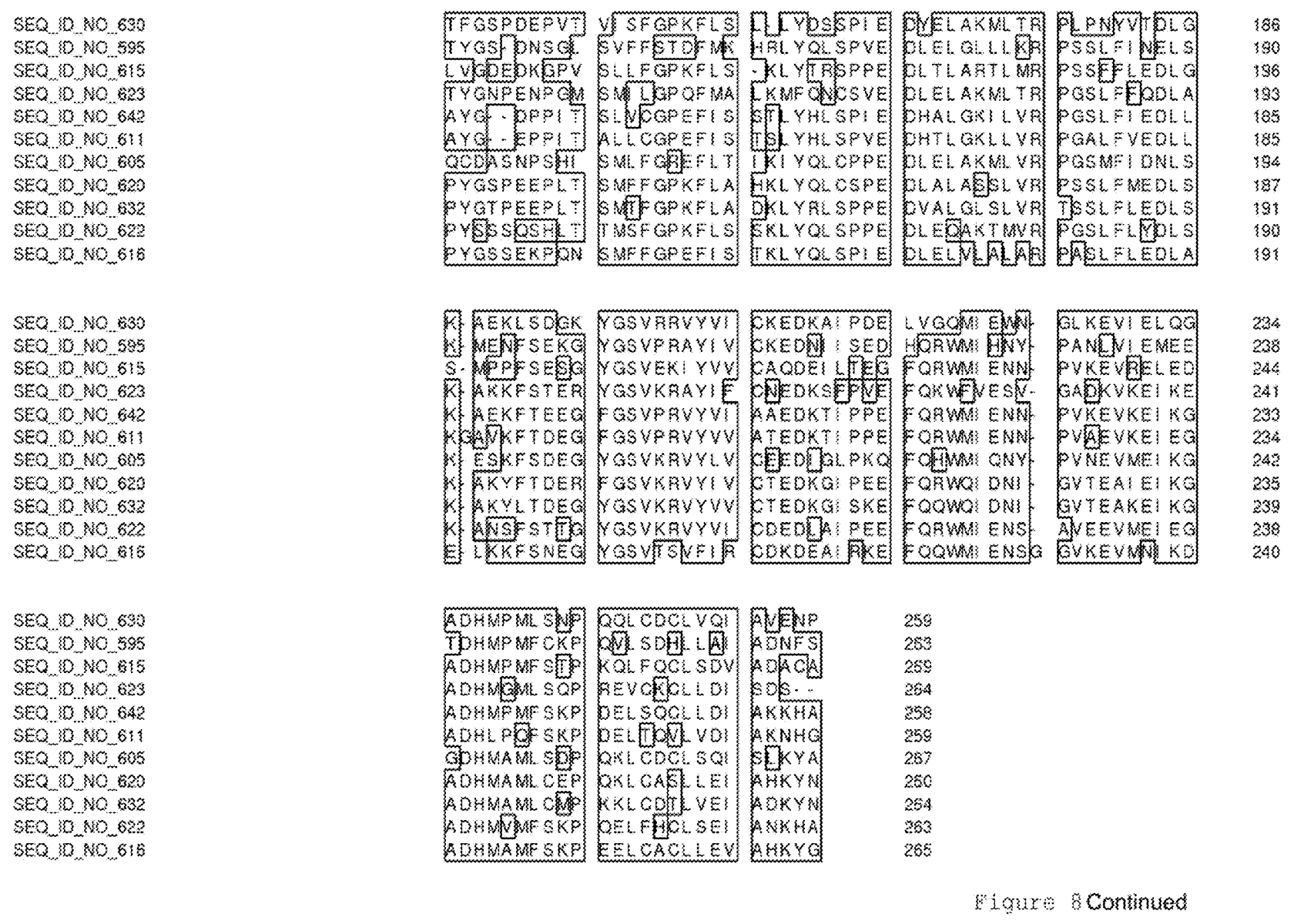

Examples of amino acid sequences of functional homologs of the polypeptide set forth in SEQ ID NO: 595 are provided in FIG. 8 and in the Sequence Listing. Such functional homologs include, for example, CeresClone: 644331 (SEQ ID NO: 597), GI:15227859 (SEQ ID NO: 598), CeresAnnot:1504349 (SEQ ID NO: 600), CeresAnnot: 1265088 (SEQ ID NO: 602), (SEQ ID NO: 603), GI:125527987 (SEQ ID NO: 604), GI:14279437 (SEQ ID NO: 605), ES902065 (SEQ ID NO: 606), CeresClone: 1065042 (SEQ ID NO: 608), GI:157329790 (SEQ ID NO: 609), GI:15227861 (SEQ ID NO: 610), GI:146272407 (SEQ ID NO: 611), CeresClone:95094 (SEQ ID NO: 613), CeresClone:1714893 (SEQ ID NO: 615), GI:157329890 (SEQ ID NO: 616), CeresAnnot:859635 (SEQ ID NO: 618), GI:115440397 (SEQ ID NO: 619), GI:40549303 (SEQ ID NO: 620), CeresAnnot:1457048 (SEQ ID NO: 622), GI:50401192 (SEQ ID NO: 623), CeresAnnot:1451281 (SEQ ID NO: 625), CeresAnnot:1510252 (SEQ ID NO: 627), CeresClone:1822691 (SEQ ID NO: 629), GI:197312921 (SEQ ID NO: 630), CeresAnnot:8456439 (SEQ ID NO: 632), EX096388 (SEQ ID NO: 633), GI:15028131 (SEQ ID NO: 634), CeresClone:270875 (SEQ ID NO: 636), GI:27754457 (SEQ ID NO: 637), GI:16648679 (SEQ ID NO: 638), GI:15227863 (SEQ ID NO: 639), CeresAnnot:1451282 (SEQ ID NO: 641), GI:53830670 (SEQ ID NO: 642), GI:146272405 (SEQ ID NO: 643), or CeresAnnot: 827940 (SEQ ID NO:691). In some cases, a functional homolog of SEQ ID NO: 595 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 595.

Figure 9:
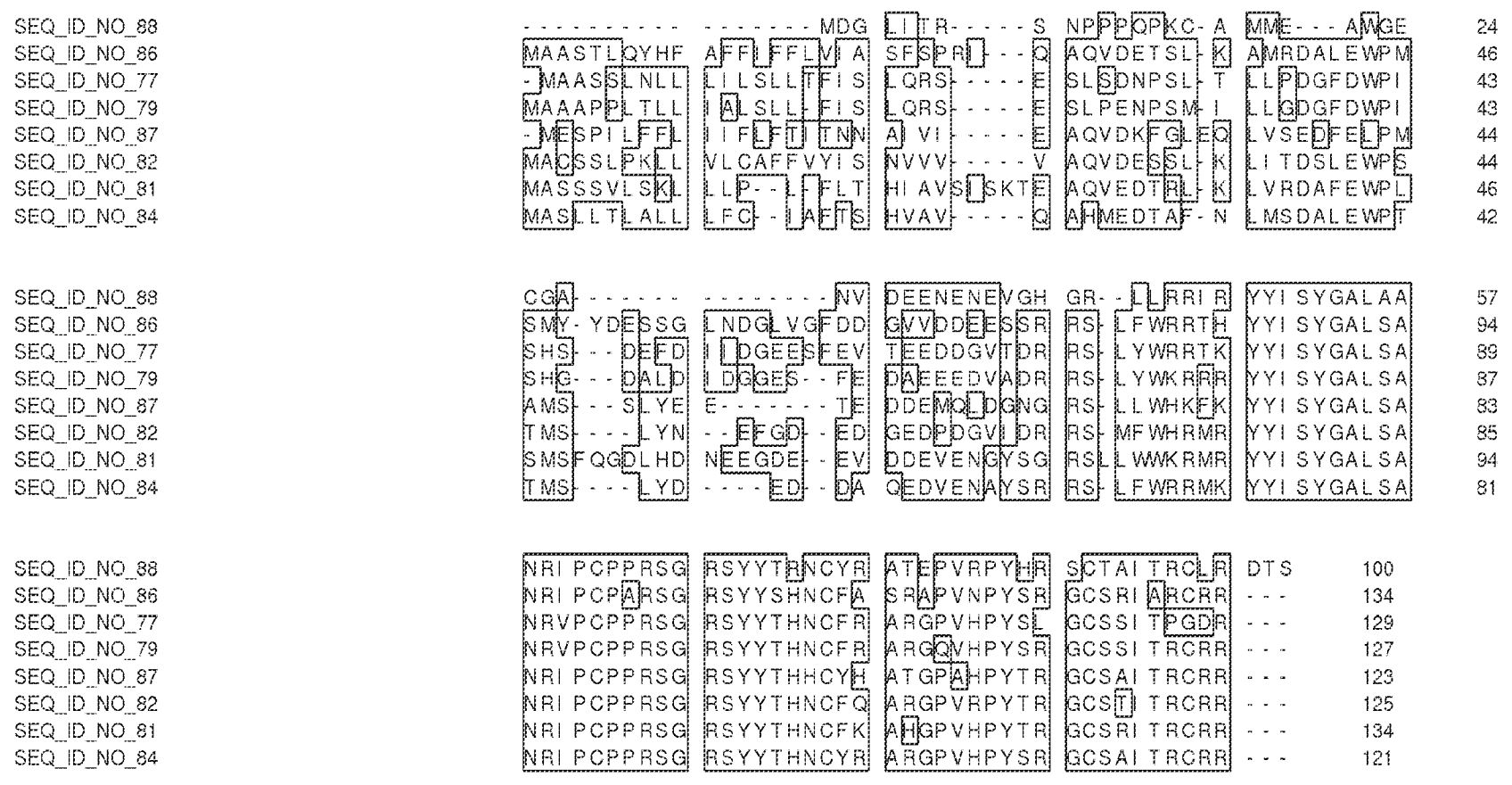

Examples of amino acid sequences of functional homologs of the polypeptide set forth in SEQ ID NO: 77 are provided in FIG. 9 and in the Sequence Listing. Such functional homologs include, for example, CeresClone: 1387948 (SEQ ID NO: 79), CeresClone:1937714 (SEQ ID NO: 81), GI:157345132 (SEQ ID NO: 82), CeresClone: 464828 (SEQ ID NO: 84), CeresAnnot:1451368 (SEQ ID NO: 86), GI:37695575 (SEQ ID NO: 87), GI: 116790033 (SEQ ID NO: 88), CeresClone:1346042 (SEQ ID NO: 90), CeresClone: 1118610 (SEQ ID NO: 92), CeresClone: 982000 (SEQ ID NO: 94), CeresClone:959670 (SEQ ID NO: 96). CeresClone:952522 (SEQ ID NO: 98), CeresClone:1914539 (SEQ ID NO: 100), CeresClone:668581 (SEQ ID NO: 102), CeresClone:1914939 (SEQ ID NO: 104), CeresClone:723694 (SEQ ID NO: 106), CeresAnnot: 1456949 (SEQ ID NO: 108), CeresAnnot:1539918 (SEQ ID NO: 110), CeresAnnot:8456138 (SEQ ID NO: 112), CeresAnnot:1486506 (SEQ ID NO: 114), or GI: 116786293 (SEQ ID NO: 115). In some cases, a functional homolog of SEQ ID NO: 77 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 77.

Figure 10:
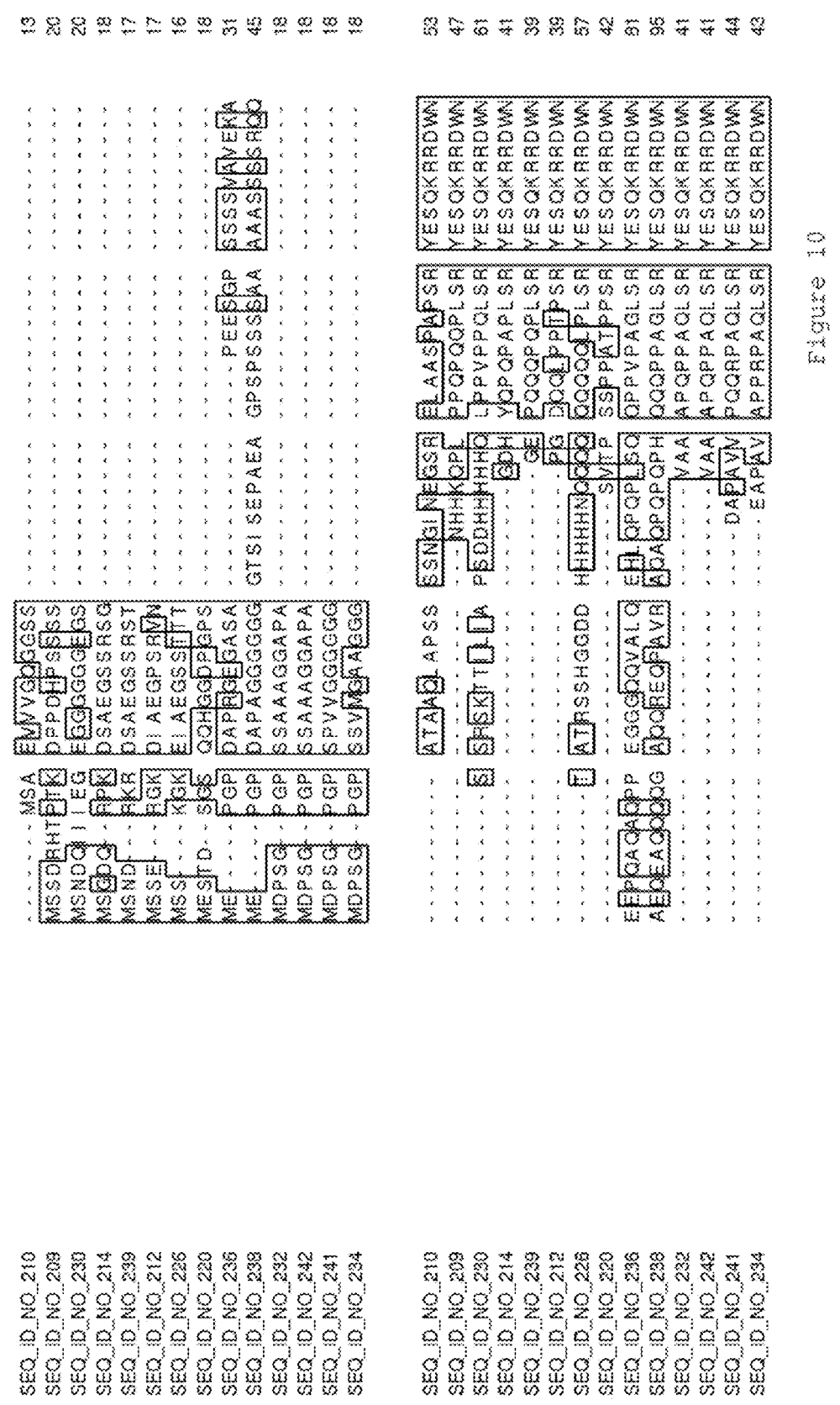
Figure 10:
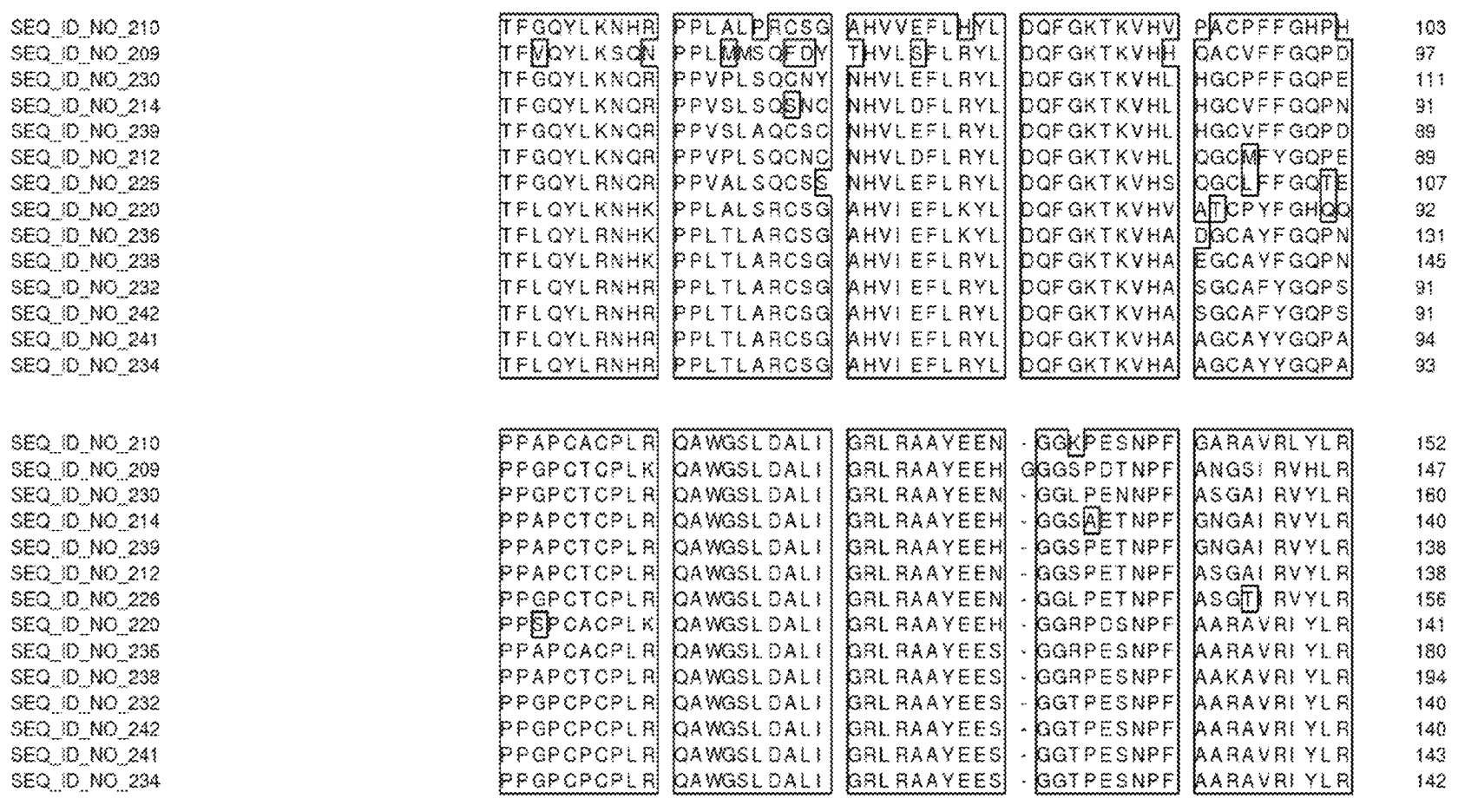
Figure 10:
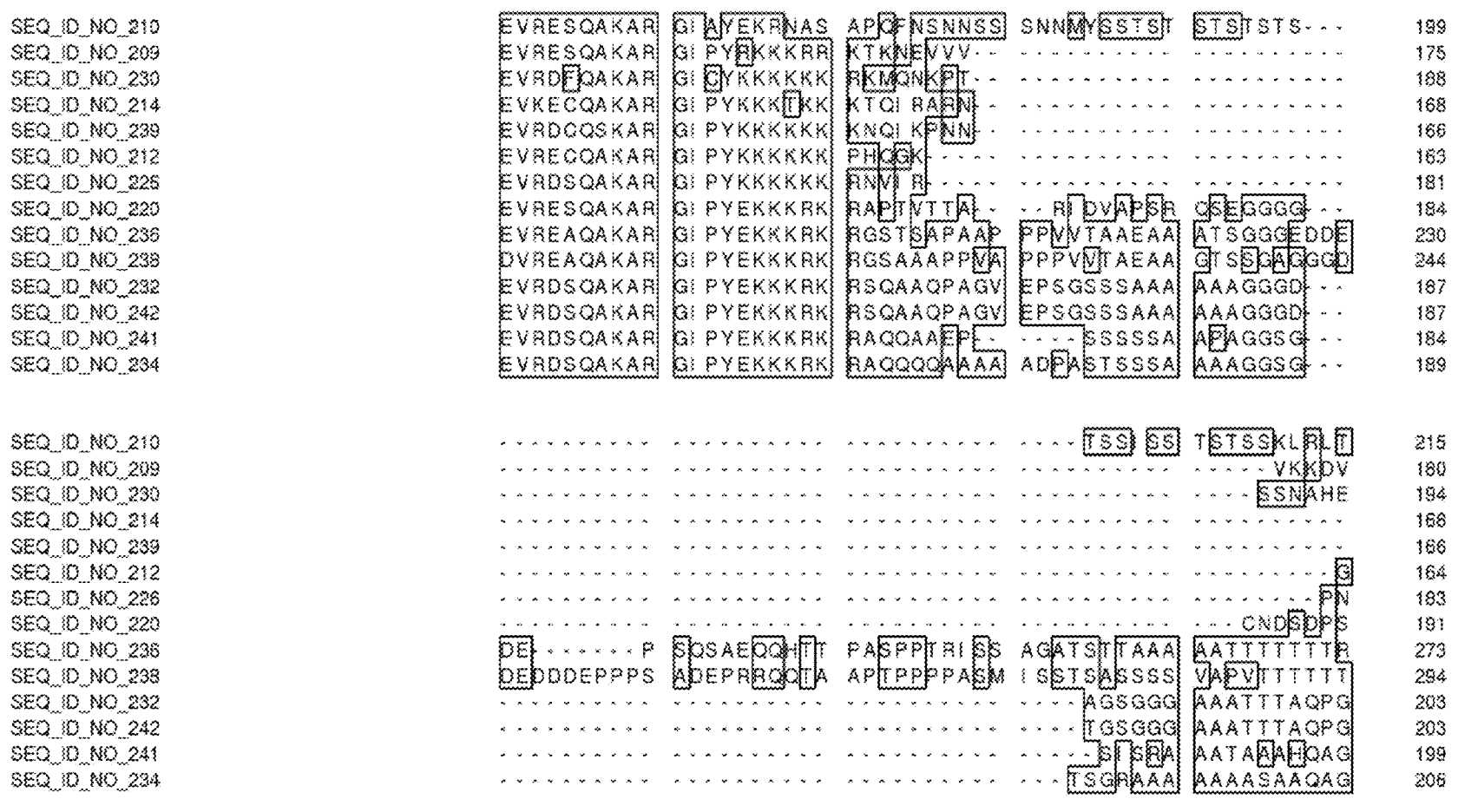

Examples of amino acid sequences of functional homologs of the polypeptide set forth in SEQ ID NO: 209 are provided in FIG. 10 and in the Sequence Listing. Such functional homologs include, for example, GI:116780542 (SEQ ID NO: 210), CeresClone:1848017 (SEQ ID NO: 212), CeresAnnot:1466494 (SEQ ID NO: 214), CeresAnnot: 1449022 (SEQ ID NO: 216), CeresAnnot:1482911 (SEQ ID NO: 218), CeresClone:1118987 (SEQ ID NO: 220), CeresClone:1073674 (SEQ ID NO: 222), CeresClone:1084747 (SEQ ID NO: 224), CeresClone:536345 (SEQ ID NO: 226), CeresClone:1650005 (SEQ ID NO: 228), CeresAnnot: 8453882 (SEQ ID NO: 230), CeresAnnot:1373087 (SEQ ID NO: 232), CeresAnnot:8669372 (SEQ ID NO: 234), CeresClone:1048839 (SEQ ID NO: 236), CeresClone:281322 (SEQ ID NO: 238), GI:147795605 (SEQ ID NO: 239). CeresClone:2004419 (SEQ ID NO: 241). GI:125543059 (SEQ ID NO: 242), AT1G16910_LSH8 (SEQ ID NO: 243), AT1G78815_LSH7 (SEQ ID NO: 244), AT2G31160_LSH3 (SEQ ID NO: 245), AT2G42610_LSH10 (SEQ ID NO: 246), AT3G04510_LSH2 (SEQ ID NO: 247), AT3G23290_LSH4 (SEQ ID NO: 248), AT5G28490_LSH1 (SEQ ID NO: 249), AT5G58500_LSH5 (SEQ ID NO: 250), or At1g07090_LSH6 (SEQ ID NO: 251). In some cases, a functional homolog of SEQ ID NO: 209 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 209.

Figure 11:
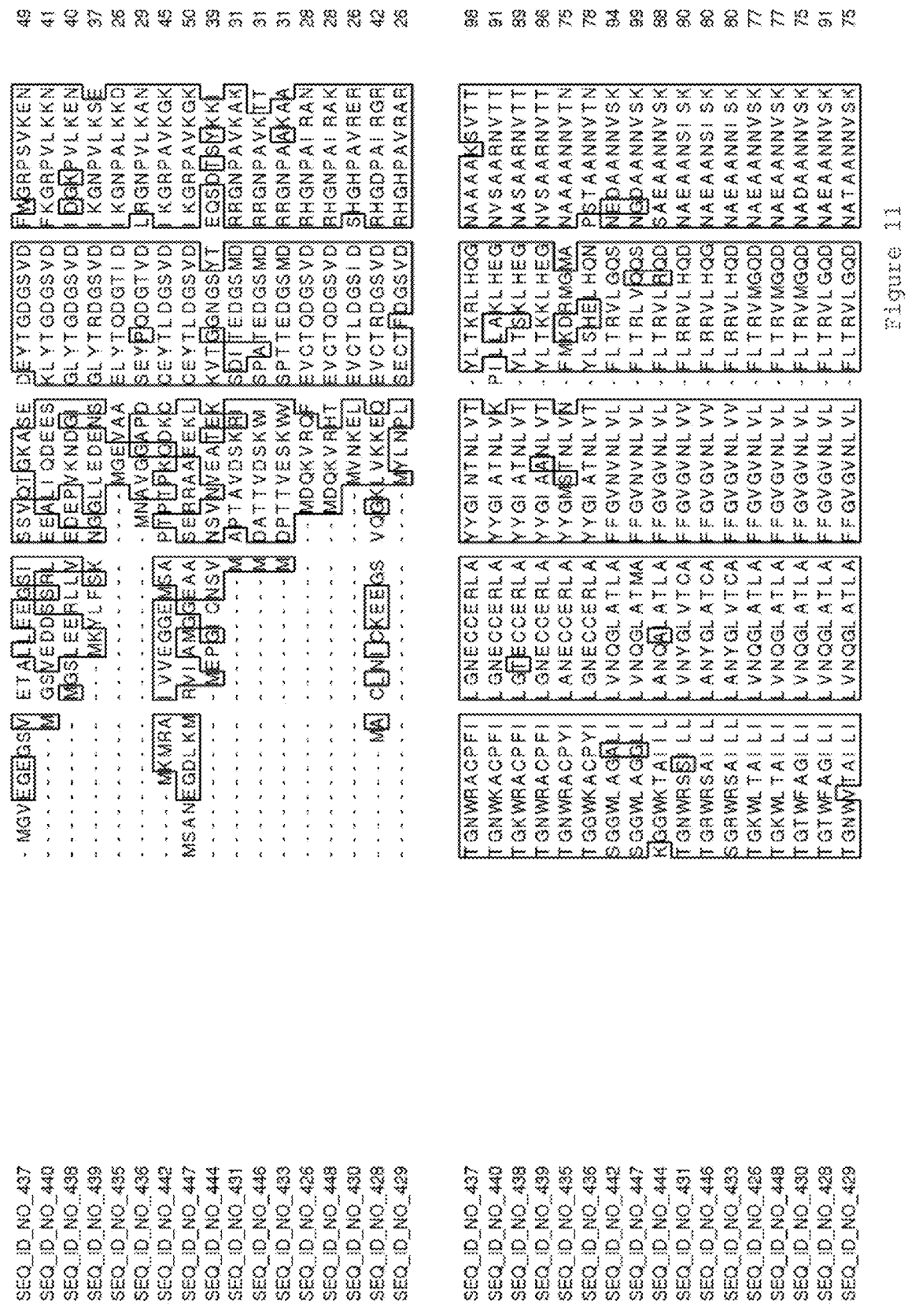
Figure 11:
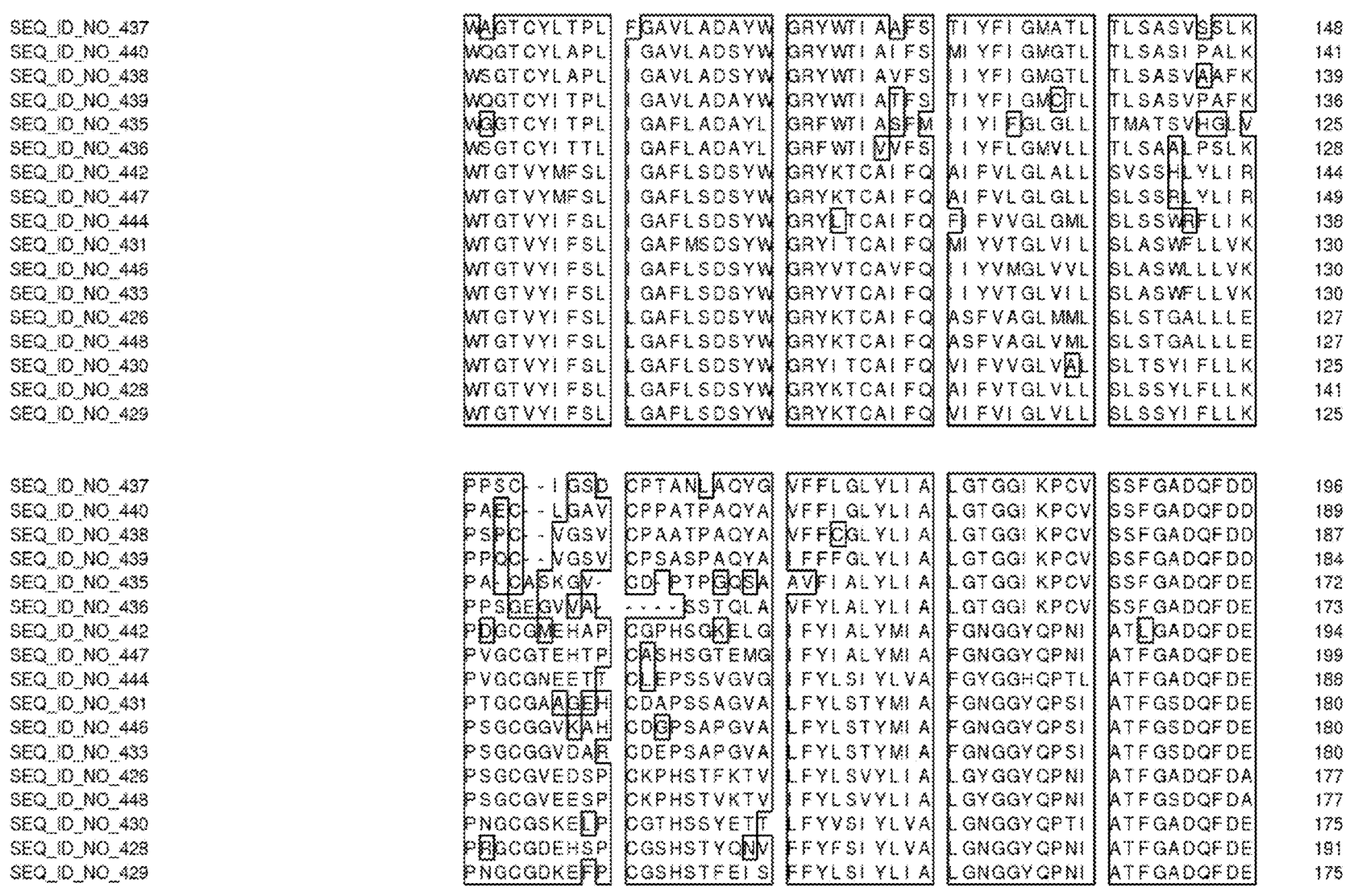
Figure 11:
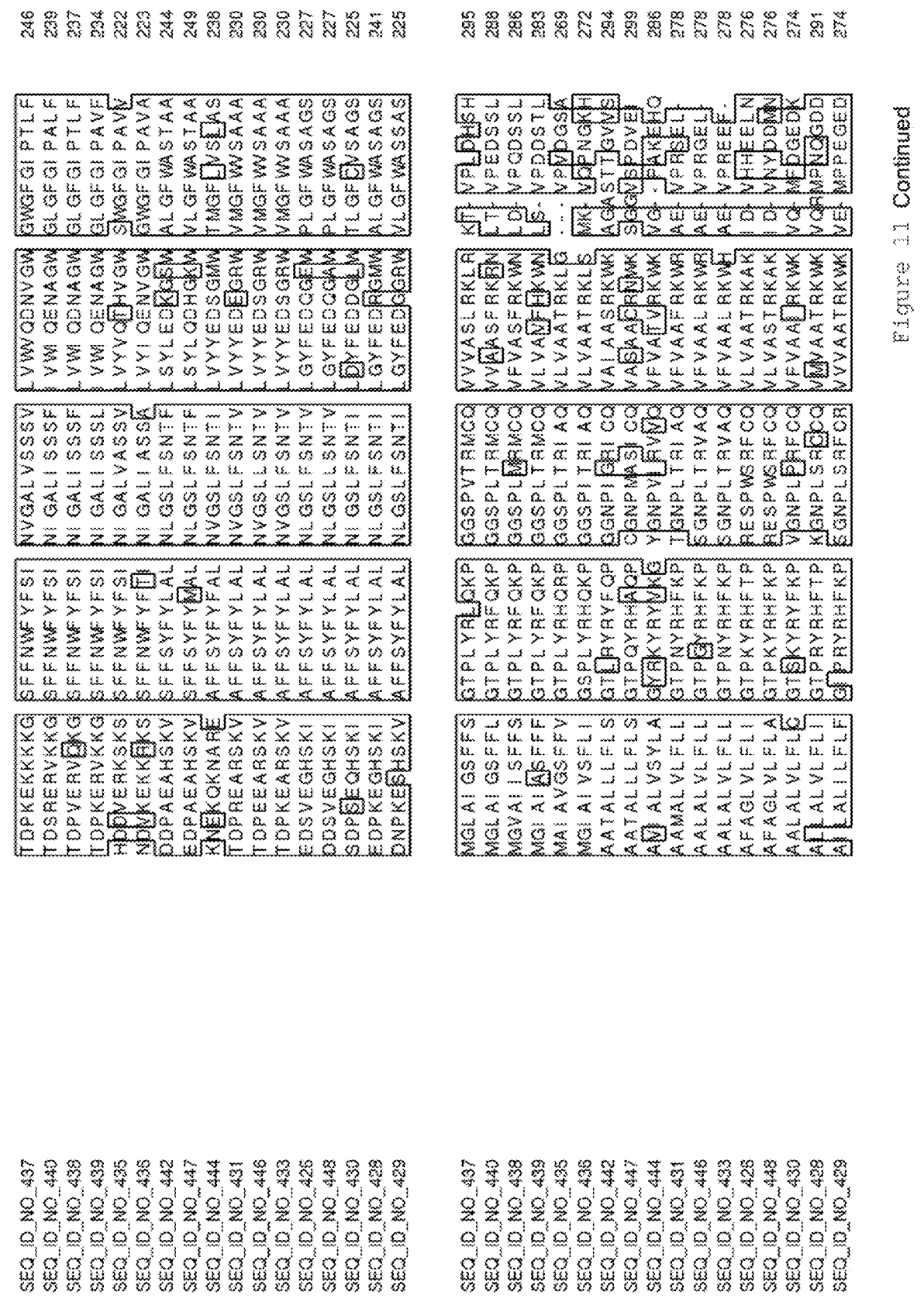
Figure 11:
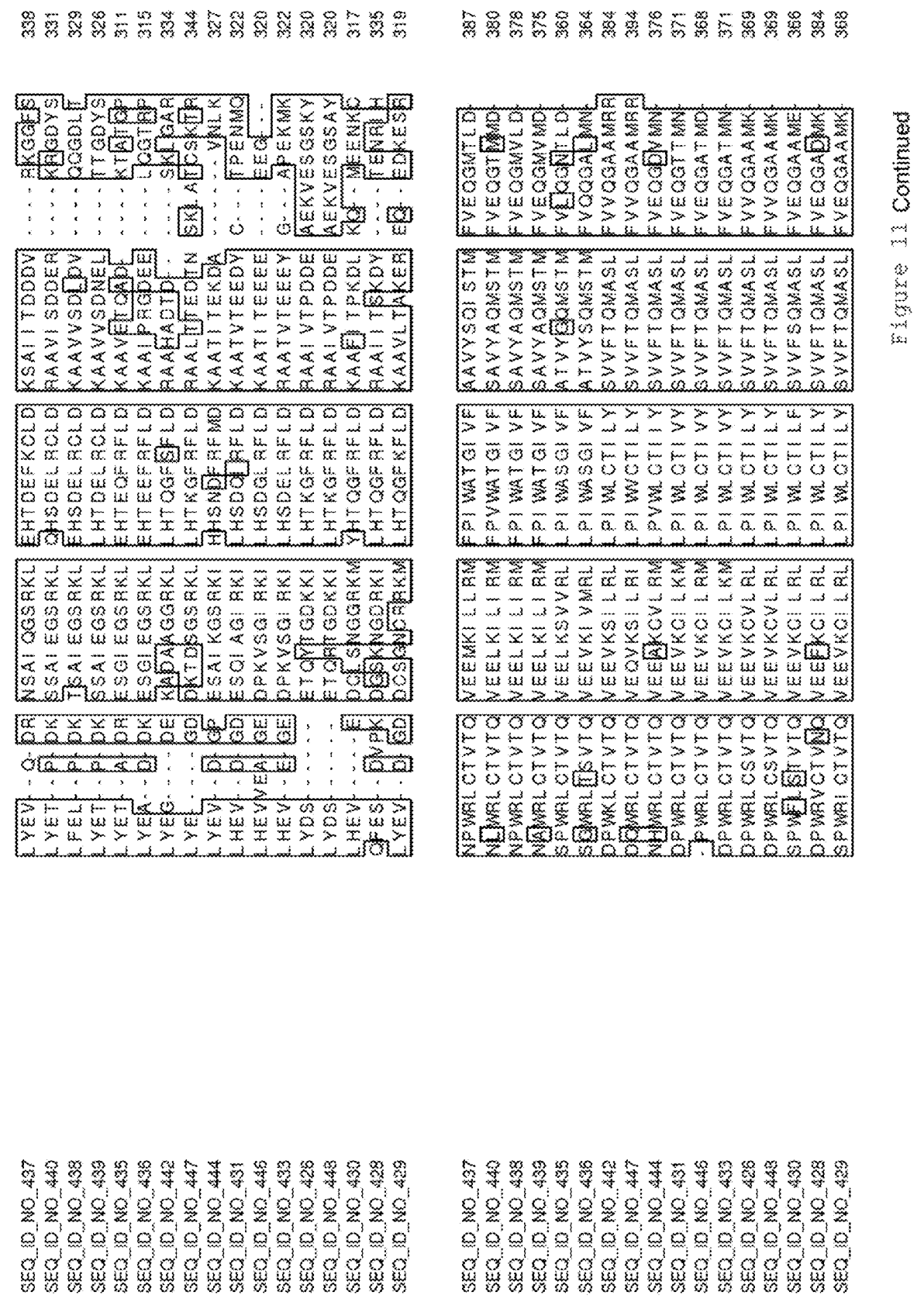
Figure 11:
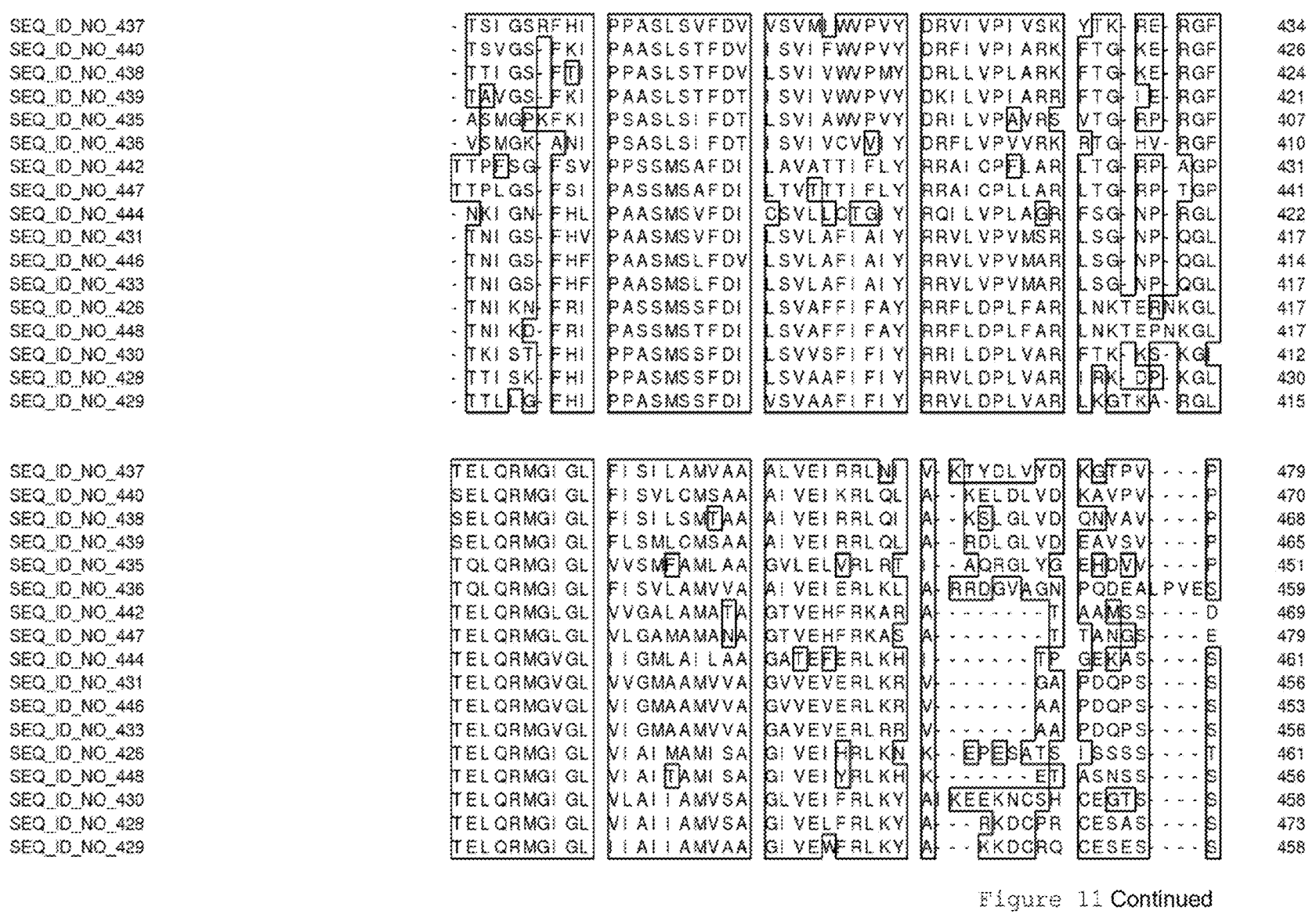
Figure 11:
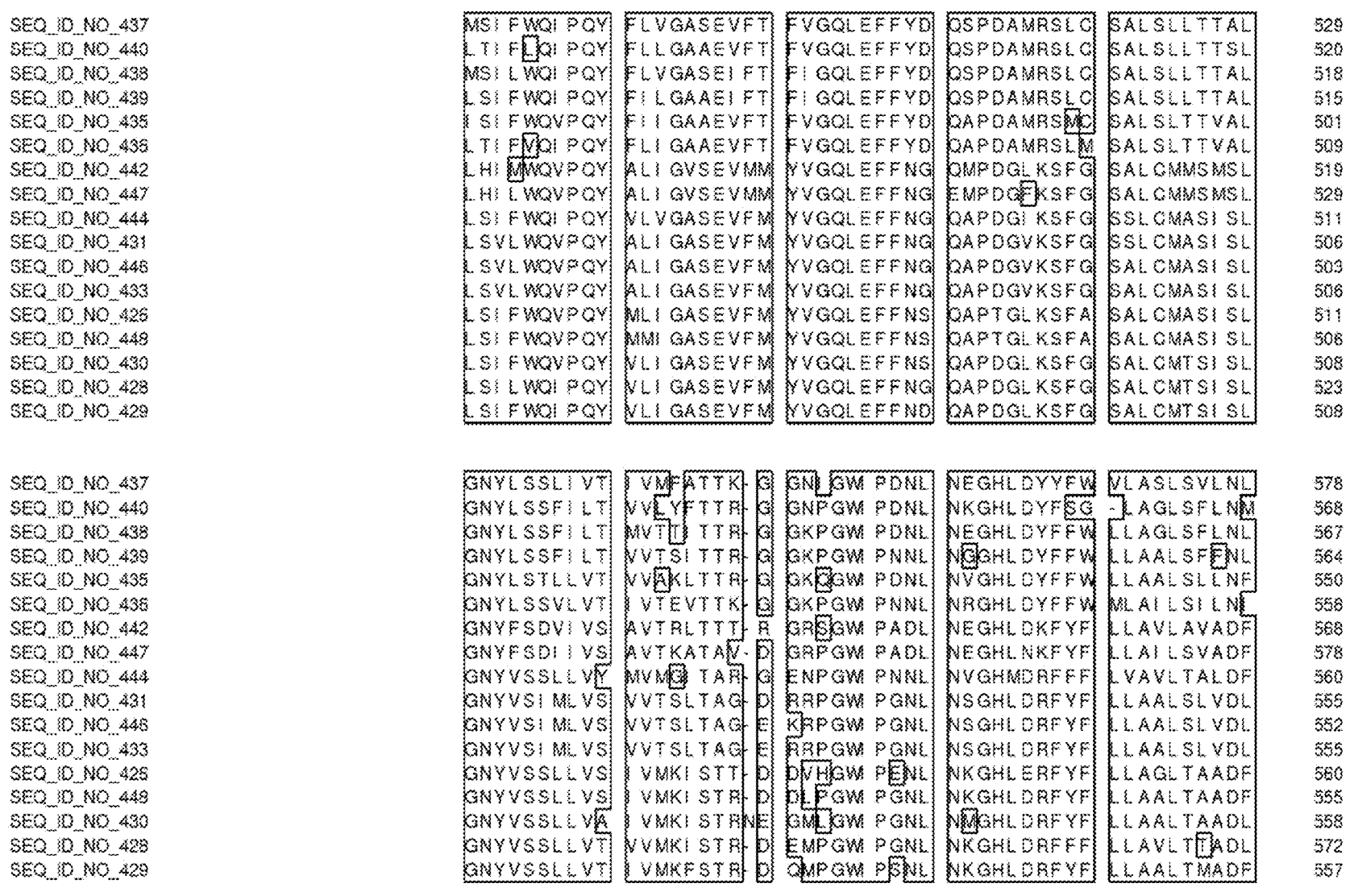
Figure 11:
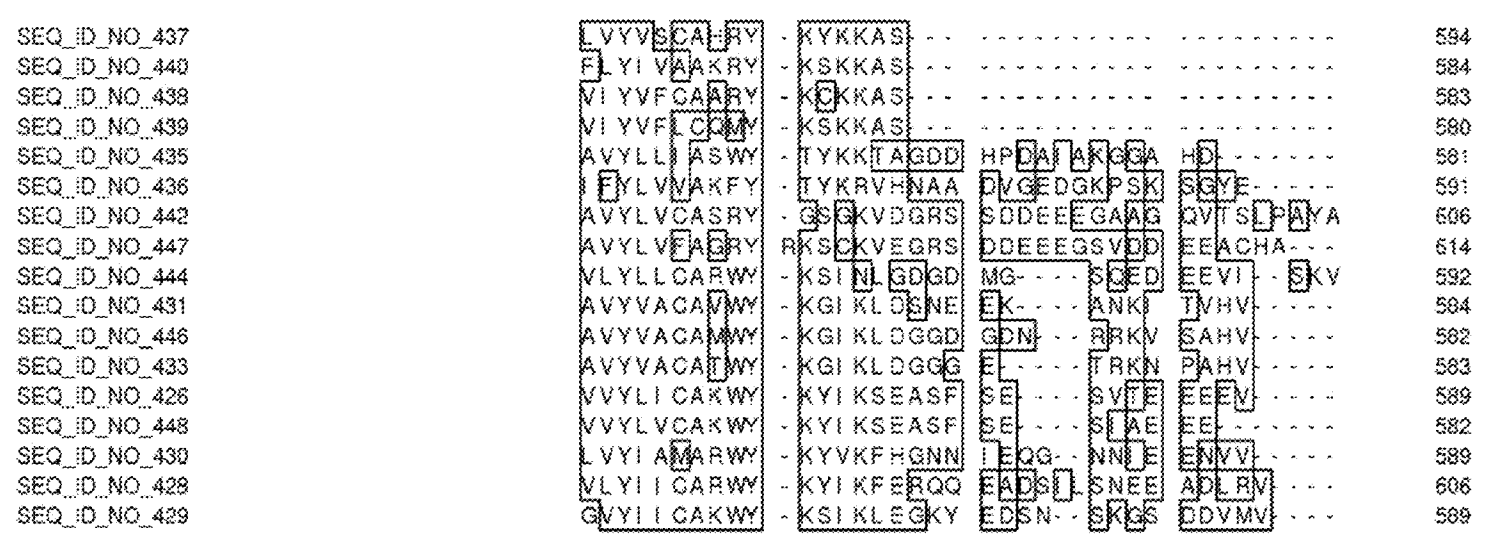

Examples of amino acid sequences of functional homologs of the polypeptide set forth in SEQ ID NO: 426 are provided in FIG. 11 and in the Sequence Listing. Such functional homologs include, for example, CeresAnnot: 1472338_Pb (SEQ ID NO: 428), GI:157344683_Vv (SEQ ID NO: 429), GI:87240677_Mt (SEQ ID NO: 430), GI:115448297_Os (SEQ ID NO: 431), CeresClone: 1844568_Pv (SEQ ID NO: 433), CeresClone:797829_Tm (SEQ ID NO: 435), GI:168033816_Pp (SEQ ID NO: 436), GI:116788004_Ps (SEQ ID NO: 437), GI:149900503_Ha (SEQ ID NO: 438), GI:4102839_Sl (SEQ ID NO: 439), GI:31088360_Vf (SEQ ID NO: 440), CeresAnnot: 8681236_Sb (SEQ ID NO: 442), CeresAnnot:8519531_Gm (SEQ ID NO: 444), CeresAnnot:8631372_Zm (SEQ ID NO: 446), GI:151426449_Hv (SEQ ID NO: 447), GI:192757675_Br (SEQ ID NO: 448), GI:2655098 (SEQ ID NO: 449), GI:194690746 (SEQ ID NO: 450), CeresClone: 752925 (SEQ ID NO: 452), GI:125540898 (SEQ ID NO: 453), GI:26451333 (SEQ ID NO: 454), GI:2160144 (SEQ ID NO: 455), GI:30696666 (SEQ ID NO: 456), GI:125556922 (SEQ ID NO: 457), CeresAnnot:1529287 (SEQ ID NO: 459), CeresClone:1806748 (SEQ ID NO: 461), CeresAnnot:8755095 (SEQ ID NO: 463), GI:147827175 (SEQ ID NO: 464), CeresClone:1888865 (SEQ ID NO: 466), GI:157337163 (SEQ ID NO: 467), GI:115434472 (SEQ ID NO: 468), CeresAnnot:6252512 (SEQ ID NO: 470), CeresAnnot:1569074_Mt (SEQ ID NO: 472), CeresAnnot:1475845 (SEQ ID NO: 474), CeresAnnot: 1501483 (SEQ ID NO: 476), CeresAnnot:8755079 (SEQ ID NO: 478), GI:115470147 (SEQ ID NO: 479), GI:15240905 (SEQ ID NO: 480), CeresAnnot:8755085 (SEQ ID NO: 482), GI:147853446 (SEQ ID NO: 483), GI:157346087 (SEQ ID NO: 484), CeresAnnot:1538867 (SEQ ID NO: 486), CeresAnnot:8755091 (SEQ ID NO: 488), CeresAnnot: 1492702 (SEQ ID NO: 490), CeresClone:325604 (SEQ ID NO: 492), GI:108707040 (SEQ ID NO: 493), CeresAnnot: 1302517_At (SEQ ID NO: 495), CeresAnnot:1355964 (SEQ ID NO: 497), CeresAnnot:8755104 (SEQ ID NO: 499), GI:147802380 (SEQ ID NO: 500), GI:510238 (SEQ ID NO: 501), GI:157341962 (SEQ ID NO: 502), GI:6635838 (SEQ ID NO: 503), GI:4455276 (SEQ ID NO: 504), CeresAnnot:8642246 (SEQ ID NO: 506), CeresAnnot: 8633032 (SEQ ID NO: 508), GI:157337654 (SEQ ID NO: 509), CeresAnnot:8642241 (SEQ ID NO: 511), CeresAnnot: 1520085 (SEQ ID NO: 513), CeresAnnot:1514979 (SEQ ID NO: 515), GI:147858202 (SEQ ID NO: 516), GI:125545538 (SEQ ID NO: 517), GI:115451771 (SEQ ID NO: 518), GI:125587732 (SEQ ID NO: 519), CeresAnnot:1516968 (SEQ ID NO: 521), CeresClone:350844 (SEQ ID NO: 523), CeresAnnot:8658700 (SEQ ID NO: 525), GI:157346088 (SEQ ID NO: 526), CeresClone:1926916 (SEQ ID NO: 528). GI:15226861 (SEQ ID NO: 529), CeresClone:816960 (SEQ ID NO: 531), GI:15232435 (SEQ ID NO: 532), CeresAnnot:8643789 (SEQ ID NO: 534), CeresAnnot: 8631367 (SEQ ID NO: 536), GI:157339093 (SEQ ID NO: 537), CeresAnnot:8633031 (SEQ ID NO: 539), GI:125543029 (SEQ ID NO: 540), GI:115454995 (SEQ ID NO: 541), CeresAnnot:8755090 (SEQ ID NO: 543), CeresAnnot:8755097 (SEQ ID NO: 545), CeresAnnot:8755098 (SEQ ID NO: 547), CeresAnnot:8755099 (SEQ ID NO: 549), (SEQ ID NO: 550), (SEQ ID NO: 551), (SEQ ID NO: 552), CeresAnnot: 6086224 (SEQ ID NO:693), CeresClone: 476769 (SEQ ID NO:695), or CeresClone:15650 (SEQ ID NO:697). In some cases, a functional homolog of SEQ ID NO: 426 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 426.

The identification of conserved regions in a biomass-modulating polypeptide facilitates production of variants of biomass-modulating polypeptides. Variants of biomass-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, FIG. 4, FIG. 5, FIG. 6, FIG. 7, FIG. 8, FIG. 9, FIG. 10, or FIG. 11 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful biomass-modulating polypeptides include those that fit a Hidden Markov Model based on the polypeptides set forth in any one of FIGS. 1-11. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, - -consistency REPS of 2; -ir, - -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate biomass-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The biomass-modulating polypeptides discussed below fit the indicated HMM with an HMM bit score greater than to 65. (e.g., greater than 70, 80, 90, 100, 120, 140, 200, 300, 500, 1000, 1500, or 2000). In some embodiments, the HMM bit score of a biomass-modulating polypeptide discussed below is about 50%, 60%, 70%, 80%, 90%, or 95% of the HMM bit score of a functional homolog provided in the Sequence Listing of this application. In some embodiments, a biomass-modulating polypeptide discussed below fits the indicated HMM with an HMM bit score greater than 210, and has a domain indicative of a biomass-modulating polypeptide. In some embodiments, a biomass-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-11.

Examples of polypeptides are shown in the sequence listing that have HMM bit scores greater than 130 when fitted to an HMM generated from the amino acid sequences set forth in FIG. 1 are identified in the Sequence Listing of this application. Such polypeptides include, for example, SEQ ID NOs: 554, 556, 558, 560, 562, 563, 565, 567, 569, 571, 573, 574, 575, 577, 579, 581, 583, 585, 587, 589, 591, or 593.

Examples of polypeptides are shown in the sequence listing that have HMM bit scores greater than 340 when fitted to an HMM generated from the amino acid sequences set forth in FIG. 2 are identified in the Sequence Listing of this application. Such polypeptides include, for example, SEQ ID NOs: 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, or 321.

Examples of polypeptides are shown in the sequence listing that have HMM bit scores greater than 530 when fitted to an HMM generated from the amino acid sequences set forth in FIG. 3 are identified in the Sequence Listing of this application. Such polypeptides include, for example, SEQ ID NOs: 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, or 207.

Examples of polypeptides are shown in the sequence listing that have HMM bit scores greater than 120 when fitted to an HMM generated from the amino acid sequences set forth in FIG. 4 are identified in the Sequence Listing of this application. Such polypeptides include, for example, SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, or 75.

Examples of polypeptides are shown in the sequence listing that have HMM bit scores greater than 635 when fitted to an HMM generated from the amino acid sequences set forth in FIG. 5 are identified in the Sequence Listing of this application. Such polypeptides include, for example, SEQ ID NOs: 645, 647, 649, 651, 652, 653, 655, 657, 659, 660, 662, 664, 666, 667, 669, 670, 671, 672, 673, 674, 675, 676, 677, or 689.

Examples of polypeptides are shown in the sequence listing that have HMM bit scores greater than 65 when fitted to an HMM generated from the amino acid sequences set forth in FIG. 6 are identified in the Sequence Listing of this application. Such polypeptides include, for example, SEQ ID NOs: 255, 257, 259, or 261.

Examples of polypeptides are shown in the sequence listing that have HMM bit scores greater than 100 when fitted to an HMM generated from the amino acid sequences set forth in FIG. 7 are identified in the Sequence Listing of this application. Such polypeptides include, for example, SEQ ID NOs: 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, or 424.

Examples of polypeptides are shown in the sequence listing that have HMM bit scores greater than 480 when fitted to an HMM generated from the amino acid sequences set forth in FIG. 8 are identified in the Sequence Listing of this application. Such polypeptides include, for example, SEQ ID NOs: 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, or 691.

Examples of polypeptides are shown in the sequence listing that have HMM bit scores greater than 145 when fitted to an HMM generated from the amino acid sequences set forth in FIG. 9 are identified in the Sequence Listing of this application. Such polypeptides include, for example, SEQ ID NOs: 77, 79, 81, 82, 84, 86, 87, 88, 90, 92, 94, 96, 98, 100, 102, 104, 106, 108, 110, 112, 114, or 115.

Examples of polypeptides are shown in the sequence listing that have HMM bit scores greater than 280 when fitted to an HMM generated from the amino acid sequences set forth in FIG. 10 are identified in the Sequence Listing of this application. Such polypeptides include, for example, SEQ ID NOs: 209, 210, 212, 214, 216, 218, 220, 222, 224, 226, 228, 230, 232, 234, 236, 238, 239, 241, 242, 243, 244, 245, 246, 247, 248, 249, 250, or 251.

Examples of polypeptides are shown in the sequence listing that have HMM bit scores greater than 1000 when fitted to an HMM generated from the amino acid sequences set forth in FIG. 11 are identified in the Sequence Listing of this application. Such polypeptides include, for example, SEQ ID NOs: 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 693, 695, or 697.

D. Percent Identity

In some embodiments, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483,484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697. Polypeptides having such a percent sequence identity often have a domain indicative of a biomass-modulating polypeptide and/or have an HMM bit score that is greater than 65, as discussed above. Amino acid sequences of biomass-modulating polypeptides having at least 80% sequence identity to one of the amino acid sequences set forth in SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483,484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697 are provided in FIGS. 1-11 and in the Sequence Listing.

"Percent sequence identity" refers to the degree of sequence identity between any given reference sequence, e.g., SEQ ID NO: 1, and a candidate biomass-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a biomass-modulating polypeptide has an amino acid sequence with at least 45% sequence identity, e.g., 50%, 52%, 56%, 59%. 61%, 65%, 70%, 75%, 80%, 85%, 90%, 95%, 97%, 98%, or 99% sequence identity, to the amino acid sequence set forth in SEQ ID NO: 554. Amino acid sequences of polypeptides having greater than 45% sequence identity to the polypeptide set forth in SEQ ID NO: 554 are provided in FIG. 1 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 263. Amino acid sequences of polypeptides having greater than 45% sequence identity to the polypeptide set forth in SEQ ID NO: 263 are provided in FIG. 2 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 117. Amino acid sequences of polypeptides having greater than 45% sequence identity to the polypeptide set forth in SEQ ID NO: 117 are provided in FIG. 3 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1. Amino acid sequences of polypeptides having greater than 45% sequence identity to the polypeptide set forth in SEQ ID NO: 1 are provided in FIG. 4 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 645. Amino acid sequences of polypeptides having greater than 45% sequence identity to the polypeptide set forth in SEQ ID NO: 645 are provided in FIG. 5 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 253. Amino acid sequences of polypeptides having greater than 45% sequence identity to the polypeptide set forth in SEQ ID NO: 253 are provided in FIG. 6 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 323. Amino acid sequences of polypeptides having greater than 45% sequence identity to the polypeptide set forth in SEQ ID NO: 323 are provided in FIG. 7 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 595. Amino acid sequences of polypeptides having greater than 45% sequence identity to the polypeptide set forth in SEQ ID NO: 595 are provided in FIG. 8 and in the Sequence Listing.

In some cases, a biomass-modulating polypeptide has an amino acid sequence with at least 45% sequence identity, e.g., 50%, 52%, 56%, 59%. 61%, 65%, 70%, 75%, 80%, 85%, 90%, 95%, 97%, 98%, or 99% sequence identity, to the amino acid sequence set forth in SEQ ID NO: 77. Amino acid sequences of polypeptides having greater than 45% sequence identity to the polypeptide set forth in SEQ ID NO: 77 are provided in FIG. 9 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 209. Amino acid sequences of polypeptides having greater than 45% sequence identity to the polypeptide set forth in SEQ ID NO: 209 are provided in FIG. 10 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 426. Amino acid sequences of polypeptides having greater than 45% sequence identity to the polypeptide set forth in SEQ ID NO: 426 are provided in FIG. 11 and in the Sequence Listing.

E. Other Sequences

It should be appreciated that a biomass-modulating polypeptide can include additional amino acids that are not involved in biomass modulation, and thus such a polypeptide can be longer than would otherwise be the case. For example, a biomass-modulating polypeptide can include a purification tag, a chloroplast transit peptide, a mitochondrial transit peptide, an amyloplast peptide, or a leader sequence added to the amino or carboxy terminus. In some embodiments, a biomass-modulating polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate biomass levels when transcribed in a plant or plant cell. Such nucleic acids include, without limitation, those that encode a biomass-modulating polypeptide and those that can be used to inhibit expression of a biomass-modulating polypeptide via a nucleic acid based method.

A. Nucleic Acids Encoding Biomass-Modulating Polypeptides

Nucleic acids encoding biomass-modulating polypeptides are described herein. Examples of such nucleic acids include SEQ ID NOs: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696.

A biomass-modulating nucleic acid can comprise the nucleotide sequence set forth in SEQ ID NO: 553. Alternatively, a biomass-modulating nucleic acid can be a variant of the nucleic acid having the nucleotide sequence set forth in SEQ ID NO: 553. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 553.

A biomass-modulating nucleic acid can comprise the nucleotide sequence set forth in SEQ ID NO: 262. Alternatively, a biomass-modulating nucleic acid can be a variant of the nucleic acid having the nucleotide sequence set forth in SEQ ID NO: 262. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 262.

A biomass-modulating nucleic acid can comprise the nucleotide sequence set forth in SEQ ID NO: 116. Alternatively, a biomass-modulating nucleic acid can be a variant of the nucleic acid having the nucleotide sequence set forth in SEQ ID NO: 116. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 116.

A biomass-modulating nucleic acid can comprise the nucleotide sequence set forth in SEQ ID NO: 678. Alternatively, a biomass-modulating nucleic acid can be a variant of the nucleic acid having the nucleotide sequence set forth in SEQ ID NO: 678. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 678.

A biomass-modulating nucleic acid can comprise the nucleotide sequence set forth in SEQ ID NO: 644. Alternatively, a biomass-modulating nucleic acid can be a variant of the nucleic acid having the nucleotide sequence set forth in SEQ ID NO: 644. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 644.

A biomass-modulating nucleic acid can comprise the nucleotide sequence set forth in SEQ ID NO: 252. Alternatively, a biomass-modulating nucleic acid can be a variant of the nucleic acid having the nucleotide sequence set forth in SEQ ID NO: 252. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 252.

A biomass-modulating nucleic acid can comprise the nucleotide sequence set forth in SEQ ID NO: 322. Alternatively, a biomass-modulating nucleic acid can be a variant of the nucleic acid having the nucleotide sequence set forth in SEQ ID NO: 322. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 322.

A biomass-modulating nucleic acid can comprise the nucleotide sequence set forth in SEQ ID NO: 594. Alternatively, a biomass-modulating nucleic acid can be a variant of the nucleic acid having the nucleotide sequence set forth in SEQ ID NO: 594. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 594.

A biomass-modulating nucleic acid can comprise the nucleotide sequence set forth in SEQ ID NO: 76. Alternatively, a biomass-modulating nucleic acid can be a variant of the nucleic acid having the nucleotide sequence set forth in SEQ ID NO: 76. For example, a biomass-modulating nucleic acid can have a nucleotide sequence with at least 80% sequence identity, e.g., 81%, 85%, 90%, 95%. 97%, 98%, or 99% sequence identity, to the nucleotide sequence set forth in SEQ ID NO: 76.

A biomass-modulating nucleic acid can comprise the nucleotide sequence set forth in SEQ ID NO: 208. Alternatively, a biomass-modulating nucleic acid can be a variant of the nucleic acid having the nucleotide sequence set forth in SEQ ID NO: 208. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 208.

A biomass-modulating nucleic acid can comprise the nucleotide sequence set forth in SEQ ID NO: 425. Alternatively, a biomass-modulating nucleic acid can be a variant of the nucleic acid having the nucleotide sequence set forth in SEQ ID NO: 425. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 425.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Biomass-Modulating Polypeptide A nucleic acid encoding one of the biomass-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular biomass-modulating polypeptide; i.e., for many amino acids, there is more than one nucleotide triplet that serves as the codon for the amino acid. Thus, codons in the coding sequence for a given biomass-modulating polypeptide can be modified such that optimal expression in a particular plant species is obtained, using appropriate codon bias tables for that species.

In some cases, expression of a biomass-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Biomass-Modulating Polypeptide

Polynucleotides and recombinant constructs described herein can be used to inhibit expression of a biomass-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding biomass-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a biomass-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the biomass-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a biomass-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the biomass-modulating polypeptide. In other embodiments, one strand of the stem portion of a double stranded RNA comprises a sequence that is similar or identical to the sequence of an intron, or a fragment thereof, in the pre-mRNA encoding a biomass-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a biomass-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a biomass-modulating polypeptide, or a fragment of such sequences. In some embodiments, the sense or antisense sequence is identical or complementary to a sequence of the regulatory region that drives transcription of the gene encoding a biomass-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a biomass-modulating polypeptide described herein. The sense sequence complementary to the antisense sequence can be a sequence present within the mRNA of the biomass-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate biomass levels. A recombinant nucleic acid construct can comprise a nucleic acid encoding a biomass-modulating polypeptide as described herein, operably linked to a regulatory region suitable for expressing the biomass-modulating polypeptide in the plant or cell. Thus, a nucleic acid can comprise a coding sequence that encodes a biomass-modulating polypeptides as set forth in SEQ ID NOs: 1, 2, 4, 6, 8, 10, 11, 12, 13, 14, 15, 16, 17, 18, 20, 22, 24, 25, 27, 29, 30, 32, 33, 34, 36, 37, 38, 39, 40, 41, 43, 45, 47, 49, 50, 51, 53, 54, 56, 58, 59, 61, 63, 64, 66, 68, 70, 71, 72, 74, 75, 77, 79, 81, 82, 84, 86, 87, 88, 90, 92, 94, 96, 98, 100, 102, 104, 106, 108, 110, 112, 114, 115, 117, 118, 120, 121, 122, 123, 125, 127, 129, 131, 132, 133, 135, 137, 139, 141, 142, 144, 145, 146, 147, 149, 151, 152, 153, 154, 155, 156, 158, 160, 162, 163, 164, 166, 168, 169, 171, 173, 174, 176, 178, 180, 182, 184, 185, 186, 188, 189, 190, 191, 193, 194, 195, 196, 198, 200, 202, 203, 204, 206, 207, 209, 210, 212, 214, 216, 218, 220, 222, 224, 226, 228, 230, 232, 234, 236, 238, 239, 241, 242, 243, 244, 245, 246, 247, 248, 249, 250, 251, 253, 255, 257, 259, 261, 263, 264, 266, 268, 269, 271, 273, 275, 276, 278, 279, 281, 282, 283, 285, 287, 289, 291, 292, 294, 295, 296, 297, 298, 299, 300, 302, 304, 305, 306, 308, 310, 311, 312, 314, 315, 317, 319, 320, 321, 323, 324, 326, 327, 329, 331, 332, 334, 336, 337, 338, 340, 342, 343, 345, 347, 349, 351, 353, 354, 356, 357, 359, 361, 363, 365, 367, 369, 371, 372, 374, 376, 378, 380, 382, 384, 386, 388, 390, 391, 393, 395, 397, 399, 401, 403, 405, 406, 407, 409, 411, 413, 415, 416, 417, 418, 420, 421, 422, 424, 426, 428, 429, 430, 431, 433, 435, 436, 437, 438, 439, 440, 442, 444, 446, 447, 448, 449, 450, 452, 453, 454, 455, 456, 457, 459, 461, 463, 464, 466, 467, 468, 470, 472, 474, 476, 478, 479, 480, 482, 483, 484, 486, 488, 490, 492, 493, 495, 497, 499, 500, 501, 502, 503, 504, 506, 508, 509, 511, 513, 515, 516, 517, 518, 519, 521, 523, 525, 526, 528, 529, 531, 532, 534, 536, 537, 539, 540, 541, 543, 545, 547, 549, 550, 551, 552, 554, 556, 558, 560, 562, 563, 565, 567, 569, 571, 573, 574, 575, 577, 579, 581, 583, 585, 587, 589, 591, 593, 595, 597, 598, 600, 602, 603, 604, 605, 606, 608, 609, 610, 611, 613, 615, 616, 618, 619, 620, 622, 623, 625, 627, 629, 630, 632, 633, 634, 636, 637, 638, 639, 641, 642, 643, 645, 647, 649, 651, 652, 653, 655, 657, 659, 660, 662, 664, 666, 667, 669, 670, 671, 672, 673, 674, 675, 676, 677, 689, 691, 693, 695, or 697. Examples of nucleic acids encoding biomass-modulating polypeptides are set forth in SEQ ID NO: 3, 5, 7, 9, 19, 21, 23, 26, 28, 31, 35, 42, 44, 46, 48, 52, 55, 57, 60, 62, 65, 67, 69, 73, 76, 78, 80, 83, 85, 89, 91, 93, 95, 97, 99, 101, 103, 105, 107, 109, 111, 113, 116, 119, 124, 126, 128, 130, 134, 136, 138, 140, 143, 148, 150, 157, 159, 161, 165, 167, 170, 172, 175, 177, 179, 181, 183, 187, 192, 197, 199, 201, 205, 208, 211, 213, 215, 217, 219, 221, 223, 225, 227, 229, 231, 233, 235, 237, 240, 252, 254, 256, 258, 260, 262, 265, 267, 270, 272, 274, 277, 280, 284, 286, 288, 290, 293, 301, 303, 307, 309, 313, 316, 318, 322, 325, 328, 330, 333, 335, 339, 341, 344, 346, 348, 350, 352, 355, 358, 360, 362, 364, 366, 368, 370, 373, 375, 377, 379, 381, 383, 385, 387, 389, 392, 394, 396, 398, 400, 402, 404, 408, 410, 412, 414, 419, 423, 425, 427, 432, 434, 441, 443, 445, 451, 458, 460, 462, 465, 469, 471, 473, 475, 477, 481, 485, 487, 489, 491, 494, 496, 498, 505, 507, 510, 512, 514, 520, 522, 524, 527, 530, 533, 535, 538, 542, 544, 546, 548, 553, 555, 557, 559, 561, 564, 566, 568, 570, 572, 576, 578, 580, 582, 584, 586, 588, 590, 592, 594, 596, 599, 601, 607, 612, 614, 617, 621, 624, 626, 628, 631, 635, 640, 644, 646, 648, 650, 654, 656, 658, 661, 663, 665, 668, 678, 679, 680, 681, 682, 683, 684, 685, 686, 687, 688, 690, 692, 694, or 696, or in the Sequence Listing. The biomass-modulating polypeptide encoded by a recombinant nucleic acid can be a native biomass-modulating polypeptide, or can be heterologous to the cell. In some cases, the recombinant construct contains a nucleic acid that inhibits expression of a biomass-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen™ (Madison, WI), Clontech™ (Palo Alto, CA), Stratagene™ (La Jolla, CA), and Invitrogen/Life Technologies™ (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/U.S. Ser. No. 05/034,343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao, *Plant Mol. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell,* 3(10):1051-1061 (1991)), the *Commelina* yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

ix. Inducible Promoters

Inducible promoters confer transcription in response to external stimuli such as chemical agents or environmental stimuli. For example, inducible promoters can confer transcription in response to hormones such as gibberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, P70829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a biomass-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a biomass-modulating polypeptide or nucleic acid. Physical and biochemical methods can be used to identify expression levels. These include Southern analysis or PCR amplification for detection of a polynucleotide; Northern blots. S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of biomass. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a biomass level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amarvilidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Enythroxylaceae, Euphorbiaceae, Fabaceae, Lamiaceae, Linaceae, Lycopodiaceae, Malvaceae, Melanthiaceae, Musaceae, Myrtaceae, Nvssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abebnoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (cucalyptus), *Triticosecale* (triticum-wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash). *Cucurbita moschata* (squash). *Spinacea oleracea* (spinach), *Citrullus lanatus* (watermelon), *Abelmoschus esculentus* (okra), and *Solanum melongena* (eggplant).

Suitable species also include *Papaver somnijerum* (opium poppy), *Papaver orientale, Taxus baccata, Taxus brevijblia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa helladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum (Huperzia serrata), Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemi-* cum, *Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatun, Pennisetum polystachion, Pennisetum polystachion* ssp. *Setosum, Pennisetum purpureum, Pennisetum setaceun, Pennisetum subangustum, Pennisetum typhoides, Pennisetum villosum*, or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus* x *giganteus, Miscanthus sinensis, Miscanthus* x *ogiformis, Miscanthus floridulus, Miscanthus transmorrisonensis, Miscanthus oligostachyus, Miscanthus nepalensis, Miscanthus sacchariflorus, Miscanthus* x *giganteus* 'Amuri', *Miscanthus* x *giganteus* 'Nagara', *Miscanthus* x *giganteus* 'Illinois', *Miscanthus sinensis* var. 'Goliath'. *Miscanthus sinensis* var. 'Roland', *Miscanthus sinensis* var. 'Africa', *Miscanthus sinensis* var. 'Fern Osten', *Hiscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan'. *Miscanthus* var. 'Dixieland', *Miscanthus* var. 'Gilded Tower' (U.S. Pat. No. PP14,743), *Miscanthus* var. 'Gold Bar' (U.S. Pat. No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. PP13, 008), *Miscanthus* var. 'Lottum', *Miscanthus* var. 'Malepartus', *Miscanthus* var. 'Morning Light', *Miscanthus* var. 'Mysterious Maiden' (U.S. Pat. No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen'(aka 'Little Dot'), *Miscanthus* var. 'Rigoletto', *Miscanthus* var. 'Sarabande', *Miscanthus* var. 'Silberpfeil' (aka. Silver Arrow), *Afiscanthus* var. 'Silverstripe', *Miscanthus* var. 'Super Stripe' (U.S. Pat. No. PP18, 161), *Miscanthus* var. 'Strictus', or *Miscanthus* var. 'Zebrinus'.

In some embodiments, a suitable species can be a wild, weedy, or cultivated *Sorghum* species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exsans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x sudangrass or *Sorghum* x *drummondii*.

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale. Triticum*, and *Zea*. In some embodiments, a plant is a member of the species *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossipum hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. X *Miscanthus* sp., *Sorghum* sp. X *Miscanthus* sp., e.g., *Panicum virgatum* x *Panicum amarum, Panicum virgatum* x *Panicum amarulum*, and *Pennisetum purpureum* x *Pennisetum typhoidum*).

D. Transgenic Plant Phenotypes

In some embodiments, a plant in which expression of a biomass-modulating polypeptide is modulated can have increased levels of biomass in plants. For example, a biomass-modulating polypeptide described herein can be expressed in a transgenic plant, resulting in increased levels of vegetative tissue. The biomass level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the biomass level in a corresponding control plant that does not express the transgene. In some embodiments, a plant in which expression of a biomass-modulating polypeptide is modulated can have decreased levels of seed production. The level can be decreased by at least 2 percent, e.g., 2, 3, 4, 5, 10, 15, 20, 25, 30, 35, or more than 35 percent, as compared to the seed production level in a corresponding control plant that does not express the transgene.

Increases in seed production in such plants can provide improved nutritional availability in geographic locales where intake of plant foods is often insufficient, or for biofuel production. In some embodiments, decreases in biomass in such plants can be useful in situations where vegetative tissues are not the primary plant part that is harvested for human or animal consumption (i.e., seeds are harvested).

In some embodiments, a plant in which expression of a biomass-modulating polypeptide is modulated can have increased or decreased levels of biomass in one or more plant tissues, e.g., vegetative tissues, reproductive tissues, or root tissues. For example, the biomass level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the biomass level in a corresponding control plant that does not express the transgene. In some embodiments, a plant in which expression of a biomass-modulating polypeptide is modulated can have decreased levels of biomass in one or more plant tissues. The biomass level can be decreased by at least 2 percent, e.g., 2, 3, 4, 5, 10, 15, 20, 25, 30, 35, or more than 35 percent, as compared to the biomass level in a corresponding control plant that does not express the transgene.

Increases in biomass in such plants can provide improved food quantity, or improved energy production. Decreases in biomass can provide more efficient partitioning of nutrients to plant part(s) that are harvested for human or animal consumption.

Typically, a difference in the amount of biomass in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of biomass is statistically significant at $p<0.01$, $p<0.005$, or $p<0.001$. A statistically significant difference in, for example, the amount of biomass in a transgenic plant compared to the amount of a control plant indicates that the recombinant nucleic acid present in the transgenic plant results in altered biomass levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots. SI RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be measured as described in the examples section. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. $DMY=((100-M)/100)*FMW$. Biomass can be quantified as fresh matter yield, which is the mass of biomass produced (usually reported in T/acre) on an as-received basis, which includes the weight of moisture.

V. MODIFYING ENDOGENOUS NUCLEIC ACIDS ENCODING BIOMASS-MODULATING POLYPEPTIDES

This document also features plant cells and plants in which an endogenous biomass-modulating nucleic acid described herein has been modified (e.g., a regulatory region, intron, or coding region of the biomass-modulating nucleic acid has been modified). The biomass of such plants is altered relative to the corresponding level of a control plant in which the endogenous nucleic acid is not modified. Such plants are referred to herein as modified plants and may be used to produce, for example, increased amounts of biomass.

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.*, 57:747-757 (2009); and Lloyd et al., *Proc. Natl. Acad. Sci. USA*, 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA*, 106(5): 1660-1665 (2009); and Li et al., *Proc Natl Acad Sci USA*, 103(46):17337-42 (2006).

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology*, 122:1003-1013 (2000).

In some embodiments, endogenous nucleic acids can be modified by introducing an engineered transcription activation/repression factor (e.g., zinc finger protein transcription factor, or ZFP TF. See, for example, the world wide web at sangamo.com/tech/tech_plat_over.html #whatarezfp). An engineered transcription activation/repression factor (such as ZFP TF) can activate, repress, or switch the target endogenous biomass gene expression by binding specifically to the promoter region or coding region of the endogenous gene.

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet* 5(2):145-50 (2004).

In some embodiments, an endogenous nucleic acid can be modified via a gene silencing technique. See, for example, the section herein regarding "Inhibition of Expression of a Biomass-Modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of biomass. For example, a population of progeny can be screened for those plants having a desired level of expression of a biomass-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in a biomass level relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous biomass-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in biomass.

As with transgenic plant cells, modified plant cells can constitute part or all of a whole plant. Such plants can be grown in the same manner as described for transgenic plants and can be bred or propagated in the same manner as described for transgenic plants.

VI. PLANT BREEDING

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen™ or OliGreen™) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under IV light (e.g., Ethidium bromide, GR Safe, SYBR™ Green, or SYBR™ Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, U. H. Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR™ Green), or a fluorophore-containing DNA probe, such as single-stranded oligonucleotides covalently bound to a fluorescent reporter or fluorophore (e.g. 6-carboxyfluorescein or tetrachlorofluorescein) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, NY, USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., PstI). The digested DNA can be separated by size on a preparative gel. Polynucleotide fragments (500 to 2000 bp)

can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in the biomass trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VII. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher biomass yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VIII. EXAMPLES

Example 1—Transgenic Rice Plants

The following symbols are used in with respect to rice transformation: $T_0$: plant regenerated from transformed tissue culture, $T_1$: first generation progeny of self-pollinated $T_0$ plants; $T_2$: second generation progeny of self-pollinated $T_1$ plants; $T_3$: third generation progeny of self-pollinated $T_2$ plants.

The following is a list of nucleic acids that were isolated from *Arabidopsis thaliana* plants: CeresAnnot: 544549 (SEQ ID NO:262), CeresAnnot: 1355066 (SEQ ID NO:116). CeresClone: 1356785 (SEQ ID NO:252), CeresClone: 26006 (SEQ ID NO:594), CeresClone: 4831 (SEQ ID NO:76), CeresAnnot: 847799 (SEQ ID NO:208), and CeresAnnot: 878355 (SEQ ID NO:425). The following nucleic acids were isolated from *Zea mays* plants: CeresClone: 1384304 (SEQ ID NO:553). The following nucleic acids were isolated from *Oryza sativa* plants: antisense sequence (SEQ ID NO:678). CeresClone: 638126 (SEQ ID NO:322) was isolated from *Glycine max* plants.

Each isolated nucleic acid described above was cloned into a Ti plasmid vector containing a phosphinothricin acetyltransferase gene which confers Finale™ resistance to transformed plants. Constructs were made using the above mentioned nucleic acids that contained each operably linked to a 326 promoter construct was introduced into callus cells of the rice cultivar Kitaake by an *Agrobacterium*-mediated transformation protocol. Approximately 20-30 independent $T_0$ transgenic plants were generated from each transformation, as well as for the control plasmid (empty vector). Preliminary phenotypic analysis indicated that $T_0$ transformants did not show any significant phenotypic anomalies in vegetative organs, with a few exceptions where some plants appeared small with reduced fertility, most likely due to tissue culture effects.

$T_0$ plants were grown in a greenhouse, allowed to self-pollinate, and $T_1$ seeds collected. $T_1$ and $T_2$ plants were grown in a field. The presence of each construct was confirmed by PCR.

Rice seeds were soaked for 3-4 days before spring germination and transplanted to the field about one month later in Langfang, China. The distance between rows was 25 cm and the distance between plants was 15 cm. The combined fertilizer (16N-16P-16K) was applied at 25 kg/mu (666.7 m$^2$) just before transplanting. 12.5 kg/mu of urea was applied at two times during the growing season prior to panicle development.

Ten plants were grown per transgenic event within one row. Only those rows that were visibly different from control plants were measured. Plant height was measured at maturity.

Biomass (Dry weight) measurements for CW00733, CW00710, CW00628, CW00604, CW00564, CW00469, and CW00536 were collected from T$_1$ plants that were grown. The stems with leaves and leaf sheaths but without panicles were dried in a greenhouse for at least a month, and then weighed for each plant (all tillers weighed together for each plant). Measurements for CW00191. CW00297, and CW00319 were collected from T$_2$ plants that were grown.

The stems with leaves and leaf sheaths but with panicles separated were dried in a room for at least a month, and then weighed for each plant (all tillers weighed together for each plant). Tiller number was counted after 4 months of growth.

Example 2—Results for Rice Events CW00733, Ceres Clone:1384304, (SEQ ID NO: 553)

T$_1$ seed from one event of CW00733 containing Ceres-Clone:1384304 was analyzed as described in Example 1. The plant height, biomass, and panicle weight of transgenic T$_1$ plants in comparison to plants not containing the transgene grown at the same location is shown in Table 1. Each table data row corresponds to a field row. The data points represent an average of 10 transgenic plants (1 row of same event) and an average of 40 control plants (4 rows). An increase in biomass, height and panicle weight was shown in comparison to plants not containing the transgene.

TABLE 1

| Plant Height (cm) | | Biomass (g)/plant | | Panicle wt (g)/plant | |
|---|---|---|---|---|---|
| Control | Transgenic | Control | Transgenic | Control | Transgenic |
| 72.41 | 80.30 | 16.70 | 27.45 | 21.56 | 28.89 |
| | | | | 24.58 | 23.42 |

The plant height (cm), yield (measured as g/per panicles of 16 plants), and biomass (measured as g of stem only (no inflorescence or root)) of transgenic T$_2$ CW00733 plants in comparison to plants not containing the transgene grown (WT) at the same location are shown in Table 2. Results from CW00604 events (Example 7) also are shown in Table 2. An increase in height and biomass was observed.

TABLE 2

| | T2 Plants from CW00733 and CW00604 events | | | |
|---|---|---|---|---|
| | Rep | WT | CW00604 | CW00733 |
| Height (cm) | Rep I | 80.3 | 81.3 | 85.0 |
| | Rep II | 73.3 | 79.7 | 84.5 |
| | Rep III | 77.2 | 79.1 | 82.9 |
| | Average | 76.9 | 80.0 | 84.1 |
| Yield | Rep I | 395.4 | 357.0 | 356.8 |
| | Rep II | 385.0 | 324.0 | 348.5 |
| | Rep III | 361.6 | 309.0 | 345.3 |
| | Average | 380.7 | 330.0 | 350.2 |

TABLE 2-continued

| | T2 Plants from CW00733 and CW00604 events | | | |
|---|---|---|---|---|
| | Rep | WT | CW00604 | CW00733 |
| Biomass | Rep I | 16.6 | 24.8 | 19.3 |
| | Rep II | 20.0 | 20.8 | 17.7 |
| | Rep III | 16.6 | 19.8 | 19.7 |
| | Average | 17.7 | 21.8 | 18.9 |

Example 3—Results for Rice Events CW00319, Ceres Annot: 544549 (SEQ ID NO: 262)

Biomass from plants grown from T$_2$ and T$_3$ seed from one event of CW00319 containing Ceres Annot: 544549 was analyzed as described in Example 1. The average biomass of transgenic T$_2$ and T$_3$ plants in comparison to plants not containing the transgene grown at the same location is shown in Table 3. The low nitrogen plots and control plots were each replicated 3 times in randomized block design, having transgenic plants representing multiple events and controls. Each plot contained 40 plants. Ten plants were measured per plot for one event of CW00319. Each of the biomass values presented in Table 3 represents an average of 30 plants measured. The results show a measured increase in biomass for transgenic plants under low nitrogen conditions in comparison to plants not containing the transgene.

TABLE 3

| Biomass (g)/plant (normal) | | Biomass (g)/plant (Low N) | |
|---|---|---|---|
| Control | Transgenic | Control | Transgenic |
| 14.6 | 14.38 | 16.01 | 17.44 |

Example 4—Results for Rice Events CW00710, Ceres Annot: 1355066 (SEQ ID NO: 116)

T$_1$ seed from one event of CW00710 containing Ceres Annot: 1355066 was analyzed as described in Example 1. The plant height, biomass, and panicle weight of transgenic T$_1$ plants in comparison to plants not containing the transgene grown at the same location is shown in Table 4. The table data row corresponds to a field row. The data points represent an average of 10 transgenic plants (1 row of same event) and an average of 40 control plants (4 rows). An increase in biomass and height was shown in comparison to plants not containing the transgene.

TABLE 4

| Plant Height (cm) | | Biomass (g)/plant | | Panicle wt (g)/plant | |
|---|---|---|---|---|---|
| Control | Transgenic | Control | Transgenic | Control | Transgenic |
| 72.20 | 85.60 | 14.51 | 24.15 | 19.38 | 18.70 |

Example 5—Results for Rice Events CW00628 (SEQ ID NO: 678)

T$_1$ seed from one event of CW00628 containing SEQ ID NO: 678 RNAi construct was analyzed as described in Example 1. The plant height, biomass, and panicle weight of transgenic T$_1$ plants in comparison to plants not containing the transgene grown at the same location is shown in Table 5. The table data row corresponds to a field row. The data points represent an average of 10 transgenic plants (1 row of same event) and an average of 40 control plants (4 rows). An increase in biomass and height was shown in comparison to plants not containing the transgene.

TABLE 5

| Plant Height (cm) | | Biomass (g)/plant | | Panicle wt (g)/plant | |
|---|---|---|---|---|---|
| Control | Transgenic | Control | Transgenic | Control | Transgenic |
| 75.30 | 81.60 | 15.92 | 29.96 | 24.53 | 20.38 |

Example 6—Results for Rice Events CW00297, Ceres Clone: 625057 (SEQ ID NO: 644)

Biomass from plants grown from $T_2$ and $T_3$ seed from one event of CW00297 containing Ceres Clone: 625057 was analyzed as described in Example 1. The average biomass of transgenic $T_2$ and $T_3$ plants in comparison to plants not containing the transgene grown at the same location is shown in Table 6. The low nitrogen plots and control plots were each replicated 3 times in randomized block design, having transgenic plants representing multiple events and controls. Each plot contained 40 plants. Ten plants were measured per plot for one event of CW00297. Each of the biomass values presented in Table 6 represents an average of 30 plants measured. The results show a measured increase in biomass for transgenic plants under normal and low nitrogen conditions in comparison to plants not containing the transgene.

TABLE 6

| Biomass (g)/plant (normal) | | Biomass (g)/plant (Low N) | |
|---|---|---|---|
| Control | Transgenic | Control | Transgenic |
| 14.6 | 15.93 | 16.01 | 17.35 |

Example 7—Results for Rice Events CW00604, Ceres Clone: 1356785 (SEQ ID No:252)

$T_1$ seed from one event of CW00604 containing Ceres Clone: 1356785 was analyzed as described in Example 1. The plant height, biomass, and panicle weight of transgenic $T_1$ plants in comparison to plants not containing the transgene grown at the same location is shown in Table 7. Each table data row corresponds to a field row. The data points represent an average of 10 transgenic plants (1 row of same event) and an average of 40 control plants (4 rows). An increase in biomass, height and panicle weight was shown in comparison to plants not containing the transgene. An increase in height and biomass also was observed for $T_2$ plants. See Table 2.

TABLE 7

| Plant Height (cm) | | Biomass (g)/plant | | Panicle wt (g)/plant | |
|---|---|---|---|---|---|
| Control | Transgenic | Control | Transgenic | Control | Transgenic |
| 72.53 | 81.25 | 16.40 | 28.68 | 22.21 | 29.91 |
| 73.70 | 82.30 | | | | |

Example 8—Results for Rice Events CW00564, Ceres Clone: 638126 (SEQ ID NO: 322)

$T_1$ seed from one event of CW00564 containing Ceres Clone: 638126 was analyzed as described in Example 1. The plant height, biomass, and panicle weight of transgenic $T_1$ plants in comparison to plants not containing the transgene grown at the same location is shown in Table 8. The table data row corresponds to a field row. The data points represent an average of 10 transgenic plants (1 row of same event) and an average of 40 control plants (4 rows). An increase in biomass, height, and panicle weight was shown in comparison to plants not containing the transgene.

TABLE 8

| Plant Height (cm) | | Biomass (g)/plant | | Panicle wt (g)/plant | |
|---|---|---|---|---|---|
| Control | Transgenic | Control | Transgenic | Control | Transgenic |
| 72.88 | 85.44 | 18.11 | 36.47 | 22.56 | 37.47 |

The plant height (cm), yield (measured as g/per panicles of 16 plants), and biomass (measured as g of stem only (no inflorescence or root)) of transgenic $T_2$ CW00564 plants in comparison to plants not containing the transgene grown (WT) at the same location are shown in Table 9. Results from CW00469 events (Example 10) also are shown in Table 9. An increase in height, yield, and biomass was observed.

TABLE 9

| | T2 Plants from CW00564 and CW00469 events | | | |
|---|---|---|---|---|
| | Rep | WT | CW00469 | CW00564 |
| Height (cm) | Rep I | 77.3 | 117.1 | 90.7 |
| | Rep II | 76.9 | 117.7 | 91.5 |
| | Rep III | 77.4 | 113.1 | 92.7 |
| | Average | 77.2 | 115.9 | 91.6 |
| Yield | Rep I | 356.9 | 426.0 | 406.8 |
| | Rep II | 343.2 | 378.8 | 423.6 |
| | Rep III | 366.7 | 398.0 | — |
| | Average | 355.6 | 400.9 | 415.2 |
| Biomass | Rep I | 17.1 | 29.7 | 25.2 |
| | Rep II | 15.1 | 26.5 | 25.1 |
| | Rep III | 14.6 | 27.1 | 24.4 |
| | Average | 15.6 | 27.7 | 24.9 |

Example 9—Results for Rice Events CW00010, Ceres Clone: 26006 (SEQ ID NO: 594)

$T_1$ seed from three events of CW00010 containing Ceres Clone: 26006 was analyzed as described in Example 1. The plant height, biomass, tiller number, flowering time, and panicle weight of transgenic $T_1$ plants in comparison to plants not containing the transgene grown at the same location is shown in Tables 10, 11, and 12. The data points represent an average of 10 transgenic plants (1 row of same event) and an average of 40 control plants (4 rows). An increase in biomass, height, tiller number, and panicle weight was shown in comparison to plants not containing the transgene.

TABLE 10

Event 1

| | Percent Increase | p value | Number of plants measured |
|---|---|---|---|
| Biomass | 9 | 0.307 | 11 |
| Plant Height | 7 | 0.028 | 11 |
| Tiller Number | 27 | 0.002 | 10 |
| Flowering Time | 10 | 0.048 | 11 |
| Panicle weight | 16 | 0.012 | 39 |

TABLE 11

Event 17

| | Percent Increase | P value | Number of plants measured |
|---|---|---|---|
| Plant Height | 3 | 0.004 | 7 |
| Tiller Number | 34 | | 1 |
| Panicle weight | 4 | 0.591 | 7 |

TABLE 12

Event 2

| | Percent Increase | p value | Number of plants measured |
|---|---|---|---|
| Plant Height | 2 | 0.007 | 15 |
| Tiller Number | 27 | 0.013 | 10 |
| Panicle weight | 16 | 0.011 | 14 |

Example 10—Results for Rice Events CW00469, Ceres Clone: 4831 (SEQ ID NO: 76)

$T_1$ seed from one event of CW00469 containing Ceres Clone: 4831 was analyzed as described in Example 1. The plant height, biomass, and panicle weight of transgenic $T_1$ plants in comparison to plants not containing the transgene grown at the same location is shown in Table 13. The table data row corresponds to a field row. The data points represent an average of 10 transgenic plants (1 row of same event) and an average of 40 control plants (4 rows). An increase in biomass, height, and panicle weight was shown in comparison to plants not containing the transgene. An increase in height, yield, and biomass was shown in $T_2$ plants (see Table 9).

TABLE 13

| Plant Height (cm) | | Biomass (g)/plant | | Panicle wt (g)/plant | |
|---|---|---|---|---|---|
| Control | Transgenic | Control | Transgenic | Control | Transgenic |
| 76.54 | 112.22 | 25.44 | 56.06 | 32.63 | 62.70 |

Example 11—Results for Rice Events CW00536, Ceres Annot: 847799 (SEQ ID No:208)

$T_1$ seed from 16 events of CW00536 containing Ceres Annot: 847799 was analyzed as described in Example 1. The plant height and panicle weight of transgenic $T_1$ plants in comparison to plants not containing the transgene grown at the same location is shown in Tables 14 and 15. The data points represent an average of 16 events with 15 transgenic plants per event and an average of several hundred control plants. An increase in height and panicle weight was shown in comparison to plants not containing the transgene.

TABLE 14

| Panicle wt (g)/plant | | | |
|---|---|---|---|
| Control | STDEV | Transgenic | STDEV |
| 17.916 | 2.181 | 20.854 | 3.419 |

TABLE 15

Plant Height (cm)

| Event | Percent Increase over control |
|---|---|
| CW00536-03 | 7.79 |
| CW00536-05 | 5.66 |
| CW00536-11 | 8.71 |
| CW00536-12 | 8.47 |
| CW00536-20 | 8.77 |

Example 12—Results for Rice Events SR05004, CW00191, CeresAnnot: 878355 (SEQ ID NO: 425)

Biomass from plants grown from $T_2$ and $T_3$ seed from one event of CW00191 containing CeresAnnot: 878355 was analyzed as described in Example 1. The average biomass of transgenic $T_2$ and $T_3$ plants in comparison to plants not containing the transgene grown at the same location is shown in Table 16. The low nitrogen plots and control plots were each replicated 3 times in randomized block design, having transgenic plants representing multiple events and controls. Each plot contained 40 plants. Ten plants were measured per plot for one event of CW00191. Each of the biomass values presented in Table 16 represents an average of 30 plants measured. The results show a measured increase in biomass for transgenic plants under normal and low nitrogen conditions in comparison to plants not containing the transgene.

TABLE 16

| Biomass (g)/plant (normal) | | Biomass (g)/plant (Low N) | |
|---|---|---|---|
| Control | Transgenic | Control | Transgenic |
| 14.6 | 16.75 | 16.01 | 19.64 |

Example 13—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO: 554, 263, 117, 1, 645, 253, 323, 595, 77, 209, and 426 are shown in FIGS. 1-11, respectively. Additional exemplary homologs are correlated to certain Figures in the Sequence Listing.

Example 14—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 554.

The procedure above was repeated and an HMM was generated for each group of sequences shown in FIGS. 2-11, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12319921B2). An electronic copy of the sequence listing will also be available from the USPTO upon request and payment of the fee set forth in 37 CFR 1.19(b)(3).

What is claimed is:

1. A method of producing a monocotyledonous plant, said method comprising
   growing a plant cell comprising an exogenous nucleic acid, said exogenous nucleic acid comprising a regulatory region operably linked to a nucleotide sequence, wherein the nucleotide sequence encodes a polypeptide comprising an amino acid sequence having 95 percent or greater sequence identity to the amino acid sequence of SEQ ID NO:253, producing a plant from said plant cell, and
   selecting the plant for increased panicle weight by at least about 35 percent as compared to the corresponding level of a control plant that does not comprise said exogenous nucleic acid.

2. The method of claim 1, wherein said polypeptide comprises the amino acid sequence of SEQ ID NO:253.

3. The method of claim 1, wherein the polynucleotide comprises the nucleotide sequence of SEQ ID NO: 252.

4. The method of claim 1, wherein the polypeptide has 97 percent or greater sequence identity to the amino acid sequence of SEQ ID NO: 253.

5. A transgenic monocotyledonous plant comprising an exogenous nucleic acid,
   wherein the exogenous nucleic acid comprises a regulatory region operably linked to a nucleotide sequence,
   wherein the nucleotide sequence encodes a polypeptide comprising an amino acid sequence having 95 percent or greater sequence identity to the amino acid sequence of SEQ ID NO:253,
   wherein the monocotyledonous plant is selected for increased panicle weight by at least about 35 percent as compared to the corresponding level of a control plant that does not comprise said exogenous nucleic acid.

6. A monocotyledonous plant cell from the monocotyledonous plant of claim 5, wherein the monocotyledonous plant cell comprises the exogenous nucleic acid.

7. The transgenic plant of claim 5, wherein the plant is selected from the group consisting of switchgrass, sorghum, miscanthus, energycane, corn, wheat, and rice.

8. The transgenic monocotyledonous plant of claim 5, wherein said polypeptide comprises the amino acid sequence of SEQ ID NO:253.

9. A seed product comprising embryonic tissue from the transgenic monocotyledonous plant according to claim 8, wherein the seed product comprises the exogenous nucleic acid.

10. The transgenic monocotyledonous plant of claim 5, wherein the polynucleotide comprises the nucleotide sequence of SEQ ID NO: 252.

11. The transgenic monocotyledonous plant of claim 5, wherein the polypeptide has 97 percent or greater sequence identity to the amino acid sequence of SEQ ID NO: 253.

12. A seed produced by the transgenic monocotyledonous plant of claim 5, wherein the seed comprises the exogenous nucleic acid.

13. A progeny of the transgenic monocotyledonous plant of claim 5, wherein the progeny exhibits the increased panicle weight and comprises the exogenous nucleic acid.

* * * * *